US009914974B2

(12) United States Patent
Bajic et al.

(10) Patent No.: US 9,914,974 B2
(45) Date of Patent: *Mar. 13, 2018

(54) MOLECULAR BIOMARKER SET FOR EARLY DETECTION OF OVARIAN CANCER

(71) Applicant: King Abdullah University of Science and Technology, Thuwal (SA)

(72) Inventors: Vladimir Bajic, Thuwal (SA); Mandeep Kaur, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

This patent is subject to a terminal disclaimer.

(21) Appl. No.: 14/734,190

(22) Filed: Jun. 9, 2015

(65) Prior Publication Data

US 2015/0284809 A1 Oct. 8, 2015

Related U.S. Application Data

(63) Continuation of application No. 13/415,004, filed on Mar. 8, 2012, now Pat. No. 9,057,107.

(60) Provisional application No. 61/450,212, filed on Mar. 8, 2011.

(51) Int. Cl.
| | | |
|---|---|---|
| C12Q 1/68 | (2018.01) | |
| G01N 33/487 | (2006.01) | |
| G01N 33/50 | (2006.01) | |
| G01N 33/574 | (2006.01) | |

(52) U.S. Cl.
CPC ..... *C12Q 1/6886* (2013.01); *G01N 33/57449* (2013.01); *C12Q 2600/118* (2013.01); *C12Q 2600/158* (2013.01); *G01N 2333/47* (2013.01); *G01N 2800/50* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,950 A | 2/1976 | Nishida et al. | 192/225 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 4,800,159 A | 1/1989 | Mullis et al. | 435/91.2 |
| 4,883,750 A | 11/1989 | Whiteley et al. | 435/6.16 |
| 4,946,773 A | 8/1990 | Maniatis et al. | 435/6.11 |
| 5,279,721 A | 1/1994 | Schmid | 204/457 |
| 5,840,873 A | 11/1998 | Nelson et al. | 536/24.3 |
| 5,843,640 A | 12/1998 | Patterson et al. | 435/5 |
| 5,843,650 A | 12/1998 | Segev | 435/6.1 |
| 5,843,651 A | 12/1998 | Stimpson et al. | 435/6.11 |
| 5,843,663 A | 12/1998 | Stanley et al. | 435/6.11 |
| 5,846,708 A | 12/1998 | Hollis et al. | 23/92 |
| 5,846,709 A | 12/1998 | Segev | 435/6.1 |
| 5,846,717 A | 12/1998 | Brow et al. | 435/6.18 |
| 5,846,726 A | 12/1998 | Nadeau et al. | 435/6.12 |
| 5,846,729 A | 12/1998 | Wu et al. | 435/6.12 |
| 5,846,783 A | 12/1998 | Wu et al. | 435/91.2 |
| 5,849,481 A | 12/1998 | Urdea et al. | 435/6.11 |
| 5,849,483 A | 12/1998 | Shuber | 435/5 |
| 5,849,486 A | 12/1998 | Heller et al. | 435/6.11 |
| 5,849,487 A | 12/1998 | Hase et al. | 435/6.12 |
| 5,849,497 A | 12/1998 | Steinman | 435/6.11 |
| 5,849,546 A | 12/1998 | Sousa et al. | 435/91.5 |
| 5,849,547 A | 12/1998 | Cleuziat et al. | 435/91.21 |
| 5,851,770 A | 12/1998 | Babon et al. | 435/6.14 |
| 5,851,772 A | 12/1998 | Mirzabekov et al. | 435/6.14 |
| 5,853,990 A | 12/1998 | Winger et al. | 435/6.18 |
| 5,853,992 A | 12/1998 | Glazer et al. | 435/6.12 |
| 5,853,993 A | 12/1998 | Dellinger et al. | 435/6.14 |
| 5,856,092 A | 1/1999 | Dale et al. | 435/6.11 |
| 5,858,652 A | 1/1999 | Laffler et al. | 435/5 |
| 5,861,244 A | 1/1999 | Wang et al. | 435/6.14 |
| 5,863,732 A | 1/1999 | Richards | 435/6.1 |
| 5,863,753 A | 1/1999 | Haugland et al. | 435/34 |
| 5,866,331 A | 2/1999 | Singer et al. | 435/6.11 |
| 5,866,337 A | 2/1999 | Schon | 435/6.18 |
| 5,866,366 A | 2/1999 | Kallender | 435/69.1 |

(Continued)

FOREIGN PATENT DOCUMENTS

| | | |
|---|---|---|
| EP | 329 822 | 2/1988 |
| EP | 320 308 | 6/1989 |

(Continued)

OTHER PUBLICATIONS

Bioinfomatics (Bioinfomatics 2006).*
Adib TR, Henderson S, Perrett C, Hewitt D, Bourmpoulia D, Ledermann J, Boshoff C., "Predicting biomarkers for ovarian cancer using gene-expression microarrays", Br J Cancer 2004, 90:686-692.
Anttila et al., "Expression of transcription factor AP-2α predicts survival in epithelial ovarian cancer", British Journal of Cancer (2000), vol. 82, No. 12, pp. 1974-1983.
Arocho Alaina, Ladanyi Marc, Pan Qiulu. "Validation of the 2[DELTA][DELTA]Ct Calculation as an Alternate Method of Data Analysis for Quantitative PCR of BCR-ABL P210 Transcripts". Diagnostic Molecular Pathology: Mar. 2006, vol. 15, Issue 1, pp. 56-61.

(Continued)

*Primary Examiner* — Julie Wu
(74) *Attorney, Agent, or Firm* — Smith, Gambrell & Russell

(57) ABSTRACT

Embodiments of the present invention concern methods and compositions related to detection of ovarian cancer, including detection of the stage of ovarian cancer, in some cases. In particular, the invention encompasses use of expression of TFAP2A and in some embodiments CA125 and/or E2F5 to identify ovarian cancer, including detecting mRNA and/or protein levels of the respective gene products. Kits for detection of ovarian cancer are also described.

13 Claims, 5 Drawing Sheets

(56) References Cited

U.S. PATENT DOCUMENTS

| | | | |
|---|---|---|---|
| 5,882,864 A | 3/1999 | An et al. | 435/6.14 |
| 5,900,481 A | 5/1999 | Laugh et al. | 506/30 |
| 5,905,024 A | 5/1999 | Mirzabekov et al. | 435/6.12 |
| 5,910,407 A | 6/1999 | Vogelstein et al. | 435/6.14 |
| 5,912,124 A | 6/1999 | Kumar | 435/6.12 |
| 5,912,145 A | 6/1999 | Stanley | 435/91.1 |
| 5,912,148 A | 6/1999 | Eggerding | 435/91.2 |
| 5,912,548 A | 6/1999 | Downs et al. | 320/150 |
| 5,916,776 A | 6/1999 | Kumar | 435/91.1 |
| 5,916,779 A | 6/1999 | Pearson et al. | 435/91.2 |
| 5,919,626 A | 7/1999 | Shi et al. | 435/6.14 |
| 5,919,630 A | 7/1999 | Nadeau et al. | 435/6.12 |
| 5,922,574 A | 7/1999 | Minter | 435/91.1 |
| 5,925,517 A | 7/1999 | Tyagi et al. | 435/6.1 |
| 5,925,525 A | 7/1999 | Fodor et al. | 506/3 |
| 5,928,862 A | 7/1999 | Morrison | 435/6.18 |
| 5,928,869 A | 7/1999 | Nadeau et al. | 435/6.18 |
| 5,928,870 A | 7/1999 | Lapidus et al. | 435/6.14 |
| 5,928,905 A | 7/1999 | Stemmer et al. | 435/91.1 |
| 5,928,906 A | 7/1999 | Koster et al. | 435/91.2 |
| 5,929,227 A | 7/1999 | Glazer et al. | 536/26.6 |
| 5,932,413 A | 8/1999 | Celebuski | 435/6.11 |
| 5,932,451 A | 8/1999 | Wang et al. | 435/91.21 |
| 5,935,791 A | 8/1999 | Nadeau et al. | 435/6.18 |
| 5,935,825 A | 8/1999 | Nishimura et al. | 435/91.2 |
| 5,939,291 A | 8/1999 | Loewy et al. | 435/91.2 |
| 5,942,391 A | 8/1999 | Zhang et al. | 435/6.12 |
| 7,605,003 B2 | 10/2009 | Chan et al. | 436/178 |
| 7,670,792 B2 | 3/2010 | Farias-Eisner et al. | 435/7.23 |
| 7,741,019 B2 | 6/2010 | Diamandis et al. | 435/4 |
| 7,745,149 B2 | 6/2010 | Chow | 435/7.1 |
| 9,057,107 B2 * | 6/2015 | Bajic | C12Q 1/6886 |

FOREIGN PATENT DOCUMENTS

| | | |
|---|---|---|
| GB | 2 202 328 | 9/1988 |
| WO | WO 87/006270 | 10/1987 |
| WO | WO 88/10315 | 12/1988 |
| WO | WO 89/06700 | 7/1989 |
| WO | WO 89/009284 | 10/1989 |
| WO | WO 90/07641 | 7/1990 |
| WO | WO 2003/057014 | 7/2003 |
| WO | WO 2005/014781 | 2/2005 |
| WO | WO 2006/089091 | 8/2006 |

OTHER PUBLICATIONS

Bär M, Bär D, Lehmann B: Selection and validation of candidate housekeeping genes for studies of human keratinocytes—review and recommendations. J Invest Dermatol. 2009, 129(3):535-7. Review.

Frohman, In: PCR Protocols: A Guide to Methods and Applications, Academic Press, N.Y., 1990.

Gene Expression Omnibus (GEO) search results for CA125 and blood; Mar. 2, 2014.

Gene Expression Omnibus (GEO) search results for E2F5 and blood; Mar. 2, 2014.

Gene Expression Omnibus (GEO) search results for TFAP2A and blood; Mar. 2, 2014.

Hendrix ND, Wu R, Kuick R, Schwartz DR, Fearon ER, Cho KR: Fibroblast growth factor 9 has oncogenic activity and is a downstream target of Wnt signaling in ovarian endometrioid adenocarcinomas. Cancer Res 2006, 66:1354-1362.

Innis et al., "DNA sequencing with Thermus aquaticus DNA polymerase and direct sequencing of polymerase chain reaction—amplified DNA," Proc Natl Acad Sci U S A. 85(24):9436-9440, 1988.

International Search Report and Written Opinion for PCT/IB2012/000552, dated Apr. 11, 2013.

Kaur et al., "In Silico discovery of transcription factors as potential diagnostic biomarkers of ovarian cancer", BMC Systems Biology 2011, vol. 5, No. 144, www.biomedcentral.com.

Kothandaraman N, Bajic VB, Brendan PN, Huak CY, Keow PB, Razvi K, Salto-Tellez M, Choolani M. "E2F5 status significantly improves malignancy diagnosis of epithelial ovarian cancer". BMC Cancer. Feb. 24, 2010; 10:64.

Kwoh et al., Transcription-based amplification system and detection of amplified human immunodeficiency virus type 1 with a bead-based sandwich hybridization format, Proc Natl Acad Sci U S A. 86(4):1173-1177, 1989.

Lu KH, Patterson AP, Wang L, Marquez RT, Atkinson EN, Eagerly KA, Ramoth LR, Rosen DG, Liu J, Hellstrom I, et al.: Selection of potential markers for epithelial ovarian cancer with gene expression arrays and recursive descent partition analysis. Clin Cancer Res 2004, 10:3291-3300.

Ohara et al., "One-sided polymerase chain reaction: the amplification of cDNA," Proc Natl Acad Sci U S A. 86(15):5673-5677, 1989.

Sasaroli D, Coukos G, Scholler N: Beyond CA125: the coming of age of ovarian cancer biomarkers. Are we there yet? Biomark Med 2009, 3:275-288.

Tunbridge EM, Eastwood SL, Harrison PJ: Changed relative to what? Housekeeping genes and normalization strategies in human brain gene expression studies. Biol Psychiatry. Jan. 15, 2011;69(2):173-9. Review.

Walker et al., "Strand displacement amplification—an isothermal, in vitro DNA amplification technique," Nucleic Acids Res. 20(7):1691-1696, 1992.

* cited by examiner

SEQUENCE LISTING

```
<160> NUMBER OF SEQ ID NOS: 6

<210> SEQ ID NO 1
<211> LENGTH: 3300
<212> TYPE: DNA
<213> ORGANISM: Homo sapiens

<400> SEQUENCE: 1
acgggagctc tttcccttct ctcctcctcc tcgcccttct cctcgccctc ctcctcctcc      60
tcgccctcct cttcctcctc ctcctccttg ccctcctcct ctccctcctc cttctcctcc     120
tccacctcct ctccctcctc ctcctcctcc tgcgctcacc gccggcagcc agcactttgc     180
gctcacccag agagtagctc cacttgggtg cgagaccgag aggggcatat ccgttcacgc     240
cgatccatga aaatgctttg gaaattgacg gataatatca agtacgagga ctgcgaggac     300
cgtcacgacg gcaccagcaa cgggacggca cggttgcccc agctgggcac tgtaggtcaa     360
tctccctaca cgagcgcccc gccgctgtcc cacaccccca atgccgactt ccagccccca     420
tacttccccc caccctacca gcctatctac ccccagtcgc aagatcctta ctcccacgtc     480
aacgacccct acagcctgaa cccctgcac gcccagccgc agccgcagca cccaggctgg     540
cccggccaga ggcagagcca ggagtctggg ctcctgcaca cgcaccgggg gctgcctcac     600
cagctgtcgg gcctggatcc tcgcagggac tacaggcggc acgaggacct cctgcacggc     660
ccacacgcgc tcagctcagg actcggagac ctctcgatcc actccttacc tcacgccatc     720
gaggaggtcc cgcatgtaga agacccgggt attaacatcc cagatcaaac tgtaattaag     780
aaaggccccg tgtccctgtc caagtccaac agcaatgccg tctccgccat ccctattaac     840
aaggacaacc tcttcggcgg cgtggtgaac cccaacgaag tcttctgttc agttccgggt     900
```

```
cgcctctcgc tcctcagctc cacctcgaag tacaaggtca cggtggcgga agtgcagcgg    960
cggctctcac cacccgagtg tctcaacgcg tcgctgctgg gcggagtgct ccggagggcg   1020
aagtctaaaa atggaggaag atctttaaga gaaaaactgg acaaaatagg attaaatctg   1080
cctgcaggga gacgtaaagc tgccaacgtt accctgctca catcactagt agagggagaa   1140
gctgtccacc tagccaggga ctttgggtac gtgtgcgaaa ccgaatttcc tgccaaagca   1200
gtagctgaat ttctcaaccg acaacattcc gatcccaatg agcaagtgac aagaaaaaac   1260
atgctcctgg ctacaaaaca gatatgcaaa gagttcaccg acctgctggc tcaggaccga   1320
tctcccctgg ggaactcacg gcccaacccc atcctggagc ccggcatcca gagctgcttg   1380
acccacttca acctcatctc ccacggcttc ggcagccccg cggtgtgtgc cgcggtcacg   1440
gccctgcaga actatctcac cgaggccctc aaggccatgg acaaaatgta cctcagcaac   1500
aaccccaaca gccacacgga caacaacgcc aaaagcagtg acaagagga gaagcacaga   1560
aagtgaggct ctcctcccgc cccgcccctc ccacgcctca ccagcccccc gcgcgcccac   1620
cctccggcgg gtgacagctc cgggatcagc aacccttcct gctgctgcta ctgctgctgc   1680
tgctgccgcc gccgccgccg ccgctgccct tgggtccccc cgagtctccg ggactgccct   1740
ctcgactgtc agtggggcag cctctccgac tctgcacccg cctcgacctc cccacccgct   1800
cccacacccc tgtgccctca tgtggagcct aagagaacag aacaggccgt gaagccagca   1860
gagaaaagtt ctgccaagtt tgtgaaccct ttttttttta acaaaacaa caaatcaaca   1920
acagcaacaa caacaacaaa aattaaaaac ttttttctaa aaaaaagtg aaaataaaaa   1980
aaattatatg cgcttcatgg gactgagtca ccaccttccc ttacatactt cagttcagat   2040
tgtagccata cttaaaaaaa aaaaaaaagc caaagatga tgacaacatt tttatcagta   2100
ttgtgaataa acttgaacac aaatacacga agttccatgt catgtcttca gttgtagaag   2160
ttttcctct ttaaggtaaa gcgaccaact tgaactttct ctggcaacac gattcgcagt   2220
tatataaggg aatcagtgtt cacgtctctg tatatattta tttatgtgta atttaatggg   2280
aattgtaaat atggtgagtc tgttttaagc ctttttttt tttatttatct gatcttgttt   2340
acctcttgtt tagtgggttt tgaatcttcc ctattagttc ttcatgtggt tcatggtact   2400
gatttagaaa tccagtgttt gggggatttt tttctctggg attcatgaat ttagccctgt   2460
tgtagcatgt taaggtgac aaacagctgg acaaattttt aaaagtaaa ataaatttt   2520
atctataatt agtattatta catttagctt ttcattgaac cgaaagaaaa aaagtgatat   2580
tggaccctgg aaagattttg aaacttgagt ggtttgataa cccttctatg tattgtaggg   2640
agaaaaaaaa aagtttattt tattccactg tcctccctta aaagcatcat ttgagcaata   2700
aatgaatatt gtcttaaac caagggttag ggaattttcc tctctctctc tctctcctct   2760
ctctttctgt tcaaagaact tcaaacattt gggaccacct ggtattctgt attttcactg   2820
gccatattgg aagcagttct agttgcattg tattgagttg tgctggcagt agtttccatg   2880
cctgtcaatg tatcatagtc ctttgttgcc cagataaata aatatttgat acgctttatg   2940
tcgatttttt tttattcagt ggctgtcttt acccaggcgt attttgttc ttggcagtat   3000
tttttattca gtatggttac agtaattgag tttaactctc ccttggcaat tgctccttgc   3060
aataagcagc tgaacccatt gtttccctca agtataataa aaacttactt tcaacttgga   3120
gttcagagca gggtatcatt tagatattcc actgtgtctg tattcagaca aatgacacaa   3180
taaaacccaa tgtattcttt tggataaaag attgtttgta ctgctaaagg aatgacatac   3240
tgtcttttcc ttactagaaa cattaatttt attattaaaa ataaagtttt attttattta   3300
```

<210> SEQ ID NO 2
<211> LENGTH: 437
<212> TYPE: PRT
<213> ORGANISM: Homo sapiens

<400> SEQUENCE: 2

```
Met Leu Trp Lys Leu Thr Asp Asn Ile Lys Tyr Glu Asp Cys Glu Asp
1               5                   10                  15

Arg His Asp Gly Thr Ser Asn Gly Thr Ala Arg Leu Pro Gln Leu Gly
                20                  25                  30

Thr Val Gly Gln Ser Pro Tyr Thr Ser Ala Pro Pro Leu Ser His Thr
            35                  40                  45

Pro Asn Ala Asp Phe Gln Pro Pro Tyr Phe Pro Pro Tyr Gln Pro
    50                  55                  60

Ile Tyr Pro Gln Ser Gln Asp Pro Tyr Ser His Val Asn Asp Pro Tyr
65                  70                  75                  80

Ser Leu Asn Pro Leu His Ala Gln Pro Gln Pro Gln His Pro Gly Trp
                85                  90                  95

Pro Gly Gln Arg Gln Ser Gln Glu Ser Gly Leu Leu His Thr His Arg
                100                 105                 110

Gly Leu Pro His Gln Leu Ser Gly Leu Asp Pro Arg Arg Asp Tyr Arg
            115                 120                 125

Arg His Glu Asp Leu Leu His Gly Pro His Ala Leu Ser Ser Gly Leu
        130                 135                 140

Gly Asp Leu Ser Ile His Ser Leu Pro His Ala Ile Glu Glu Val Pro
145                 150                 155                 160

His Val Glu Asp Pro Gly Ile Asn Ile Pro Asp Gln Thr Val Ile Lys
                165                 170                 175

Lys Gly Pro Val Ser Leu Ser Lys Ser Asn Ser Asn Ala Val Ser Ala
                180                 185                 190

Ile Pro Ile Asn Lys Asp Asn Leu Phe Gly Gly Val Val Asn Pro Asn
            195                 200                 205

Glu Val Phe Cys Ser Val Pro Gly Arg Leu Ser Leu Leu Ser Ser Thr
    210                 215                 220

Ser Lys Tyr Lys Val Thr Val Ala Glu Val Gln Arg Arg Leu Ser Pro
225                 230                 235                 240

Pro Glu Cys Leu Asn Ala Ser Leu Leu Gly Val Leu Arg Arg Ala
                245                 250                 255

Lys Ser Lys Asn Gly Gly Arg Ser Leu Arg Glu Lys Leu Asp Lys Ile
                260                 265                 270

Gly Leu Asn Leu Pro Ala Gly Arg Arg Lys Ala Ala Asn Val Thr Leu
            275                 280                 285

Leu Thr Ser Leu Val Glu Gly Glu Ala Val His Leu Ala Arg Asp Phe
        290                 295                 300

Gly Tyr Val Cys Glu Thr Glu Phe Pro Ala Lys Ala Val Ala Glu Phe
305                 310                 315                 320

Leu Asn Arg Gln His Ser Asp Pro Asn Glu Gln Val Thr Arg Lys Asn
                325                 330                 335

Met Leu Leu Ala Thr Lys Gln Ile Cys Lys Glu Phe Thr Asp Leu Leu
                340                 345                 350

Ala Gln Asp Arg Ser Pro Leu Gly Asn Ser Arg Pro Asn Pro Ile Leu
            355                 360                 365

Glu Pro Gly Ile Gln Ser Cys Leu Thr His Phe Asn Leu Ile Ser His
```

```
                370             375             380
Gly Phe Gly Ser Pro Ala Val Cys Ala Ala Val Thr Ala Leu Gln Asn
385                 390                 395                 400

Tyr Leu Thr Glu Ala Leu Lys Ala Met Asp Lys Met Tyr Leu Ser Asn
                405                 410                 415

Asn Pro Asn Ser His Thr Asp Asn Asn Ala Lys Ser Ser Asp Lys Glu
                420                 425                 430

Glu Lys His Arg Lys
        435

<210> SEQ ID NO 3
<211> LENGTH: 1743
<212> TYPE: DNA
<213> ORGANISM: Homo sapiens

<400> SEQUENCE: 3
gtgcgcgggg gcccgaccac cgcggggccg ggacgcgatg gcggcggcag agcccgcgag    60
ctcgggccag caggcgccgg cagggcaggg gcagggccag cggccgccgc cgcagcctcc   120
gcaggcgcaa gccccgcagc cgcccccgcc gccgcagctc ggggcgccg ggggcggcag   180 cagcaggcac gagaagagcc tggggctgct cactaccaag ttcgtgtcgc tgctgcagga   240
ggccaaggac ggcgttctgg atctcaaagc ggctgctgat actttggctg tgaggcaaaa   300
aaggagaatt tatgatatca ccaatgtctt agagggaatt gacttgattg aaaaaaagtc   360
aaaaaacagt atccagtgga aggtgtagg tgctggctgt aatactaaag aagtcataga   420
tagattaaga tatcttaaag ctgaaattga agatctagaa ctgaaggaaa gagaacttga   480
tcagcagaag ttgtggctac agcaaagcat caaaaatgtg atggacgatt ccattaataa   540
tagattttcc tatgtaactc atgaagacat ctgtaattgc tttaatggtg atacactttt   600
ggccattcag gcaccttctg gtacacaact ggaggtaccc attccagaaa tgggtcagaa   660
tggacaaaag aaataccaga tcaatctaaa gagtcattca ggacctatcc atgtgctgct   720
tataaataaa gagtcgagtt catctaagcc cgtggttttt cctgttcccc cacctgatga   780
cctcacacag ccttcctccc agtccttgac tccagtgact ccacagaaat ccagcatggc   840
aactcaaaat ctgcctgagc aacatgtctc tgaaagaagc caggctctgc agcagacatc   900
agctacagat atatcttcag caggatctat tagtggagat atcattgatg agttaatgtc   960
ttctgacgtg tttcctctct taaggctttc tcctaccccg gcagatgact acaactttaa  1020
tttagatgat aacgaaggag tttgtgatct gtttgtgatc cagatactaa attattagat  1080
tccatggaaa cttgggactg ttatctacct ctaactgtgt aacattttag acttcttaat  1140
aacctaaata tttaaaataa tgaatgtaac accttttta gttcactgat tctgaagtgt  1200
tcttccctaa tactttcttt acttcacaaa acttcaacca taaaaacaaa gggctctgat  1260
tgctttaggg gataagtgat ttaatatcca caaacgtccc cactcccaaa agtaactata  1320
ttctggattt caacttttct tctaattgtg aatccttctg ttttttcttc ttaaggagga  1380
aagttaaagg acactacagg tcatcaaaaa caagttggcc aaggactcat tacttgtctt  1440 atattttac tgccactaaa ctgcctgtat ttctgtatgt ccttctatcc aaacagacgt  1500
tcactgccac ttgtaaagtg aaggatgtaa acgaggatat ataactgttt cagtgaacag  1560
attttgtgaa gtgccttctg ttttagcact ttaagtttat cacattttgt tgacttctga  1620
cattccactt tcctaggtta taggaaagat ctgtttatgt agtttgtttt taaaatgtgc  1680
caatgcctgt acattaacaa gattttttaaa aataaaattg tataaaacat tcaaaaaaaa  1740
``` aaa                                                                1743

<210> SEQ ID NO 4
<211> LENGTH: 346
<212> TYPE: PRT
<213> ORGANISM: Homo sapiens

<400> SEQUENCE: 4

Met Ala Ala Glu Pro Ala Ser Ser Gly Gln Gln Ala Pro Ala Gly
1               5                   10                  15

Gln Gly Gln Gly Gln Arg Pro Pro Gln Pro Pro Gln Ala Gln Ala
            20                  25                  30

Pro Gln Pro Pro Pro Pro Gln Leu Gly Ala Gly Gly Gly Ser
        35                  40                  45

Ser Arg His Glu Lys Ser Leu Gly Leu Leu Thr Thr Lys Phe Val Ser
50                  55                  60

Leu Leu Gln Glu Ala Lys Asp Gly Val Leu Asp Leu Lys Ala Ala Ala
65                  70                  75                  80

Asp Thr Leu Ala Val Arg Gln Lys Arg Arg Ile Tyr Asp Ile Thr Asn
                85                  90                  95

Val Leu Glu Gly Ile Asp Leu Ile Glu Lys Lys Ser Lys Asn Ser Ile
                100                 105                 110

Gln Trp Lys Gly Val Gly Ala Gly Cys Asn Thr Lys Glu Val Ile Asp
            115                 120                 125

Arg Leu Arg Tyr Leu Lys Ala Glu Ile Glu Asp Leu Glu Leu Lys Glu
130                 135                 140

Arg Glu Leu Asp Gln Gln Lys Leu Trp Leu Gln Gln Ser Ile Lys Asn
145                 150                 155                 160

Val Met Asp Asp Ser Ile Asn Asn Arg Phe Ser Tyr Val Thr His Glu
                165                 170                 175

Asp Ile Cys Asn Cys Phe Asn Gly Asp Thr Leu Leu Ala Ile Gln Ala
                180                 185                 190

Pro Ser Gly Thr Gln Leu Glu Val Pro Ile Pro Glu Met Gly Gln Asn
            195                 200                 205

Gly Gln Lys Lys Tyr Gln Ile Asn Leu Lys Ser His Ser Gly Pro Ile
210                 215                 220

His Val Leu Leu Ile Asn Lys Glu Ser Ser Ser Lys Pro Val Val
225                 230                 235                 240

Phe Pro Val Pro Pro Asp Asp Leu Thr Gln Pro Ser Ser Gln Ser
                245                 250                 255

Leu Thr Pro Val Thr Pro Gln Lys Ser Ser Met Ala Thr Gln Asn Leu
            260                 265                 270

Pro Glu Gln His Val Ser Glu Arg Ser Gln Ala Leu Gln Gln Thr Ser
            275                 280                 285

Ala Thr Asp Ile Ser Ser Ala Gly Ser Ile Ser Gly Asp Ile Ile Asp
            290                 295                 300

Glu Leu Met Ser Ser Asp Val Phe Pro Leu Leu Arg Leu Ser Pro Thr
305                 310                 315                 320

Pro Ala Asp Asp Tyr Asn Phe Asn Leu Asp Asp Asn Glu Gly Val Cys
                325                 330                 335

Asp Leu Phe Asp Val Gln Ile Leu Asn Tyr
            340                 345

<210> SEQ ID NO 5

<211> LENGTH: 43816
<212> TYPE: DNA
<213> ORGANISM: Homo sapiens

<400> SEQUENCE: 5

| | | | | | |
|---|---|---|---|---|---|
| aagcgttgca | caattccccc | aacctccata | catacggcag | ctcttctaga | cacaggtttt | 60 |
| cccaggtcaa | atgcgggac | cccagccata | tctcccaccc | tgagaaattt | tggagtttca | 120 |
| gggagctcag | aagctctgca | gaggccaccc | tctctgaggg | gattcttctt | agacctccat | 180 |
| ccagaggcaa | atgttgacct | gtccatgctg | aaaccctcag | gccttcctgg | gtcatcttct | 240 |
| cccacccgct | ccttgatgac | agggagcagg | agcactaaag | ccacaccaga | aatggattca | 300 |
| ggactgacag | gagccacctt | gtcacctaag | acatctacag | gtgcaatcgt | ggtgacagaa | 360 |
| catactctgc | cctttacttc | cccagataag | accttggcca | gtcctacatc | ttcggttgtg | 420 |
| ggaagaacca | cccagtcttt | ggggtgatg | tcctctgctc | tccctgagtc | aacctctaga | 480 |
| ggaatgacac | actccgagca | agaaccagc | ccatcgctga | gtcccaggt | caatggaact | 540 |
| ccctctagga | actaccctgc | tacaagcatg | gtttcaggat | tgagttcccc | aaggaccagg | 600 |
| accagttcca | cagaaggaaa | ttttaccaaa | gaagcatcta | catacacact | cactgtagag | 660 |
| accacaagtg | gcccagtcac | tgagaagtac | acagtcccca | ctgagacctc | aacaactgaa | 720 |
| ggtgacagca | cagagacccc | ctgggacaca | agatatattc | ctgtaaaaat | cacatctcca | 780 |
| atgaaaacat | ttgcagattc | aactgcatcc | aaggaaaatg | ccccagtgtc | tatgactcca | 840 |
| gctgagacca | cagttactga | ctcacatact | ccaggaagga | caaacccatc | atttgggaca | 900 |
| ctttattctt | cctccttga | cctatcacct | aaagggaccc | caaattccag | aggtgaaaca | 960 |
| agcctggaac | tgattctatc | aaccactgga | tatcccttct | cctctcctga | acctggctct | 1020 |
| gcaggacaca | gcagaataag | taccagtgcg | cctttgtcat | catctgcttc | agttctcgat | 1080 |
| aataaaatat | cagagaccag | catattctca | ggccagagtc | tcacctcccc | tctgtctcct | 1140 |
| ggggtgcccg | aggccagagc | cagcacaatg | cccaactcag | ctatcccttt | ttccatgaca | 1200 |
| ctaagcaatg | cagaaacaag | tgccgaaagg | gtcagaagca | caatttcctc | tctggggact | 1260 |
| ccatcaatat | ccacaaagca | gacagcagag | actatcctta | ccttccatgc | cttcgctgag | 1320 |
| accatggata | tacccagcac | ccacatagcc | aagactttgg | cttcagaatg | gttgggaagt | 1380 |
| ccaggtaccc | ttggtggcac | cagcacttca | gcgctgacaa | ccacatctcc | atctaccact | 1440 |
| ttagtctcag | aggagaccaa | cacccatcac | tccacgagtg | gaaaggaaac | agaaggaact | 1500 |
| ttgaatacat | ctatgactcc | acttgagacc | tctgctcctg | gagaagagtc | cgaaatgact | 1560 |
| gccaccttgg | tccccactct | aggttttaca | actcttgaca | gcaagatcag | aagtccatct | 1620 |
| caggtctctt | catcccaccc | aacaagagag | ctcagaacca | caggcagcac | ctctgggagg | 1680 |
| cagagttcca | gcacagctgc | ccacgggagc | tctgacatcc | tgagggcaac | cacttccagc | 1740 |
| acctcaaaag | catcatcatg | gaccagtgaa | agcacagctc | agcaatttag | tgaaccccag | 1800 |
| cacacacagt | gggtggagac | aagtcctagc | atgaaaacag | agagaccccc | agcatcaacc | 1860 |
| agtgtggcag | ccctatcac | cacttctgtt | ccctcagtgg | tctctggctt | caccacctg | 1920 |
| aagaccagct | ccacaaaagg | gatttggctt | gaagaaacat | ctgcagacac | actcatcgga | 1980 |
| gaatccacag | ctggcccaac | cacccatcag | tttgctgttc | ccactgggat | ttcaatgaca | 2040 |
| ggaggcagca | gcaccagggg | aagccagggc | acaaccccacc | tactcaccag | agccacagca | 2100 |
| tcatctgaga | catccgcaga | tttgactctg | gccacgaacg | tgtcccagt | ctccgtgtct | 2160 |
| ccagcagtga | gcaagacggc | tgctggctca | agtcctccag | gagggacaaa | gccatcatat | 2220 |

```
acaatggttt cttctgtcat ccctgagaca tcatctctac agtcctcagc tttcagggaa    2280
ggaaccagcc tgggactgac tccattaaac actagacatc ccttctcttc ccctgaacca    2340
gactctgcag gacacaccaa gataagcacc agcattcctc tgttgtcatc tgcttcagtt    2400
cttgaggata aagtgtcagc gaccagcaca ttctcacacc acaaagccac ctcatctatt    2460
accacaggga ctcctgaaat ctcaacaaag acaaagccca gctcagccgt tctttcctcc    2520
atgaccctaa gcaatgcagc aacaagtcct gaaagagtca gaaatgcaac ttcccctctg    2580
actcatccat ctccatcagg ggaagagaca gcagggagtg tcctcactct cagcacctct    2640
gctgagacta cagactcacc taacatccac ccaactggga cactgacttc agaatcgtca    2700
gagagtccta gcactctcag cctcccaagt gtctctggag tcaaaaccac attttcttca    2760
tctactcctt ccactcatct atttactagt ggagaagaaa cagaggaaac ttcgaatcca    2820
tctgtgtctc aacctgagac ttctgtttcc agagtaagga ccaccttggc cagcacctct    2880
gtccctaccc cagtattccc caccatggac acctggccta cacgttcagc tcagttctct    2940
tcatcccacc tagtgagtga gctcagagct acgagcagta cctcagttac aaactcaact    3000
ggttcagctc ttcctaaaat atctcacctc actgggacgg caacaatgtc acagaccaat    3060
agagacacgt ttaatgactc tgctgcaccc caaagcacaa cttggccaga gactagtccc    3120
agattcaaga cagggttacc ttcagcaaca accactgttt caacctctgc cacttctctc    3180
tctgctactg taatggtctc taaattcact tctccagcaa ctagttccat ggaagcaact    3240
tctatcaggg aaccatcaac aaccatcctc acaacagaga ccacgaatgg cccaggctct    3300
atggctgtgg cttctaccaa catcccaatt ggaaagggct acattactga aggaagattg    3360
gacacaagcc atctgcccat tggaaccaca gcttcctctg agacatctat ggattttacc    3420
atggccaaag aaagtgtctc aatgtcagta tctccatctc agtccatgga tgctgctggc    3480
tcaagcactc caggaaggac aagccaattc gttgacacat tttctgatga tgtctatcat    3540
ttaacatcca gagaaattac aatacctaga gatggaacaa gctcagctct gactccacaa    3600
atgactgcaa ctcaccctcc atctcctgat cctggctctg ctagaagcac ctggcttggc    3660
atcttgtcct catctccttc ttctcctact cccaaagtca caatgagctc acattttca    3720 actcagagag tcaccacaag catgataatg gacacagttg aaactagtcg gtggaacatg    3780
cccaacttac cttccacgac ttccttgaca ccaagtaata ttccaacaag tggtgccata    3840
ggaaaaagca ccctggttcc cttggacact ccatctccag ccacatcatt ggaggcatca    3900 gaaggggac ttccaacccct cagcacctac cctgaatcaa caaacacacc cagcatccac    3960
ctcggagcac acgctagttc agaaagtcca agcaccatca aacttaccat ggcttcagta    4020
gtaaaacctg gctcttacac acctctcacc ttccctcaa tagagaccca cattcatgta    4080
tcaacagcca gaatggctta ctcttctggg tcttcacctg agatgacagc tcctggagag    4140
actaacactg gtagtacctg gaccccacc acctacatca ccactacgga tcctaaggat    4200
acaagttcag ctcaggtctc tacaccccac tcagtgagga cactcagaac cacagaaaac    4260
catccaaaga cagagtccgc cacccccagct gcttactctg gaagtcctaa aatctcaagt    4320
tcacccaatc tcaccagtcc ggccacaaaa gcatggacca tcagacacac aactgaacac    4380
tccactcaat tacattacac aaaaattggca gaaaaatcat ctggatttga gacacagtca    4440
gctccaggac ctgtctctgt agtaatccct acctccccta ccattggaag cagcacattg    4500
gaactaactt ctgatgtccc agggggaacccc ctggtccttg ctcccagtga gcagaccaca    4560
```

```
atcactctcc ccatggcaac atggctgagt accagtttga cagaggaaat ggcttcaaca    4620
gaccttgata tttcaagtcc aagttcaccc atgagtacat ttgctatttt tccacctatg    4680
tccacacctt ctcatgaact ttcaaagtca gaggcagata ccagtgccat tagaaataca    4740
gattcaacaa cgttggatca gcacctagga atcaggagtt tgggcagaac tggggactta    4800
acaactgttc ctatcacccc actgacaacc acgtggacca gtgtgattga acactcaaca    4860
caagcacagg acacccttc tgcaacgatg agtcctactc acgtgacaca gtcactcaaa    4920
gatcaaacat ctataccagc ctcagcatcc ccttcccatc ttactgaagt ctaccctgag    4980
ctcgggacac aagggagaag ctcctctgag gcaaccactt tttggaaacc atctacagac    5040
acactgtcca gagagattga gactggccca acaaacattc aatccactcc acccatggac    5100
aacacaacaa cagggagcag tagtagtgga gtcaccctgg gcatagccca ccttcccata    5160
ggaacatcct ccccagctga acatccaca aacatggcac tggaaagaag aagttctaca    5220
gccactgtct ctatggctgg acaatggga ctccttgtta ctagtgctcc aggaagaagc    5280
atcagccagt cattaggaag agtttcctct gtcctttctg agtcaactac tgaaggagtc    5340
acagattcta gtaagggaag cagcccaagg ctgaacacac agggaaatac agctctctcc    5400
tcctctcttg aacccagcta tgctgaagga agccagatga gcacaagcat ccctctaacc    5460
tcatctccta caactcctga tgtggaattc atagggggca gcacattttg gaccaaggag    5520
gtcaccacag ttatgacctc agacatctcc aagtcttcag caaggacaga gtccagctca    5580 gctacccta tgtccacagc tttgggaagc actgaaaata caggaaaaga aaaactcaga    5640
actgcctcta tggatcttcc atctccaact ccatcaatgg aggtgacacc atggatttct    5700
ctcactctca gtaatgcccc caataccaca gattcacttg acctcagcca tggggtgcac    5760
accagctctg cagggacttt ggccactgac aggtcattga atactggtgt cactagagcc    5820
tccagattgg aaaacggctc tgatacctct tctaagtccc tgtctatggg aaacagcact    5880
cacacttcca tgacttacac agagaagagt gaagtgtctt cttcaatcca tcccgacct    5940 gagacctcag ctcctggagc agagaccact ttgacttcca ctcctggaaa cagggccata    6000
agcttaacat tgccttttc atccattcca gtggaagaag tcatttctac aggcataacc    6060
tcaggaccag acatcaactc agcacccatg acacattctc ccatcacccc accaacaatt    6120
gtatggacca gtacaggcac aattgaacag tccactcaac cactacatgc agtttcttca    6180
gaaaaagttt ctgtgcagac acagtcaact ccatatgtca actctgtggc agtgtctgct    6240 tccccctaccc atgagaattc agtctcttct ggaagcagca tcctctcc atattcctca    6300 gcctcacttg aatccttgga ttccacaatc agtaggagga atgcaatcac ttcctggcta    6360
tgggacctca ctacatctct ccccactaca acttggccaa gtactagttt atctgaggca    6420
ctgtcctcag gccattctgg ggtttcaaac ccaagttcaa ctacgactga atttccactc    6480
ttttcagctg catccacatc tgctgctaag caaagaaatc cagaaacaga gacccatggt    6540
ccccagaata cagccgcgag tactttgaac actgatgcat cctcggtcac aggtctttct    6600
gagactcctg tgggggcaag tatcagctct gaagtccctc ttccaatggc cataacttct    6660
agatcagatg tttctggcct tacatctgag agtactgcta acccgagttt aggcacagcc    6720
tcttcagcag ggaccaaatt aactaggaca atatccctgc ccacttcaga gtctttggtt    6780
tcctttagaa tgaacaagga tccatggaca gtgtcaatcc ctttggggtc ccatccaact    6840
actaatacag aaacaagcat cccagtaaac agcgcaggtc cacctggctt gtccacagta    6900
gcatcagatg taattgacac accttcagat ggggctgaga gtattcccac tgtctccttt    6960
```

```
tccccctccc ctgatactga agtgacaact atctcacatt tcccagaaaa gacaactcat    7020
tcatttagaa ccatttcatc tctcactcat gagttgactt caagagtgac acctattcct    7080
ggggattgga tgagttcagc tatgtctaca aagcccacag gagccagtcc ctccattaca    7140
ctgggagaga gaaggacaat cacctctgct gctccaacca cttcccccat agttctcact    7200
gctagtttca cagagaccag cacagtttca ctggataatg aaactacagt aaaaacctca    7260
gatatccttg acgcacggaa aacaaatgag ctcccctcag atagcagttc ttcttctgat    7320
ctgatcaaca cctccatagc ttcttcaact atggatgtca ctaaaacagc ctccatcagt    7380
cccactagca tctcaggaat gacagcaagt tcctccccat ctctcttctc ttcagataga    7440
ccccaggttc ccacatctac aacagagaca aatacagcca cctctccatc tgtttccagt    7500
aacacctatt ctcttgatgg gggctccaat gtgggtggca ctccatccac tttaccaccc    7560
tttacaatca cccaccctgt cgagacaagc tcggccctat agcctggtc tagaccagta    7620 agaactttca gcaccatggt cagcactgac actgcctccg gagaaaatcc tacctctagc    7680
aattctgtgg tgacttctgt tccagcacca ggtacatgga ccagtgtagg cagtactact    7740
gacttacctg ccatgggctt tctcaagaca agtcctgcag gagaggcaca ctcacttcta    7800
gcatcaacta ttgaaccagc cactgccttc actccccatc tctcagcagc agtggtcact    7860
ggatccagtg ctacatcaga agccagtctt ctcactacga gtgaaagcaa agccattcat    7920
tcttcaccac agaccccaac tacacccacc tctggagcaa actgggaaac ttcagctact    7980
cctgagagcc ttttggtagt cactgagact tcagacacaa cacttacctc aaagattttg    8040
gtcacagata ccatcttgtt ttcaactgtg tccacgccac cttctaaatt tccaagtacg    8100
gggactctgt ctggagcttc cttccctact ttactcccgg acactccagc catccctctc    8160
actgccactg agccaacaag ttcattagct acatcctttg attccacccc actggtgact    8220
atagcttcgg atagtcttgg cacagtccca gagactaccc tgaccatgtc agagacctca    8280
aatggtgatg cactggttct taagacagta agtaacccag ataggagcat ccctggaatc    8340
actatccaag gagtaacaga aagtccactc catccttctt ccacttcccc ctctaagatt    8400
gttgctccac ggaatacaac ctatgaaggt tcgatcacag tggcactttc tactttgcct    8460
gcgggaacta ctggttccct tgtattcagt cagagttctg aaaactcaga gacaacggct    8520
ttggtagact catcagctgg gcttgagagg gcatctgtga tgccactaac cacaggaagc    8580
cagggtatgg ctagctctgg aggaatcaga agtgggtcca ctcactcaac tggaaccaaa    8640
acattttctt ctctccctct gaccatgaac ccaggtgagg ttacagccat gtctgaaatc    8700
accacgaaca gactgacagc tactcaatca acagcaccca aagggatacc tgtgaagccc    8760
accagtgctg agtcaggcct cctaacacct gtctctgcct cctcaagccc atcaaaggcc    8820
tttgcctcac tgactacagc tcccccaact tgggggatcc cacagtctac cttgacattt    8880
gagttttctg aggtcccaag tttggatact aagtccgctt cttaccaac tcctggacag    8940 tccctgaaca ccattccaga ctcagatgca agcacagcat cttcctcact gtccaagtct    9000
ccagaaaaaa acccaagggc aaggatgatg acttccacaa aggccataag tgcaagctca    9060
tttcaatcaa caggttttac tgaaacccct gagggatctg cctcccttc tatggcaggg    9120 catgaaccca gagtccccac ttcaggaaca ggggaccta gatatgcctc agagagcatg    9180
tcttatccag acccagcaa ggcatcatca gctatgacat cgacctctct tgcatcaaaa    9240
ctcacaactc tcttcagcac aggtcaagca gcaaggtctg gttctagttc ctctcccata    9300
```

```
agcctatcca ctgagaaaga aacaagcttc ctttcccca ctgcatccac ctccagaaag    9360
acttcactat ttcttgggcc ttccatggca aggcagccca acatattggt gcatcttcag    9420
acttcagctc tgacactttc tccaacatcc actctaaata tgtcccagga ggagcctcct    9480
gagttaacct caagccagac cattgcagaa gaagagggaa caacagctga aacacagacg    9540
ttaaccttca caccatctga acccccaaca tccttgttac ctgtctcttc tcccacagaa    9600
cccacagcca gaagaaagag ttctccagaa acatgggcaa gctctatttc agttcctgcc    9660
aagacctcct tggttgaaac aactgatgga acgctagtga ccaccataaa gatgtcaagc    9720
caggcagcac aaggaaattc cacgtggcct gccccagcag aggagacggg gagcagtcca    9780
gcaggcacat ccccaggaag cccagaaatg tctaccactc tcaaaatcat gagctccaag    9840
gaacccagca tcagcccaga gatcaggtcc actgtgagaa attctccttg gaagactcca    9900
gaaacaactg ttcccatgga gaccacagtg gaaccagtca cccttcagtc cacagcccta    9960
ggaagtggca gcaccagcat ctctcacctg cccacaggaa ccacatcacc aaccaagtca   10020
ccaacagaaa atatgttggc tacagaaagg gtctccctct ccccatcccc acctgaggct   10080
tggaccaacc tttattctgg aactccagga gggaccaggc agtcactggc cacaatgtcc   10140
tctgtctccc tagagtcacc aactgctaga agcatcacag ggactggtca gcaaagcagt   10200
ccagaactgg tttcaaagac aactggaatg gaattctcta tgtggcatgg ctctactgga   10260
gggaccacag gggacacaca tgtctctctg agcacatctt ccaatatcct tgaagaccct   10320
gtaaccagcc caaactctgt gagctcattg acagataaat ccaaacataa aaccgagaca   10380
tgggtaagca ccacagccat tccctccact gtcctgaata taagataat ggcagctgaa   10440 caacagacaa gtcgatctgt ggatgaggct tattcatcaa ctagttcttg gtcagatcag   10500
acatctggga gtgacatcac ccttggtgca tctcctgatg tcacaaacac attatacatc   10560
acctccacag cacaaaccac ctcactagtg tctctgccct ctggagacca aggcattaca   10620
agcctcacca atccctcagg aggaaaaaca agctctgcgt catctgtcac atctccttca   10680
atagggcttg agactctgag ggccaatgta agtgcagtga aaagtgacat tgcccctact   10740
gctgggcatc tatctcagac ttcatctcct gcggaagtga gcatcctgga cgtaaccaca   10800
gctcctactc caggtatctc caccaccatc accaccatgg gaaccaactc aatctcaact   10860
accacaccca acccagaagt gggtatgagt accatggaca gcaccccggc cacagagagg   10920
cgcacaactt ctacagaaca cccttccacc tggtcttcca cagctgcatc agattcctgg   10980
actgtcacag acatgacttc aaacttgaaa gttgcaagat ctcctggaac aatttccaca   11040
atgcatacaa cttcattctt agcctcaagc actgaattag actccatgtc tactccccat   11100
ggccgtataa ctgtcattgg aaccagcctg tcactccat cctctgatgc ttcagctgta   11160
aagacagaga ccagtacaag tgaaagaaca ttgagtcctt cagacacaac tgcatctact   11220
cccatctcaa ctttttctcg tgtccagagg atgagcatct cagttcctga cattttaagt   11280
acaagttgga ctcccagtag tacagaagca gaagatgtgc ctgtttcaat ggtttctaca   11340
gatcatgcta gtacaaagac tgacccaaat acgcccctgt ccacttttct gtttgattct   11400
ctgtccactc ttgactggga cactgggaga tctctgtcat cagccacagc cactacctca   11460
gctcctcagg gggccacaac tccccaggaa ctcactttgg aaaccatgat cagcccagct   11520
acctcacagt tgcccttctc tatagggcac attacaagtg cagtcacacc agctgcaatg   11580
gcaaggagct ctggagttac tttttcaaga ccagatccca aagcaaaaaa ggcagagcag   11640
acttccactc agcttcccac caccacttct gcacatccag ggcaggtgcc cagatcagca   11700
```

```
gcaacaactc tggatgtgat cccacacaca gcaaaaactc cagatgcaac ttttcagaga   11760
caagggcaga cagctcttac aacagaggca agagctacat ctgactcctg gaatgagaaa   11820
gaaaaatcaa ccccaagtgc accttggatc actgagatga tgaattctgt ctcagaagat   11880
accatcaagg aggttaccag ctcctccagt gtattaagga ccctgaatac gctggacata   11940
aacttggaat ctgggacgac ttcatcccca agttggaaaa gcagcccata tgagagaatt   12000
gccccttctg agtccaccac agacaaagag gcaattcacc cttctacaaa cacagtagag   12060
accacaggct gggtcacaag ttccgaacat gcttctcatt ccactatccc agcccactca   12120
gcgtcatcca aactcacatc tccagtggtt acaacctcca ccagggaaca agcaatagtt   12180
tctatgtcaa caaccacatg gccagagtct acaagggcta aacagagcc taattccttc   12240 ttgactattg aactgaggga cgtcagccct tacatggaca ccagctcaac cacacaaaca   12300
agtattatct cttccccagg ttccactgcg atcaccaagg ggcctagaac agaaattacc   12360
tcctctaaga gaatatccag ctcattcctt gcccagtcta tgaggtcgtc agacagcccc   12420
tcagaagcca tcaccaggct gtctaacttt cctgccatga cagaatctgg aggaatgatc   12480
cttgctatgc aaacaagtcc acctggcgct acatcactaa gtgcacctac tttggataca   12540
tcagccacag cctcctggac agggactcca ctggctacga ctcagagatt tacatactca   12600
gagaagacca ctctctttag caaaggtcct gaggatacat cacagccaag ccctccctct   12660
gtggaagaaa ccagctcttc ctcttccctg gtacctatcc atgctacaac ctcgccttcc   12720
aatattttgt tgacatcaca agggcacagt ccctcctcta ctccacctgt gacctcagtt   12780
ttcttgtctg agacctctgg cctggggaag accacagaca tgtcgaggat aagcttggaa   12840
cctggcacaa gtttacctcc caatttgagc agtacagcag gtgaggcgtt atccacttat   12900
gaagcctcca gagatacaaa ggcaattcat cattctgcag acacagcagt gacgaatatg   12960
gaggcaacca gttctgaata ttctcctatc ccaggccata caaagccatc caaagccaca   13020
tctccattgg ttacctccca catcatgggg gacatcactt cttccacatc agtatttggc   13080
tcctccgaga ccacagagat tgagacagtg tcctctgtga accagggact tcaggagaga   13140
agcacatccc aggtggccag ctctgctaca gagacaagca ctgtcattac ccatgtgtct   13200
agtggtgatg ctactactca tgtcaccaag acacaagcca cttttctctag cggaacatcc   13260 atctcaagcc ctcatcagtt tataacttct accaacacat ttacagatgt gagcaccaac   13320
ccctccacct ctctgataat gacagaatct tcaggagtga ccatcaccac ccaaacaggt   13380
cctactggag ctgcaacaca gggtccatat ctcttggaca catcaaccat gccttacttg   13440
acagagactc cattagctgt gactccagat tttatgcaat cagagaagac cactctcata   13500
agcaaaggtc ccaaggatgt gtcctggaca agccctccct ctgtggcaga aaccagctat   13560
ccctcttccc tgacaccttt cttggtcaca accatacctc ctgccacttc cacgttacaa   13620
gggcaacata catcctctcc tgtttctgcg acttcagttc ttacctctgg actggtgaag   13680
accacagata tgttgaacac aagcatggaa cctgtgacca attcacctca aaatttgaac   13740
aatccatcaa atgagatact ggccactttg gcagccacca cagatataga gactattcat   13800
ccttccataa acaaagcagt gaccaatatg gggactgcca gttcagcaca tgtactgcat   13860
tccactctcc cagtcagctc agaaccatct acagccacat ctccaatggt tcctgcctcc   13920
agcatggggg acgctcttgc ttctatatca ataccttggtt ctgagaccac agacattgag   13980
ggagagccaa catcctccct gactgctgga cgaaaagaga acagcaccct ccaggagatg   14040
```

-continued

```
aactcaacta cagagtcaaa catcatcctc tccaatgtgt ctgtggggc tattactgaa    14100 gccacaaaaa tggaagtccc ctcttttgat gcaacattca taccaactcc tgctcagtca    14160
acaaagttcc cagatatttt ctcagtagcc agcagtagac tttcaaactc tcctcccatg    14220
acaatatcta cccacatgac caccacccag acagggtctt ctggagctac atcaaagatt    14280
ccacttgcct tagacacatc aaccttggaa acctcagcag ggactccatc agtggtgact    14340 gagggtttg cccactcaaa ataaccact gcaatgaaca atgatgtcaa ggacgtgtca    14400
cagacaaacc ctcccttca ggatgaagcc agctctccct cttctcaagc acctgtcctt    14460
gtcacaacct taccttcttc tgttgctttc acaccgcaat ggcacagtac ctcctctcct    14520
gtttctatgt cctcagttct tacttcttca ctggtaaaga ccgcaggcaa ggtggataca    14580
agcttagaaa cagtgaccag ttccctcaa agtatgagca cactttgga tgacatatcg    14640 gtcacttcag cagccaccac agatatagag acaacgcatc cttccataaa cacagtagtt    14700
accaatgtgg ggaccaccgg ttcagcattt gaatcacatt ctactgtctc agcttaccca    14760
gagccatcta aagtcacatc tccaaatgtt accacctcca ccatggaaga caccacaatt    14820
tccagatcaa tacctaaatc ctctaagact acaagaactg agactgagac aacttcctcc    14880
ctgactccta aactgaggga gaccagcatc tcccaggaga tcacctcgtc cacagagaca    14940
agcactgttc cttacaaaga gctcactggt gccactaccg aggtatccag gacagatgtc    15000
acttcctcta gcagtacatc cttccctggc cctgatcagt ccacagtgtc actagacatc    15060
tccacagaaa ccaacaccag gctgtctacc tccccaataa tgacagaatc tgcagaaata    15120
accatcacca cccaaacagg tcctcatggg gctacatcac aggatacttt taccatggac    15180
ccatcaaata caacccccca ggcagggatc cactcagcta tgactcatgg attttcacaa    15240
ttggatgtga ccactcttat gagcagaatt ccacaggatg tatcatggac aagtcctccc    15300
tctgtggata aaaccagctc cccctcttcc tttctgtcct cacctgcaat gaccacacct    15360
tccctgattt cttctacctt accagaggat aagctctcct ctcctatgac ttcacttctc    15420
acctctggcc tagtgaagat tacagacata ttacgtacac gcttggaacc tgtgaccagc    15480
tcacttccaa atttcagcag cacctcagat aagatactgg ccacttctaa agacagtaaa    15540
gacacaaagg aaattttcc ttctataaac acagaagaga ccaatgtgaa gccaacaac    15600 tctggacatg aatcccattc ccctgcactg gctgactcag agacacccaa agccacaact    15660
caaatggtta tcaccaccac tgtgggagat ccagctcctt ccacatcaat gccagtgcat    15720
ggttcctctg agactacaaa cattaagaga gagccaacat atttcttgac tcctagactg    15780
agagagacca gtacctctca ggagtccagc tttcccacgg acacaagttt tctactttcc    15840
aaagtcccca ctggtactat tactgaggtc tccagtacag gggtcaactc ttctagcaaa    15900
atttccaccc cagaccatga taagtccaca gtgccacctg acaccttcac aggagagatc    15960
cccagggtct tcacctcctc tattaagaca aaatctgcag aaatgacgat caccacccaa    16020
gcaagtcctc ctgagtctgc atcgcacagt acccttccct tggacacatc aaccacactt    16080
tcccagggag ggactcattc aactgtgact cagggattcc catactcaga ggtgaccact    16140
ctcatgggca tgggtcctgg aatgtgtca tggatgacaa ctccccctgt ggaagaaacc    16200
agctctgtgt cttccctgat gtcttcacct gccatgacat cccttctcc tgtttcctcc    16260 acatcaccac agagcatccc ctcctctcct cttcctgtga ctgcacttcc tacttctgtt    16320
ctggtgacaa ccacagatgt gttgggcaca acaagcccag agtctgtaac cagttcacct    16380
ccaaatttga gcagcatcac tcatgagaga ccggccactt acaaagacac tgcacacaca    16440
```

```
gaagccgcca tgcatcattc cacaaacacc gcagtgacca atgtagggac ttccgggtct    16500
ggacataaat cacaatcctc tgtcctagct gactcagaga catcgaaagc cacacctctg    16560
atgagtacca cctccaccct gggggacaca agtgtttcca catcaactcc taatatctct    16620
cagactaacc aaattcaaac agagccaaca gcatccctga gccctagact gagggagagc    16680
agcacgtctg agaagaccag ctcaacaaca gagacaaata ctgccttttc ttatgtgccc    16740
acaggtgcta ttactcaggc ctccagaaca gaaatctcct ctagcagaac atccatctca    16800
gaccttgatc ggcccacaat agcacccgac atctccacag gaatgatcac caggctcttc    16860
acctccccca tcatgacaaa atctgcagaa atgaccgtca ccactcaaac aactactcct    16920
ggggctacat cacagggtat ccttccctgg acacatcaa ccacactttt ccagggaggg     16980
actcattcaa ccgtgtctca ggattccca cactcagaga taaccactct tcggagcaga     17040 accctggag atgtgtcatg gatgacaact cccctgtgg aagaaaccag ctctgggttt      17100
tccctgatgt caccttccat gacatcccct tctcctgttt cctccacatc accagagagc    17160
atcccctcct ctcctctccc tgtgactgca cttcttactt ctgttctggt gacaaccaca    17220
aatgtattgg gcacaacaag cccagagccc gtaacgagtt caccctccaaa tttaagcagc   17280 cccacacagg agagactgac cacttacaaa gacactgcgc acacagaagc catgcatgct    17340
tccatgcata caaacactgc agtggccaac gtggggacct ccatttctgg acatgaatca    17400
caatcttctg tcccagctga ttcacacaca tccaaagcca catctccaat gggtatcacc    17460
ttcgccatgg gggatacaag tgtttctaca tcaactcctg ccttctttga gactagaatt    17520
cagactgaat caacatcctc tttgattcct ggattaaggg acaccaggac gtctgaggag    17580
atcaacactg tgacagagac cagcactgtc ctttcagaag tgcccactac tactactact    17640
gaggtctcca ggacagaagt tatcacttcc agcagaacaa ccatctcagg gcctgatcat    17700
tccaaaatgt caccctacat ctccacagaa accatcacca ggctctccac ttttcctttt    17760
gtaacaggat ccacagaaat ggccatcacc aaccaaacag gtcctatagg gactatctca    17820
caggctaccc ttaccctgga cacatcaagc acagcttcct gggaagggac tcactcacct    17880
gtgactcaga gatttccaca ctcagaggag accactacta tgagcagaag tactaagggc    17940
gtgtcatggc aaagccctcc ctctgtggaa gaaaccagtt ctccttcttc cccagtgcct    18000
ttacctgcaa taacctcaca ttcatctctt tattccgcag tatcaggaag tagccccact    18060
tctgctctcc ctgtgacttc ccttctcacc tctggcagga ggaagaccat agacatgttg    18120
gacacacact cagaacttgt gaccagctcc ttaccaagtg caagtagctt ctcaggtgag    18180
atactcactt ctgaagcctc cacaaataca gagacaattc actttcaga gaacacagca     18240 gaaaccaata tggggaccac caattctatg cataaactac attcctctgt ctcaatccac    18300
tcccagccat ccggacacac acctccaaag gttactggat ctatgatgga ggacgctatt    18360
gtttccacat caacacctgg ttctcctgag actaaaaatg ttgacagaga ctcaacatcc    18420
cctctgactc ctgaactgaa agaggacagc accgccctgg tgatgaactc aactacagag    18480
tcaaacactg ttttctccag tgtgtccctg gatgctgcta ctgaggtctc cagggcagaa    18540
gtcacctact atgatcctac attcatgcca gcttctgctc agtcaacaaa gtccccagac    18600
atttcacctg aagccagcag cagtcattct aactctcctc ccttgacaat atctacacac    18660
aagaccatcg ccacacaaac aggtccttct ggggtgacat ctcttggcca actgaccctg    18720
gacacatcaa ccatagccac ctcagcagga actccatcag ccagaactca ggattttgta    18780
```

-continued

```
gattcagaaa caaccagtgt catgaacaat gatctcaatg atgtgttgaa gacaagccct    18840
ttctctgcag aagaagccaa ctctctctct tctcaggcac ctctccttgt gcaaacctca    18900
ccttctcctg taacttccac attgcaagag cacagtacct cctctcttgt ttctgtgacc    18960
tcagtaccca cccctacact ggcgaagatc acagacatgg acacaaactt agaacctgtg    19020
actcgttcac ctcaaaattt aaggaacacc ttggccactt cagaagccac cacagataca    19080
cacacaatgc atccttctat aaacacagca gtggccaatg tggggaccac cagttcacca    19140
aatgaattct attttactgt ctcacctgac tcagacccat ataaagccac atccgcagta    19200
gttatcactt ccacctcggg ggactcaata gtttccacat caatgcctag atcctctgcg    19260
atgaaaaaga ttgagtctga gacaactttc tccctgatat ttagactgag ggagactagc    19320
acctcccaga aaattggctc atcctcagac acaagcacgg tctttgacaa agcattcact    19380
gctgctacta ctgaggtctc cagaacagaa ctcacctcct ctagcagaac atccatccaa    19440
ggcactgaaa agcccacaat gtcaccggac acctccacaa gatctgtcac catgctttct    19500
acttttgctg gcctgacaaa atccgaagaa aggaccattg ccacccaaac aggtcctcat    19560
agggcgacat cacagggtac ccttacctgg gacacatcaa tcacaacctc acaggcaggg    19620
acccactcag ctatgactca tggattttca caattagatt tgtccactct tacgagtaga    19680
gttcctgagt acatatcagg acaagcccca ccctctgtgg aaaaaaccag ctcttcctct    19740
tcccttctgt ctttaccagc aataacctca ccgtcccctg tacctactac attaccagaa    19800
agtaggccgt cttctcctgt tcatctgact tcactcccca cctctggcct agtgaagacc    19860
acagatatgc tggcatctgt ggccagttta cctccaaact tgggcagcac ctcacataag    19920
ataccgacta cttcagaaga cattaaagat acagagaaaa tgtatccttc cacaaacata    19980
gcagtaacca atgtggggac caccacttct gaaaaggaat cttattcgtc tgtcccagcc    20040
tactcagaac cacccaaagt cacctctcca atggttacct ctttcaacat aagggacacc    20100
attgttttcca catccatgcc tggctcctct gagattacaa ggattgagat ggagtcaaca    20160
ttctccctgg ctcatgggct gaagggaacc agcacctccc aggacccat cgtatccaca    20220
gagaaaagtg ctgtccttca caagttgacc actggtgcta ctgagacctc taggacagaa    20280
gttgcctctt ctagaagaac atccattcca ggccctgatc attccacaga gtcaccagac    20340
atctccactg aagtgatccc cagcctgcct atctcccttg gcattacaga atcttcaaat    20400
atgaccatca tcactcgaac aggtcctcct cttggctcta catcacaggg cacatttacc    20460
ttggacacac caactacatc ctccagggca ggaacacact cgatggcgac tcaggaattt    20520
ccacactcag aaatgaccac tgtcatgaac aaggaccctg agattctatc atggacaatc    20580
cctccttcta tagagaaaac cagcttctcc tcttccctga tgccttcacc agccatgact    20640
tcacctcctg tttcctcaac attaccaaag accattcaca ccactccttc tcctatgacc    20700
tcactgctca ccccctagcct agtgatgacc acagacacat gggcacaag cccagaacct    20760
acaaccagtt cacctccaaa tttgagcagt acctcacatg agatactgac aacagatgaa    20820
gacaccacag ctatagaagc catgcatcct tccacaagca cagcagcgac taatgtggaa    20880
accaccagtt ctggacatgg gtcacaatcc tctgtcctag ctgactcaga aaaaaccaag    20940
gccacagctc caatggatac cacctccacc atggggcata caactgtttc cacatcaatg    21000
tctgtttcct ctgagactac aaaaattaag agagagtcaa catattcctt gactcctgga    21060
ctgagagaga ccagcatttc ccaaaatgcc agcttttcca ctgacacaag tattgttctt    21120
tcagaagtcc ccactggtac tactgctgag gtctccagga cagaagtcac ctcctctggt    21180
```

```
agaacatcca tccctggccc ttctcagtcc acagttttgc cagaaatatc cacaagaaca   21240
atgacaaggc tctttgcctc gcccaccatg acagaatcag cagaaatgac catccccact   21300
caaacaggtc cttctgggtc tacctcacag gataccctta ccttggacac atccaccaca   21360
aagtcccagg caaagactca ttcaactttg actcagagat ttccacactc agagatgacc   21420
actctcatga gcagaggtcc tggagatatg tcatggcaaa gctctccctc tctggaaaat   21480
cccagctctc tccttccct gctgtcttta cctgccacaa cctcacctcc tcccatttcc   21540
tccacattac cagtgactat ctcctcctct cctcttcctg tgacttcact tctcacctct   21600
agcccggtaa cgaccacaga catgttacac acaagcccag aacttgtaac cagttcacct   21660
ccaaagctga gccacacttc agatgagaga ctgaccactg gcaaggacac cacaaataca   21720
gaagctgtgc atccttccac aaacacagca gcgtccaatg tggagattcc cagctctgga   21780
catgaatccc cttcctctgc cttagctgac tcagagacat ccaaagccac atcaccaatg   21840
tttattacct ccacccagga ggatacaact gttgccatat caaccctca cttcttggag   21900 actagcagaa ttcagaaaga gtcaatttcc tccctgagcc ctaaattgag ggagacaggc   21960
agttctgtgg agacaagctc agccatagag acaagtgctg tcctttctga agtgtccatt   22020
ggtgctacta ctgagatctc caggacagaa gtcacctcct ctagcagaac atccatctct   22080
ggttctgctg agtccacaat gttgccagaa atatccacca caagaaaaat cattaagttc   22140
cctacttccc ccatcctggc agaatcatca gaaatgacca tcaagaccca aacaagtcct   22200
cctgggtcta catcagagag taccttaca ttagacacat caaccactcc ctccttggta   22260
ataacccatt cgactatgac tcagagattg ccacactcag agataaccac tcttgtgagt   22320
agaggtgctg gggatgtgcc acggcccagc tctctccctg tggaagaaac aagccctcca   22380
tcttcccagc tgtctttatc tgccatgatc tcaccttctc ctgtttcttc cacattacca   22440
gcaagtagcc actcctcttc tgcttctgtg acttcacttc tcacaccagg ccaagtgaag   22500
actactgagg tgttggacgc aagtgcagaa cctgaaacca gttcacctcc aagtttgagc   22560
agcacctcag ttgaaatact ggccacctct gaagtcacca cagatacgga gaaaattcat   22620
cctttctcaa acacggcagt aaccaaagtt ggaacttcca gttctggaca tgaatcccct   22680
tcctctgtcc tacctgactc agagacaacc aaagccacat cggcaatggg taccatctcc   22740
attatggggg atacaagtgt ttctacatta actcctgcct tatctaacac taggaaaatt   22800
cagtcagagc cagcttcctc actgaccacc agattgaggg agaccagcac ctctgaagag   22860
accagcttag ccacagaagc aaacactgtt ctttctaaag tgtccactgg tgctactact   22920
gaggtctcca ggacagaagc catctccttt agcagaacat ccatgtcagg ccctgagcag   22980
tccacaatgt cacaagacat ctccatagga accatcccca ggatttctgc ctcctctgtc   23040
ctgacagaat ctgcaaaaat gaccatcaca acccaaacag gtccttcgga gtctacacta   23100
gaaagtaccc ttaatttgaa cacagcaacc acacctctt gggtggaaac ccactctata   23160
gtaattcagg gatttccaca cccagagatg accacttcca tgggcagagg tcctggaggt   23220
gtgtcatggc ctagccctcc ctttgtgaaa gaaaccagcc ctccatcctc cccgctgtct   23280
ttacctgccg tgacctcacc tcatcctgtt tccaccacat tcctagcaca tatccccccc   23340
tctccccttc ctgtgacttc acttctcacc tctggcccgg cgacaaccac agatatcttg   23400
ggtacaagca cagaacctgg aaccagttca tcttcaagtt tgagcaccac ctcccatgag   23460
agactgacca cttacaaaga cactgcacat acagaagccg tgcatccttc cacaaacaca   23520
```

```
ggagggacca atgtggcaac caccagctct ggatataaat cacagtcctc tgtcctagct   23580
gactcatctc caatgtgtac cacctccacc atgggggata caagtgttct cacatcaact   23640
cctgccttcc ttgagactag gaggattcag acagagctag cttcctccct gaccCctgga   23700
ttgagggagt ccagcggctc tgaagggacc agctcaggca ccaagatgag cactgtcctc   23760
tctaaagtgc ccactggtgc tactactgag atctccaagg aagacgtcac ctccatccca   23820
ggtcccgctc aatccacaat atccacgac atctccacaa gaaccgtcag ctggttctct   23880
acatcccctg tcatgacaga atcagcagaa ataaccatga cacccatac aagtccttta   23940 ggggccacaa cacaaggcac cagtactttg gacacgtcaa gcacaacctc tttgacaatg   24000
acacactcaa ctatatctca aggattttca cactcacaga tgagcactct tatgaggagg   24060
ggtcctgagg atgtatcatg gatgagccct ccccttctgg aaaaaactag accttccttt   24120
tctctgatgt cttcaccagc cacaacttca ccttctcctg tttcctccac attaccagag   24180
agcatctctt cctctcctct tcctgtgact tcactcctca cgtctggctt ggcaaaaact   24240
acagatatgt tgcacaaaag ctcagaacct gtaaccaact cacctgcaaa tttgagcagc   24300
acctcagttg aaatactggc cacctctgaa gtcaccacag atacagagaa aactcatcct   24360
tcttcaaaca gaacagtgac cgatgtgggg acctccagtt ctggacatga atccacttcc   24420
tttgtcctag ctgactcaca gacatccaaa gtcacatctc caatggttat tacctccacc   24480
atggaggata cgagtgtctc cacatcaact cctggctttt ttgagactag cagaattcag   24540
acagaaccaa catcctccct gacccttgga ctgagaaaga ccagcagctc tgagggacc    24600 agcttagcca cagagatgag cactgtcctt tctggagtgc ccactggtgc cactgctgaa   24660
gtctccagga cagaagtcac ctcctctagc agaacatcca tctcaggctt tgctcagctc   24720
acagtgtcac cagagacttc cacagaaacc atcaccagac tccctacctc cagcataatg   24780
acagaatcag cagaaatgat gatcaagaca caaacagatc ctcctgggtc tacaccagag   24840
agtactcata ctgtggacat atcaacaaca cccaactggg tagaaaccca ctcgactgtg   24900
actcagagat tttcacactc agagatgacc actcttgtga gcagaagccc tggtgatatg   24960
ttatggccta gtcaatcctc tgtggaagaa accagctctg cctcttccct gctgtctctg   25020
cctgccacga cctcaccttc tcctgtttcc tctacattag tagaggattt cccttccgct   25080
tctcttcctg tgacttctct tctcaaccct ggcctggtga taaccacaga caggatgggc   25140
ataagcagag aacctggaac cagttccact tcaaatttga gcagcacctc ccatgagaga   25200
ctgaccactt tggaagacac tgtagataca gaagacatgc agccttccac acacacagca   25260
gtgaccaacg tgaggacctc catttctgga catgaatcac aatcttctgt cctatctgac   25320
tcagagacac ccaaagccac atctccaatg ggtaccacct acaccatggg ggaaacgagt   25380
gtttccatat ccacttctga cttctttgag accagcagaa ttcagataga accaacatcc   25440
tccctgactt ctggattgag ggagaccagc agctctgaga ggatcagctc agccacagag   25500
ggaagcactg tcctttctga agtgcccagt ggtgctacca ctgaggtctc caggacagaa   25560
gtgatatcct ctaggggaac atccatgtca gggcctgatc agttcaccat atcaccagac   25620
atctctactg aagcgatcac caggctttct acttccccca ttatgacaga atcagcagaa   25680
agtgccatca ctattgagac aggttctcct ggggctacat cagagggtac cctcacctTg   25740
gacacctcaa caacaacctt ttggtcaggg acccactcaa ctgcatctcc aggattttca   25800
cactcagaga tgaccactct tatgagtaga actcctggag atgtgccatg gccgagcctt   25860
ccctctgtgg aagaagccag ctctgtctct tcctcactgt cttcacctgc catgacctca   25920
```

| | | | |
|---|---|---|---|
| acttcttttt | tctccacatt | accagagagc atctcctcct | ctcctcatcc tgtgactgca | 25980 |
| cttctcaccc | ttggcccagt | gaagaccaca gacatgttgc | gcacaagctc agaacctgaa | 26040 |
| accagttcac | ctccaaattt | gagcagcacc tcagctgaaa | tattagccac gtctgaagtc | 26100 |
| accaaagata | gagagaaaat | tcatccctcc tcaaacacac | ctgtagtcaa tgtagggact | 26160 |
| gtgatttata | aacatctatc | cccttcctct gttttggctg | acttagtgac aacaaaaccc | 26220 |
| acatctccaa | tggctaccac | ctccactctg gggaatacaa | gtgtttccac atcaactcct | 26280 |
| gccttcccag | aaactatgat | gacacagcca acttcctccc | tgacttctgg attaagggag | 26340 |
| atcagtacct | ctcaagagac | cagctcagca acagagagaa | gtgcttctct ttctggaatg | 26400 |
| cccactggtg | ctactactaa | ggtctccaga acagaagccc | tctccttagg cagaacatcc | 26460 |
| accccaggtc | ctgctcaatc | cacaatatca ccagaaatct | ccacggaaac catcactaga | 26520 |
| atttctactc | ccctcaccac | gacaggatca gcagaaatga | ccatcacccc caaaacaggt | 26580 |
| cattctgggg | catcctcaca | aggtaccttt accttggaca | catcaagcag agcctcctgg | 26640 |
| ccaggaactc | actcagctgc | aactcacaga tctccacact | cagggatgac cactcctatg | 26700 |
| agcagaggtc | ctgaggatgt | gtcatggcca agccgcccat | cagtggaaaa aactagccct | 26760 |
| ccatcttccc | tggtgtcttt | atctgcagta acctcacctt | cgccacttta ttccacacca | 26820 |
| tctgagagta | gccactcatc | tcctctccgg gtgacttctc | ttttcacccc tgtcatgatg | 26880 |
| aagaccacag | acatgttgga | cacaagcttg gaacctgtga | ccacttcacc tcccagtatg | 26940 |
| aatatcacct | cagatgagag | tctggccact tctaaagcca | ccatggagac agaggcaatt | 27000 |
| cagcttttcag | aaaacacagc | tgtgactcag atgggcacca | tcagcgctag acaagaattc | 27060 |
| tattcctctt | atccaggcct | cccagagcca tccaaagtga | catctccagt ggtcacctct | 27120 |
| tccaccataa | aagacattgt | ttctacaacc atacctgctt | cctctgagat aacaagaatt | 27180 |
| gagatggagt | caacatccac | cctgaccccc acaccaaggg | agaccagcac ctcccaggag | 27240 |
| atccactcag | ccacaaagcc | aagcactgtt ccttacaagg | cactcactag tgccacgatt | 27300 |
| gaggactcca | tgacacaagt | catgtcctct agcagaggac | ctagccctga tcagtccaca | 27360 |
| atgtcacaag | acatatccac | tgaagtgatc accaggctct | ctacctcccc catcaagaca | 27420 |
| gaatctacag | aaatgaccat | taccacccaa acaggttctc | ctggggctac atcaaggggt | 27480 |
| acccttacct | tggacacttc | aacaactttt atgtcaggga | cccactcaac tgcatctcaa | 27540 |
| ggattttcac | actcacagat | gaccgctctt atgagtagaa | ctcctggaga tgtgccatgg | 27600 |
| ctaagccatc | cctctgtgga | agaagccagc tctgcctctt | tctcactgtc ttcacctgtc | 27660 |
| atgacctcat | cttctcccgt | ttcttccaca ttaccagaca | gcatccactc ttcttcgctt | 27720 |
| cctgtgacat | cacttctcac | ctcagggctg gtgaagacca | cagagctgtt gggcacaagc | 27780 |
| tcagaacctg | aaaccagttc | accccccaaat ttgagcagca | cctcagctga atactggcc | 27840 |
| atcactgaag | tcactacaga | tacagagaaa ctggagatga | ccaatgtggt aacctcaggt | 27900 |
| tatacacatg | aatctccttc | ctctgtccta gctgactcag | tgacaacaaa ggccacatct | 27960 |
| tcaatgggta | tcacctaccc | cacaggagat acaaatgttc | tcacatcaac ccctgccttc | 28020 |
| tctgacacca | gtaggattca | aacaaagtca agctctcac | tgactcctgg gttgatggag | 28080 |
| accagcatct | ctgaagagac | cagctctgcc acagaaaaaa | gcactgtcct ttctagtgtg | 28140 |
| cccactggtg | ctactactga | ggtctccagg acagaagcca | tctcttctag cagaacatcc | 28200 |
| atcccaggcc | ctgctcaatc | cacaatgtca tcagacacct | ccatggaaac catcactaga | 28260 |

```
atttctaccc ccctcacaag gaaagaatca acagacatgg ccatcacccc caaaacaggt   28320
ccttctgggg ctacctcgca gggtaccttt accttggact catcaagcac agcctcctgg   28380
ccaggaactc actcagctac aactcagaga tttccacagt cagtggtgac aactcctatg   28440
agcagaggtc ctgaggatgt gtcatggcca agcccgctgt ctgtggaaaa aaacagccct   28500
ccatcttccc tggtatcttc atcttcagta acctcacctt cgccacttta ttccacacca   28560
tctgggagta gccactcctc tcctgtccct gtcacttctc ttttcacctc tatcatgatg   28620
aaggccacag acatgttgga tgcaagtttg aacctgaga ccacttcagc tcccaatatg   28680
aatatcacct cagatgagag tctggccgct tctaaagcca ccacggagac agaggcaatt   28740 cacgttttttg aaaatacagc agcgtcccat gtggaaacca ccagtgctac agaggaactc   28800
tattcctctt ccccaggctt ctcagagcca acaaaagtga tatctccagt ggtcacctct   28860
tcctctataa gagacaacat ggtttccaca acaatgcctg gctcctctgg cattacaagg   28920
attgagatag agtcaatgtc atctctgacc cctggactga gggagaccag aacctcccag   28980
gacatcacct catccacaga gacaagcact gtccttttaca agatgccctc tggtgccact   29040
cctgaggtct ccaggacaga agttatgccc tctagcagaa catccattcc tggccctgct   29100
cagtccacaa tgtcactaga catctccgat gaagttgtca ccaggctgtc tacctctccc   29160
atcatgacag aatctgcaga aataaccatc accacccaaa caggttattc tctggctaca   29220
tcccaggtta cccttccctt gggcacctca atgacctttt tgtcagggac ccactcaact   29280
atgtctcaag gactttcaca ctcagagatg accaatctta tgagcagggg tcctgaaagt   29340
ctgtcatgga cgagccctcg ctttgtggaa acaactagat cttcctcttc tctgacatca   29400
ttacctctca cgacctcact ttctcctgtg tcctccacat tactagacag tagcccctcc   29460
tctcctcttc ctgtgacttc acttatcctc ccaggcctgg tgaagactac agaagtgttg   29520
gatacaagct cagagcctaa aaccagttca tctccaaatt tgagcagcac ctcagttgaa   29580
ataccggcca cctctgaaat catgacagat acagagaaaa ttcatccttc ctcaaacaca   29640
gcggtggcca aagtgaggac ctccagttct gttcatgaat ctcattcctc tgtcctagct   29700
gactcagaaa caaccataac cataccttca atgggtatca cctccgctgt ggacgatacc   29760
actgttttca catcaaatcc tgccttctct gagactagga ggattccgac agagccaaca   29820
ttctcattga ctcctggatt cagggagact agcacctctg aagagaccac ctcaatcaca   29880
gaaacaagtg cagtcctta tggagtgccc actagtgcta ctactgaagt ctccatgaca   29940
gaaatcatgt cctctaatag aatacacatc cctgactctg atcagtccac gatgtctcca   30000
gacatcatca ctgaagtgat caccaggctc tcttcctcat ccatgatgtc agaatcaaca   30060
caaatgacca tcaccaccca aaaaagttct cctggggcta cagcacagag tactcttacc   30120
ttggccacaa caacagcccc cttggcaagg acccactcaa ctgttcctcc tagatttta   30180 cactcagaga tgacaactct tatgagtagg agtcctgaaa atccatcatg gaagagctct   30240
ctctttgtgg aaaaaactag ctcttcatct tctctgttgt ccttacctgt cacgacctca   30300
ccttctgttt cttccacatt accgcagagt atcccttcct cctctttttc tgtgacttca   30360
ctcctcaccc caggcatggt gaagactaca gacacaagca cagaacctgg aaccagttta   30420
tctccaaatc tgagtggcac ctcagttgaa atactggctg cctctgaagt caccacagat   30480
acagagaaaa ttcatccttc ttcaagcatg gcagtgacca atgtgggaac caccagttct   30540
ggacatgaac tatattcctc tgtttcaatc cactcggagc catccaaggc tacatacccca   30600 gtgggtactc cctcttccat ggctgaaacc tctatttcca catcaatgcc tgctaatttt   30660
```

```
gagaccacag gatttgaggc tgagccattt tctcatttga cttctggatt taggaagaca    30720
aacatgtccc tggacaccag ctcagtcaca ccaacaaata caccttcttc tcctgggtcc    30780
actcaccttt tacagagttc caagactgat ttcacctctt ctgcaaaaac atcatcccca    30840
gactggcctc cagcctcaca gtatactgaa attccagtgg acataatcac cccctttaat    30900
gcttctccat ctattacgga gtccactggg ataacctcct tcccagaatc caggtttact    30960
atgtctgtaa cagaaagtac tcatcatctg agtacagatt tgctgccttc agctgagact    31020
atttccactg gcacagtgat gccttctcta tcagaggcca tgacttcatt tgccaccact    31080
ggagttccac gagccatctc aggttcaggt agtccattct ctaggacaga gtcaggccct    31140
ggggatgcta ctctgtccac cattgcagag agcctgcctt catccactcc tgtgccattc    31200
tcctcttcaa ccttcactac cactgattct tcaaccatcc cagccctcca tgagataact    31260
tcctcttcag ctaccccata tagagtggac accagtcttg ggacagagag cagcactact    31320
gaaggacgct tggttatggt cagtactttg gacacttcaa gccaaccagg caggacatct    31380
tcatcaccca ttttggatac cagaatgaca gagagcgttg agctgggaac agtgacaagt    31440
gcttatcaag ttccttcact ctcaacacgg ttgacaagaa ctgatggcat tatggaacac    31500
atcacaaaaa tacccaatga agcagcacac agaggtacca taagaccagt caaaggccct    31560
cagacatcca cttcgcctgc cagtcctaaa ggactacaca caggagggac aaaaagaatg    31620
gagaccacca ccacagctct gaagaccacc accacagctc tgaagaccac ttccagagcc    31680
accttgacca ccagtgtcta tactcccact ttgggaacac tgactcccct caatgcatca    31740
atgcaaatgg ccagcacaat ccccacagaa atgatgatca cacccccata tgttttccct    31800
gatgttccag aaacgacatc ctcattggct accagcctgg gagcagaaac cagcacagct    31860
cttcccagga caacccccatc tgttttcaat agagaatcag agaccacagc ctcactggtc    31920
tctcgttctg gggcagagag aagtccggtt attcaaactc tagatgtttc ttctagtgag    31980
ccagatacaa cagcttcatg ggttatccat cctgcagaga ccatcccaac tgtttccaag    32040
acaaccccca ttttttttcca cagtgaatta gacactgtat cttccacagc caccagtcat    32100
ggggcagacg tcagctcagc cattccaaca aatatctcac ctagtgaact agatgcactg    32160
accccactgg tcactatttc ggggacagat actagtacaa cattcccaac actgactaag    32220
tccccacatg aaacagagac aagaaccaca tggctcactc atcctgcaga gaccagctca    32280
actattccca gaacaatccc caattttttct catcatgaat cagatgccac accttcaata    32340
gccaccagtc ctggggcaga aaccagttca gctattccaa ttatgactgt ctcacctggt    32400
gcagaagatc tggtgacctc acaggtcact agttctggga cagacagaaa tatgactatt    32460
ccaactttga ctctttctcc tggtgaacca aagacgatag cctcattagt cacccatcct    32520
gaagcacaga caagttcggc cattccaact tcaactatct cgcctgctgt atcacggttg    32580
gtgacctcaa tggtcaccag tttggcggca aagacaagta caactaatcg agctctgaca    32640
aactcccctg gtgaaccagc tacaacagtt tcattggtca cgcatcctgc acagaccagc    32700
ccaacagttc cctggacaac ttccattttt ttccatagta aatcagacac cacaccttca    32760
atgaccacca gtcatggggc agaatccagt tcagctgttc caactccaac tgtttcaact    32820
gaggtaccag gagtagtgac cccctttggtc accagttcta gggcagtgat cagtacaact    32880
attccaattc tgactctttc tcctggtgaa ccagagacca ccttcaat ggccaccagt    32940 catggggaag aagccagttc tgctattcca actccaactg tttcacctgg ggtaccagga    33000
```

```
gtggtgacct ctctggtcac tagttctagg gcagtgacta gtacaactat tccaattctg    33060 acttttctc ttggtgaacc agagaccaca ccttcaatgg ccaccagtca tgggacagaa     33120
gctggctcag ctgttccaac tgttttacct gaggtaccag gaatggtgac ctctctggtt    33180
gctagttcta gggcagtaac cagtacaact cttccaactc tgactctttc tcctggtgaa    33240
ccagagacca caccttcaat ggccaccagt catggggcag aagccagctc aactgttcca    33300
actgtttcac ctgaggtacc aggagtggtg acctctctgg tcactagttc tagtggagta    33360
aacagtacaa gtattccaac tctgattctt tctcctggtg aactagaaac cacaccttca    33420
atggccacca gtcatggggc agaagccagc tcagctgttc caactccaac tgtttcacct    33480
ggggtatcag gagtggtgac ccctctggtc actagttcca gggcagtgac cagtacaact    33540
attccaattc taactctttc ttctagtgag ccagagacca ccttcaat ggccaccagt     33600 catggggtag aagccagctc agctgttcta actgtttcac ctgaggtacc aggaatggtg    33660
acctctctgg tcactagttc tagagcagta accagtacaa ctattccaac tctgactatt    33720
tcttctgatg aaccagagac cacaacttca ttggtcaccc attctgaggc aaagatgatt    33780
tcagccattc caactttagc tgtctcccct actgtacaag gctggtgac ttcactggtc     33840 actagttctg ggtcagagac cagtgcgttt tcaaatctaa ctgttgcctc aagtcaacca    33900
gagaccatag actcatgggt cgctcatcct gggacagaag caagttctgt tgttccaact    33960
ttgactgtct ccactggtga gccgtttaca aatatctcat ggtcaccca tcctgcagag     34020 agtagctcaa ctcttcccag gacaacctca aggttttccc acagtgaatt agacactatg    34080
ccttctacag tcaccagtcc tgaggcagaa tccagctcag ccatttcaac aactatttca    34140
cctggtatac caggtgtgct gacatcactg gtcactagct ctgggagaga catcagtgca    34200
acttttccaa cagtgcctga gtccccacat gaatcagagg caacagcctc atgggttact    34260
catcctgcag tcaccagcac aacagttccc aggacaaccc ctaattattc tcatagtgaa    34320
ccagacacca caccatcaat agccaccagt cctggggcag aagccacttc agattttcca    34380
acaataactg tctcacctga tgtaccagat atggtaacct cacaggtcac tagttctggg    34440
acagacacca gtataactat tccaactctg actctttctt ctggtgagcc agagaccaca    34500
acctcattta tcacctattc tgagacacac acaagttcag ccattccaac tctccctgtc    34560
tcccctggtg catcaaagat gctgacctca ctggtcatca gttctgggac agacagcact    34620
acaactttcc caacactgac ggagacccca tatgaaccag agacaacagc catacagctc    34680
attcatcctg cagagaccaa cacaatggtt cccaggacaa ctcccaagtt ttcccatagt    34740
aagtcagaca ccacactccc agtagccatc accagtcctg ggccagaagc cagttcagct    34800
gtttcaacga caactatctc acctgatatg tcagatctgg tgacctcact ggtccctagt    34860
tctgggacag acaccagtac aaccttccca acattgagtg agaccccata tgaaccagag    34920
actacagcca cgtggctcac tcatcctgca gaaaccagca acggtttc tgggacaatt     34980 cccaactttt cccatagggg atcagacact gcaccctcaa tggtcaccag tcctggagta    35040
gacacgaggt caggtgttcc aactacaacc atcccaccca gtataccagg ggtagtgacc    35100
tcacaggtca ctagttctgc aacagacact agtacagcta ttccaacttt gactccttct    35160
cctggtgaac cagagaccac agcctcatca gctacccatc ctgggacaca gactggcttc    35220
actgttccaa ttcggactgt tccctctagt gagccagata caatggcttc ctgggtcact    35280
catcctccac agaccagcac acctgttccc agaacaacct ccagttttc ccatagtagt     35340 ccagatgcca cacctgtaat ggccaccagt cctaggacag aagccagttc agctgtactg    35400
```

| | | | | | |
|---|---|---|---|---|---|
| acaacaatct | cacctggtgc | accagagatg | gtgacttcac | agatcactag | ttctggggca | 35460 |
| gcaaccagta | caactgttcc | aactttgact | cattctcctg | gtatgccaga | gaccacagcc | 35520 |
| ttattgagca | cccatcccag | aacagagaca | agtaaaacat | ttcctgcttc | aactgtgttt | 35580 |
| cctcaagtat | cagagaccac | agcctcactc | accattagac | ctggtgcaga | gactagcaca | 35640 |
| gctctcccaa | ctcagacaac | atcctctctc | ttcaccctac | ttgtaactgg | aaccagcaga | 35700 |
| gttgatctaa | gtccaactgc | ttcacctggt | gtttctgcaa | aaacagcccc | actttccacc | 35760 |
| catccaggga | cagaaaccag | cacaatgatt | ccaacttcaa | ctctttccct | tggtttacta | 35820 |
| gagactacag | gcttactggc | caccagctct | cagcagaga | ccagcacgag | tactctaact | 35880 |
| ctgactgttt | cccctgctgt | ctctgggctt | tccagtgcct | ctataacaac | tgataagccc | 35940 |
| caaactgtga | cctcctggaa | cacagaaacc | tcaccatctg | taacttcagt | tggacccca | 36000 |
| gaattttcca | ggactgtcac | aggcaccact | atgaccttga | taccatcaga | gatgccaaca | 36060 |
| ccacctaaaa | ccagtcatgg | agaaggagtg | agtccaacca | ctatcttgag | aactacaatg | 36120 |
| gttgaagcca | ctaatttagc | taccacaggt | tccagtccca | ctgtggccaa | gacaacaacc | 36180 |
| accttcaata | cactggctgg | aagcctcttt | actcctctga | ccacacctgg | gatgtccacc | 36240 |
| ttggcctctg | agagtgtgac | ctcaagaaca | agttataacc | atcggtcctg | gatctccacc | 36300 |
| accagcagtt | ataaccgtcg | gtactggacc | cctgccacca | gcactccagt | gacttctaca | 36360 |
| ttctccccag | ggatttccac | atcctccatc | cccagctcca | cagcagccac | agtcccattc | 36420 |
| atggtgccat | tcaccctcaa | cttcaccatc | accaacctgc | agtacgagga | ggacatgcgg | 36480 |
| caccctggtt | ccaggaagtt | caacgccaca | gagagagaac | tgcagggtct | gctcaaaccc | 36540 |
| ttgttcagga | atagcagtct | ggaatacctc | tattcaggct | gcagactagc | ctcactcagg | 36600 |
| ccagagaagg | atagctcagc | cacggcagtg | gatgccatct | gcacacatcg | ccctgaccct | 36660 |
| gaagacctcg | gactgacag | agagcgactg | tactgggagc | tgagcaatct | gacaaatggc | 36720 |
| atccaggagc | tgggccccta | caccctggac | cggaacagtc | tctatgtcaa | tggtttcacc | 36780 |
| catcgaagct | ctatgcccac | caccagcact | cctgggacct | ccacagtgga | tgtgggaacc | 36840 |
| tcagggactc | catcctccag | ccccagcccc | acgactgctg | gccctctcct | gatgccgttc | 36900 |
| accctcaact | tcaccatcac | caacctgcag | tacgaggagg | acatgcgtcg | cactggctcc | 36960 |
| aggaagttca | acaccatgga | gagtgtcctg | cagggtctgc | tcaagccctt | gttcaagaac | 37020 |
| accagtgttg | gccctctgta | ctctggctgc | agattgacct | tgctcaggcc | cgagaaagat | 37080 |
| ggggcagcca | ctggagtgga | tgccatctgc | acccaccgcc | ttgaccccaa | aagccctgga | 37140 |
| ctcaacaggg | agcagctgta | ctgggagcta | agcaaactga | ccaatgacat | tgaagagctg | 37200 |
| ggccctaca | ccctggacag | gaacagtctc | tatgtcaatg | gtttcaccca | tcagagctct | 37260 |
| gtgtccacca | ccagcactcc | tgggacctcc | acagtggatc | tcagaacctc | agggactcca | 37320 |
| tcctccctct | ccagcccac | aattatggct | gctggccctc | tcctggtacc | attcacctc | 37380 |
| aacttcacca | tcaccaacct | gcagtatggg | gaggacatgg | gtcaccctgg | ctccaggaag | 37440 |
| ttcaacacca | cagagagggt | cctgcagggt | ctgcttggtc | ccatattcaa | gaacaccagt | 37500 |
| gttggccctc | tgtactctgg | ctgcagactg | acctctctca | ggtctgagaa | ggatggagca | 37560 |
| gccactggag | tggatgccat | ctgcatccat | catcttgacc | ccaaaagccc | tggactcaac | 37620 |
| agagagcggc | tgtactggga | gctgagccaa | ctgaccaatg | gcatcaaaga | gctgggcccc | 37680 |
| tacaccctgg | acaggaacag | tctctatgtc | aatggtttca | cccatcggac | ctctgtgccc | 37740 |

| | |
|---|---|
| accagcagca ctcctgggac ctccacagtg gaccttggaa cctcagggac tccattctcc | 37800 |
| ctcccaagcc ccgcaactgc tggccctctc ctggtgctgt tcaccctcaa cttcaccatc | 37860 |
| accaacctga agtatgagga ggacatgcat cgccctggct ccaggaagtt caacaccact | 37920 |
| gagagggtcc tgcagactct gcttggtcct atgttcaaga acaccagtgt tggccttctg | 37980 |
| tactctggct gcagactgac cttgctcagg tccgagaagg atggagcagc cactggagtg | 38040 |
| gatgccatct gcacccaccg tcttgacccc aaaagccctg gagtggacag ggagcagcta | 38100 |
| tactgggagc tgagccagct gaccaatggc atcaaagagc tgggcccta caccctggac | 38160 |
| aggaacagtc tctatgtcaa tggtttcacc cattggatcc ctgtgcccac cagcagcact | 38220 |
| cctgggacct ccacagtgga ccttgggtca gggactccat cctccctccc cagccccaca | 38280 |
| actgctggcc ctctcctggt gccgttcacc ctcaacttca ccatcaccaa cctgaagtac | 38340 |
| gaggaggaca tgcattgccc tggctccagg aagttcaaca ccacagagag agtcctgcag | 38400 |
| agtctgcttg gtcccatgtt caagaacacc agtgttggcc ctctgtactc tggctgcaga | 38460 |
| ctgaccttgc tcaggtccga aaggatgga gcagccactg gagtggatgc catctgcacc | 38520 |
| caccgtcttg accccaaaag cctggagtg gacagggagc agctatactg ggagctgagc | 38580 |
| cagctgacca atggcatcaa agagctgggt ccctacaccc tggacagaaa cagtctctat | 38640 |
| gtcaatggtt tcacccatca gacctctgcg cccaacacca gcactcctgg gacctccaca | 38700 |
| gtggaccttg ggacctcagg gactccatcc tccctcccca gcctacatc tgctggccct | 38760 |
| ctcctggtgc cattcaccct caacttcacc atcaccaacc tgcagtacga ggaggacatg | 38820 |
| catcacccag gctccaggaa gttcaacacc acggagcggg tcctgcaggg tctgcttggt | 38880 |
| cccatgttca gaacaccag tgtcggcctt ctgtactctg gctgcagact gaccttgctc | 38940 |
| aggcctgaga gaatgggc agccactgga atggatgcca tctgcagcca ccgtcttgac | 39000 |
| cccaaaagcc ctggactcaa cagagagcag ctgtactggg agctgagcca gctgacccat | 39060 |
| ggcatcaaag agctgggccc ctacaccctg gacaggaaca gtctctatgt caatggtttc | 39120 |
| acccatcgga gctctgtggc cccaccagc actcctggga cctccacagt ggaccttggg | 39180 |
| acctcaggga ctccatcctc cctcccagc cccacaacag ctgttcctct cctggtgccg | 39240 |
| ttcaccctca actttaccat caccaatctg cagtatgggg aggacatgcg tcaccctggc | 39300 |
| tccaggaagt tcaacaccac agagagggtc ctgcagggtc tgcttggtcc cttgttcaag | 39360 |
| aactccagtg tcggccctct gtactctggc tgcagactga tctctctcag gtctgagaag | 39420 |
| gatggggcag ccactggagt ggatgccatc tgcacccacc accttaaccc tcaaagccct | 39480 |
| ggactggaca gggagcagct gtactggcag ctgagccaga tgaccaatgg catcaaagag | 39540 |
| ctgggccccct acaccctgga ccggaacagt ctctacgtca atggtttcac ccatcggagc | 39600 |
| tctgggctca ccaccagcac tccttggact tccacagttg accttggaac ctcagggact | 39660 |
| ccatcccccg tccccagccc cacaaccacc ggccctctcc tggtgccatt cacactcaac | 39720 |
| ttcaccatca ctaacctaca gtatgaggag aacatgggtc accctggctc caggaagttc | 39780 |
| aacatcacgg agagtgttct gcagggtctg ctcaagccct tgttcaagag caccagtgtt | 39840 |
| ggccctctgt attctggctg cagactgacc ttgctcaggc ctgagaagga tggagtagcc | 39900 |
| accagagtgg acgccatctg cacccaccgc cctgacccca aaatccctgg gctagacaga | 39960 |
| cagcagctat actgggagct gagccagctg acccacagca tcactgagct gggaccctac | 40020 |
| accctggata gggacagtct ctatgtcaat ggttcacccc agcggagctc tgtgcccacc | 40080 |
| accagcactc ctgggacttt tcacagtacag ccggaaacct ctgagactcc atcatccctc | 40140 |

```
cctggcccca cagccactgg ccctgtcctg ctgccattca ccctcaattt taccatcact   40200
aacctgcagt atgaggagga catgcgtcgc cctggctcca ggaagttcaa caccacgag    40260
agggtccttc agggtctgct tatgcccttg ttcaagaaca ccagtgtcag ctctctgtac   40320
tctggttgca gactgacctt gctcaggcct gagaaggatg gggcagccac cagagtggat   40380
gctgtctgca cccatcgtcc tgaccccaaa agccctggac tggacagaga gcggctgtac   40440
tggaagctga gccagctgac ccacggcatc actgagctgg gccectacac cctggacagg   40500
cacagtctct atgtcaatgg tttcacccat cagagctcta tgacgaccac cagaactcct   40560
gatacctcca caatgcacct ggcaacctcg agaactccag cctccctgtc tggacccatg   40620
accgccagcc ctctcctggt gctattcaca attaacttca ccatcactaa cctgcggtat   40680
gaggagaaca tgcatcaccc tggctctaga aagtttaaca ccacggagag agtccttcag   40740
ggtctgctca ggcctgtgtt caagaacacc agtgttggcc ctctgtactc tggctgcaga   40800
ctgaccttgc tcaggcccaa gaaggatggg gcagccacca agtggatgc catctgcacc    40860
taccgccctg atcccaaaag ccctggactg gacagagagc agctatactg ggagctgagc   40920
cagctgaccc acagcatcac tgagctgggc cctacaccc tggacaggga cagtctctat    40980
gtcaatggtt tcacacagcg gagctctgtg cccaccacta gcattcctgg gaccccaca    41040
gtggacctgg gaacatctgg gactccagtt tctaaacctg gtccctcggc tgccagccct   41100
ctcctggtgc tattcactct caacttcacc atcaccaacc tgcggtatga ggagaacatg   41160
cagcaccctg gctccaggaa gttcaacacc acggagaggg tccttcaggg cctgctcagg   41220
tccctgttca agagcaccag tgttggccct ctgtactctg gctgcagact gactttgctc   41280
aggcctgaaa aggatgggac agccactgga gtggatgcca tctgcaccca ccaccctgac   41340
cccaaaagcc ctaggctgga cagagagcag ctgtattggg agctgagcca gctgacccac   41400
aatatcactg agctgggccc ctatgccctg acaacgaca gcctctttgt caatggtttc    41460
actcatcgga gctctgtgtc caccaccagc actcctggga cccccacagt gtatctggga   41520
gcatctaaga ctccagcctc gatatttggc ccttcagctg ccagccatct cctgatacta   41580
ttcaccctca acttcaccat cactaacctg cggtatgagg agaacatgtg gcctggctcc   41640
aggaagttca acactacaga gagggtcctt cagggcctgc taaggccctt gttcaagaac   41700
accagtgttg ccctctgta ctctggctgc aggctgacct tgctcaggcc agagaaagat    41760
ggggaagcca ccggagtgga tgccatctgc acccaccgcc ctgaccccac aggccctggg   41820
ctggacagag agcagctgta tttggagctg agccagctga cccacagcat cactgagctg   41880
ggcccctaca cactggacag ggacagtctc tatgtcaatg gtttcaccca tcggagctct   41940
gtacccacca ccagcaccgg ggtggtcagc gaggagccat tcacactgaa cttcaccatc   42000
aacaacctgc gctacatggc ggacatgggc caacccggct ccctcaagtt caacatcaca   42060
gacaacgtca tgcagcacct gctcagtcct ttgttccaga ggagcagcct gggtgcacgg   42120
tacacaggct gcagggtcat cgcactaagg tctgtgaaga acggtgctga gacacgggtg   42180
gacctcctct gcacctacct gcagcccctc agcggcccag gtctgcctat caagcaggtg   42240
ttccatgagc tgagccagca gacccatggc atcacccggc tgggccccta ctctctggac   42300
aaagacagcc tctaccttaa cggttacaat gaacctggtc cagatgagcc tcctacaact   42360
cccaagccag ccaccacatt cctgcctcct ctgtcagaag ccacaacagc catggggtac   42420
cacctgaaga ccctcacact caacttcacc atctccaatc tccagtattc accagatatg   42480
```

```
ggcaagggct cagctacatt caactccacc gaggggtcc ttcagcacct gctcagaccc    42540
ttgttccaga agagcagcat gggcccttc tacttgggtt gccaactgat ctccctcagg    42600
cctgagaagg atggggcagc cactggtgtg acaccacct gcacctacca ccctgaccct    42660
gtgggccccg ggctggacat acagcagctt tactgggagc tgagtcagct gacccatggt    42720
gtcacccaac tgggcttcta tgtcctggac agggatagcc tcttcatcaa tggctatgca    42780
ccccagaatt tatcaatccg gggcgagtac cagataaatt ccacattgt caactggaac    42840
ctcagtaatc cagaccccac atcctcagag tacatcaccc tgctgaggga catccaggac    42900
aaggtcacca cactctacaa aggcagtcaa ctacatgaca cattccgctt ctgcctggtc    42960
accaacttga cgatggactc cgtgttggtc actgtcaagg cattgttctc ctccaatttg    43020
gaccccagcc tggtggagca agtctttcta gataagaccc tgaatgcctc attccattgg    43080
ctgggctcca cctaccagtt ggtggacatc catgtgacag aaatggagtc atcagtttat    43140
caaccaacaa gcagctccag cacccagcac ttctacctga atttcaccat caccaaccta    43200
ccatattccc aggacaaagc ccagccaggc accaccaatt accagaggaa caaaaggaat    43260
attgaggatg cgctcaacca actcttccga aacagcagca tcaagagtta ttttttctgac    43320
tgtcaagttt caacattcag gtctgtcccc aacaggcacc acaccggggt ggactccctg    43380
tgtaacttct cgccactggc tcggagagta gacagagttg ccatctatga ggaatttctg    43440
cggatgaccc ggaatggtac ccagctgcag aacttcaccc tggacaggag cagtgtcctt    43500
gtggatgggt attctcccaa cagaaatgag cccttaactg ggaattctga ccttcccttc    43560
tgggctgtca tcctcatcgg cttggcagga ctcctgggag tcatcacatg cctgatctgc    43620
ggtgtcctgg tgaccacccg ccggcggaag aaggaaggag aatacaacgt ccagcaacag    43680
tgcccaggct actaccagtc acacctagac ctggaggatc tgcaatgact ggaacttgcc    43740
ggtgcctggg gtgcctttcc cccagccagg gtccaaagaa gcttggctgg ggcagaaata    43800
aaccatattg gtcgga                                                   43816
```

<210> SEQ ID NO 6
<211> LENGTH: 14507
<212> TYPE: PRT
<213> ORGANISM: Homo sapiens

<400> SEQUENCE: 6

```
Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Gln Ser Leu Gly
65                  70                  75                  80

Val Met Ser Ser Ala Leu Pro Glu Ser Thr Ser Arg Gly Met Thr His
            85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
```

-continued

```
            130                 135                 140
Ser Thr Tyr Thr Leu Thr Val Glu Thr Thr Ser Gly Pro Val Thr Glu
145                 150                 155                 160

Lys Tyr Thr Val Pro Thr Glu Thr Ser Thr Thr Glu Gly Asp Ser Thr
                165                 170                 175

Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
                195                 200                 205

Ser Met Thr Pro Ala Glu Thr Thr Val Thr Asp Ser His Thr Pro Gly
        210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
                260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
        290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
            355                 360                 365

Ala Phe Ala Glu Thr Met Asp Ile Pro Ser Thr His Ile Ala Lys Thr
        370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
        450                 455                 460

Asp Ser Lys Ile Arg Ser Pro Ser Gln Val Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
        515                 520                 525

Ser Glu Pro Gln His Thr Gln Trp Val Glu Thr Ser Pro Ser Met Lys
        530                 535                 540

Thr Glu Arg Pro Pro Ala Ser Ser Val Ala Ala Pro Ile Thr Thr
545                 550                 555                 560
```

-continued

```
Ser Val Pro Ser Val Val Ser Gly Phe Thr Thr Leu Lys Thr Ser Ser
                565                 570                 575
Thr Lys Gly Ile Trp Leu Glu Glu Thr Ser Ala Asp Thr Leu Ile Gly
            580                 585                 590
Glu Ser Thr Ala Gly Pro Thr Thr His Gln Phe Ala Val Pro Thr Gly
        595                 600                 605
Ile Ser Met Thr Gly Gly Ser Ser Thr Arg Gly Ser Gln Gly Thr Thr
    610                 615                 620
His Leu Leu Thr Arg Ala Thr Ala Ser Ser Glu Thr Ser Ala Asp Leu
625                 630                 635                 640
Thr Leu Ala Thr Asn Gly Val Pro Val Ser Val Ser Pro Ala Val Ser
                645                 650                 655
Lys Thr Ala Ala Gly Ser Ser Pro Pro Gly Gly Thr Lys Pro Ser Tyr
            660                 665                 670
Thr Met Val Ser Ser Val Ile Pro Glu Thr Ser Ser Leu Gln Ser Ser
        675                 680                 685
Ala Phe Arg Glu Gly Thr Ser Leu Gly Leu Thr Pro Leu Asn Thr Arg
    690                 695                 700
His Pro Phe Ser Ser Pro Glu Pro Asp Ser Ala Gly His Thr Lys Ile
705                 710                 715                 720
Ser Thr Ser Ile Pro Leu Leu Ser Ser Ala Ser Val Leu Glu Asp Lys
                725                 730                 735
Val Ser Ala Thr Ser Thr Phe Ser His His Lys Ala Thr Ser Ser Ile
            740                 745                 750
Thr Thr Gly Thr Pro Glu Ile Ser Thr Lys Thr Lys Pro Ser Ser Ala
        755                 760                 765
Val Leu Ser Ser Met Thr Leu Ser Asn Ala Ala Thr Ser Pro Glu Arg
    770                 775                 780
Val Arg Asn Ala Thr Ser Pro Leu Thr His Pro Ser Pro Ser Gly Glu
785                 790                 795                 800
Glu Thr Ala Gly Ser Val Leu Thr Leu Ser Thr Ser Ala Glu Thr Thr
                805                 810                 815
Asp Ser Pro Asn Ile His Pro Thr Gly Thr Leu Thr Ser Glu Ser Ser
            820                 825                 830
Glu Ser Pro Ser Thr Leu Ser Leu Pro Ser Val Ser Gly Val Lys Thr
        835                 840                 845
Thr Phe Ser Ser Ser Thr Pro Ser Thr His Leu Phe Thr Ser Gly Glu
    850                 855                 860
Glu Thr Glu Glu Thr Ser Asn Pro Ser Val Ser Gln Pro Glu Thr Ser
865                 870                 875                 880
Val Ser Arg Val Arg Thr Thr Leu Ala Ser Thr Ser Val Pro Thr Pro
                885                 890                 895
Val Phe Pro Thr Met Asp Thr Trp Pro Thr Arg Ser Ala Gln Phe Ser
            900                 905                 910
Ser Ser His Leu Val Ser Glu Leu Arg Ala Thr Ser Ser Thr Ser Val
        915                 920                 925
Thr Asn Ser Thr Gly Ser Ala Leu Pro Lys Ile Ser His Leu Thr Gly
    930                 935                 940
Thr Ala Thr Met Ser Gln Thr Asn Arg Asp Thr Phe Asn Asp Ser Ala
945                 950                 955                 960
Ala Pro Gln Ser Thr Thr Trp Pro Glu Thr Ser Pro Arg Phe Lys Thr
                965                 970                 975
```

```
Gly Leu Pro Ser Ala Thr Thr Thr Val Ser Thr Ser Ala Thr Ser Leu
            980                 985                 990

Ser Ala Thr Val Met Val Ser Lys Phe Thr Ser Pro Ala Thr Ser Ser
            995                 1000                1005

Met Glu Ala Thr Ser Ile Arg Glu Pro Ser Thr Thr Ile Leu Thr
        1010                1015                1020

Thr Glu Thr Thr Asn Gly Pro Gly Ser Met Ala Val Ala Ser Thr
        1025                1030                1035

Asn Ile Pro Ile Gly Lys Gly Tyr Ile Thr Glu Gly Arg Leu Asp
        1040                1045                1050

Thr Ser His Leu Pro Ile Gly Thr Thr Ala Ser Ser Glu Thr Ser
        1055                1060                1065

Met Asp Phe Thr Met Ala Lys Glu Ser Val Ser Met Ser Val Ser
        1070                1075                1080

Pro Ser Gln Ser Met Asp Ala Ala Gly Ser Ser Thr Pro Gly Arg
        1085                1090                1095

Thr Ser Gln Phe Val Asp Thr Phe Ser Asp Asp Val Tyr His Leu
        1100                1105                1110

Thr Ser Arg Glu Ile Thr Ile Pro Arg Asp Gly Thr Ser Ser Ala
        1115                1120                1125

Leu Thr Pro Gln Met Thr Ala Thr His Pro Ser Pro Asp Pro
        1130                1135                1140

Gly Ser Ala Arg Ser Thr Trp Leu Gly Ile Leu Ser Ser Ser Pro
        1145                1150                1155

Ser Ser Pro Thr Pro Lys Val Thr Met Ser Ser Thr Phe Ser Thr
        1160                1165                1170

Gln Arg Val Thr Thr Ser Met Ile Met Asp Thr Val Glu Thr Ser
        1175                1180                1185

Arg Trp Asn Met Pro Asn Leu Pro Ser Thr Thr Ser Leu Thr Pro
        1190                1195                1200

Ser Asn Ile Pro Thr Ser Gly Ala Ile Gly Lys Ser Thr Leu Val
        1205                1210                1215

Pro Leu Asp Thr Pro Ser Pro Ala Thr Ser Leu Glu Ala Ser Glu
        1220                1225                1230

Gly Gly Leu Pro Thr Leu Ser Thr Tyr Pro Glu Ser Thr Asn Thr
        1235                1240                1245

Pro Ser Ile His Leu Gly Ala His Ala Ser Ser Glu Ser Pro Ser
        1250                1255                1260

Thr Ile Lys Leu Thr Met Ala Ser Val Val Lys Pro Gly Ser Tyr
        1265                1270                1275

Thr Pro Leu Thr Phe Pro Ser Ile Glu Thr His Ile His Val Ser
        1280                1285                1290

Thr Ala Arg Met Ala Tyr Ser Ser Gly Ser Ser Pro Glu Met Thr
        1295                1300                1305

Ala Pro Gly Glu Thr Asn Thr Gly Ser Thr Trp Asp Pro Thr Thr
        1310                1315                1320

Tyr Ile Thr Thr Thr Asp Pro Lys Asp Thr Ser Ser Ala Gln Val
        1325                1330                1335

Ser Thr Pro His Ser Val Arg Thr Leu Arg Thr Thr Glu Asn His
        1340                1345                1350

Pro Lys Thr Glu Ser Ala Thr Pro Ala Ala Tyr Ser Gly Ser Pro
        1355                1360                1365

Lys Ile Ser Ser Ser Pro Asn Leu Thr Ser Pro Ala Thr Lys Ala
```

-continued

```
                1370            1375            1380
Trp Thr Ile Thr Asp Thr Thr Glu His Ser Thr Gln Leu His Tyr
    1385            1390            1395
Thr Lys Leu Ala Glu Lys Ser Ser Gly Phe Glu Thr Gln Ser Ala
    1400            1405            1410
Pro Gly Pro Val Ser Val Val Ile Pro Thr Ser Pro Thr Ile Gly
    1415            1420            1425
Ser Ser Thr Leu Glu Leu Thr Ser Asp Val Pro Gly Glu Pro Leu
    1430            1435            1440
Val Leu Ala Pro Ser Glu Gln Thr Thr Ile Thr Leu Pro Met Ala
    1445            1450            1455
Thr Trp Leu Ser Thr Ser Leu Thr Glu Glu Met Ala Ser Thr Asp
    1460            1465            1470
Leu Asp Ile Ser Ser Pro Ser Ser Pro Met Ser Thr Phe Ala Ile
    1475            1480            1485
Phe Pro Pro Met Ser Thr Pro Ser His Glu Leu Ser Lys Ser Glu
    1490            1495            1500
Ala Asp Thr Ser Ala Ile Arg Asn Thr Asp Ser Thr Thr Leu Asp
    1505            1510            1515
Gln His Leu Gly Ile Arg Ser Leu Gly Arg Thr Gly Asp Leu Thr
    1520            1525            1530
Thr Val Pro Ile Thr Pro Leu Thr Thr Thr Trp Thr Ser Val Ile
    1535            1540            1545
Glu His Ser Thr Gln Ala Gln Asp Thr Leu Ser Ala Thr Met Ser
    1550            1555            1560
Pro Thr His Val Thr Gln Ser Leu Lys Asp Gln Thr Ser Ile Pro
    1565            1570            1575
Ala Ser Ala Ser Pro Ser His Leu Thr Glu Val Tyr Pro Glu Leu
    1580            1585            1590
Gly Thr Gln Gly Arg Ser Ser Ser Glu Ala Thr Thr Phe Trp Lys
    1595            1600            1605
Pro Ser Thr Asp Thr Leu Ser Arg Glu Ile Glu Thr Gly Pro Thr
    1610            1615            1620
Asn Ile Gln Ser Thr Pro Pro Met Asp Asn Thr Thr Thr Gly Ser
    1625            1630            1635
Ser Ser Ser Gly Val Thr Leu Gly Ile Ala His Leu Pro Ile Gly
    1640            1645            1650
Thr Ser Ser Pro Ala Glu Thr Ser Thr Asn Met Ala Leu Glu Arg
    1655            1660            1665
Arg Ser Ser Thr Ala Thr Val Ser Met Ala Gly Thr Met Gly Leu
    1670            1675            1680
Leu Val Thr Ser Ala Pro Gly Arg Ser Ile Ser Gln Ser Leu Gly
    1685            1690            1695
Arg Val Ser Ser Val Leu Ser Glu Ser Thr Thr Glu Gly Val Thr
    1700            1705            1710
Asp Ser Ser Lys Gly Ser Ser Pro Arg Leu Asn Thr Gln Gly Asn
    1715            1720            1725
Thr Ala Leu Ser Ser Ser Leu Glu Pro Ser Tyr Ala Glu Gly Ser
    1730            1735            1740
Gln Met Ser Thr Ser Ile Pro Leu Thr Ser Ser Pro Thr Thr Pro
    1745            1750            1755
Asp Val Glu Phe Ile Gly Gly Ser Thr Phe Trp Thr Lys Glu Val
    1760            1765            1770
```

-continued

```
Thr Thr Val Met Thr Ser Asp Ile Ser Lys Ser Ser Ala Arg Thr
    1775                1780                1785

Glu Ser Ser Ser Ala Thr Leu Met Ser Thr Ala Leu Gly Ser Thr
    1790                1795                1800

Glu Asn Thr Gly Lys Glu Lys Leu Arg Thr Ala Ser Met Asp Leu
    1805                1810                1815

Pro Ser Pro Thr Pro Ser Met Glu Val Thr Pro Trp Ile Ser Leu
    1820                1825                1830

Thr Leu Ser Asn Ala Pro Asn Thr Thr Asp Ser Leu Asp Leu Ser
    1835                1840                1845

His Gly Val His Thr Ser Ser Ala Gly Thr Leu Ala Thr Asp Arg
    1850                1855                1860

Ser Leu Asn Thr Gly Val Thr Arg Ala Ser Arg Leu Glu Asn Gly
    1865                1870                1875

Ser Asp Thr Ser Ser Lys Ser Leu Ser Met Gly Asn Ser Thr His
    1880                1885                1890

Thr Ser Met Thr Tyr Thr Glu Lys Ser Glu Val Ser Ser Ser Ile
    1895                1900                1905

His Pro Arg Pro Glu Thr Ser Ala Pro Gly Ala Glu Thr Thr Leu
    1910                1915                1920

Thr Ser Thr Pro Gly Asn Arg Ala Ile Ser Leu Thr Leu Pro Phe
    1925                1930                1935

Ser Ser Ile Pro Val Glu Glu Val Ile Ser Thr Gly Ile Thr Ser
    1940                1945                1950

Gly Pro Asp Ile Asn Ser Ala Pro Met Thr His Ser Pro Ile Thr
    1955                1960                1965

Pro Pro Thr Ile Val Trp Thr Ser Thr Gly Thr Ile Glu Gln Ser
    1970                1975                1980

Thr Gln Pro Leu His Ala Val Ser Ser Glu Lys Val Ser Val Gln
    1985                1990                1995

Thr Gln Ser Thr Pro Tyr Val Asn Ser Val Ala Val Ser Ala Ser
    2000                2005                2010

Pro Thr His Glu Asn Ser Val Ser Ser Gly Ser Ser Thr Ser Ser
    2015                2020                2025

Pro Tyr Ser Ser Ala Ser Leu Glu Ser Leu Asp Ser Thr Ile Ser
    2030                2035                2040

Arg Arg Asn Ala Ile Thr Ser Trp Leu Trp Asp Leu Thr Thr Ser
    2045                2050                2055

Leu Pro Thr Thr Thr Trp Pro Ser Thr Ser Leu Ser Glu Ala Leu
    2060                2065                2070

Ser Ser Gly His Ser Gly Val Ser Asn Pro Ser Ser Thr Thr Thr
    2075                2080                2085

Glu Phe Pro Leu Phe Ser Ala Ala Ser Thr Ser Ala Ala Lys Gln
    2090                2095                2100

Arg Asn Pro Glu Thr Glu Thr His Gly Pro Gln Asn Thr Ala Ala
    2105                2110                2115

Ser Thr Leu Asn Thr Asp Ala Ser Ser Val Thr Gly Leu Ser Glu
    2120                2125                2130

Thr Pro Val Gly Ala Ser Ile Ser Ser Glu Val Pro Leu Pro Met
    2135                2140                2145

Ala Ile Thr Ser Arg Ser Asp Val Ser Gly Leu Thr Ser Glu Ser
    2150                2155                2160
```

```
Thr Ala Asn Pro Ser Leu Gly Thr Ala Ser Ser Ala Gly Thr Lys
2165                2170                2175

Leu Thr Arg Thr Ile Ser Leu Pro Thr Ser Glu Ser Leu Val Ser
2180                2185                2190

Phe Arg Met Asn Lys Asp Pro Trp Thr Val Ser Ile Pro Leu Gly
2195                2200                2205

Ser His Pro Thr Thr Asn Thr Glu Thr Ser Ile Pro Val Asn Ser
2210                2215                2220

Ala Gly Pro Pro Gly Leu Ser Thr Val Ala Ser Asp Val Ile Asp
2225                2230                2235

Thr Pro Ser Asp Gly Ala Glu Ser Ile Pro Thr Val Ser Phe Ser
2240                2245                2250

Pro Ser Pro Asp Thr Glu Val Thr Thr Ile Ser His Phe Pro Glu
2255                2260                2265

Lys Thr Thr His Ser Phe Arg Thr Ile Ser Ser Leu Thr His Glu
2270                2275                2280

Leu Thr Ser Arg Val Thr Pro Ile Pro Gly Asp Trp Met Ser Ser
2285                2290                2295

Ala Met Ser Thr Lys Pro Thr Gly Ala Ser Pro Ser Ile Thr Leu
2300                2305                2310

Gly Glu Arg Arg Thr Ile Thr Ser Ala Ala Pro Thr Thr Ser Pro
2315                2320                2325

Ile Val Leu Thr Ala Ser Phe Thr Glu Thr Ser Thr Val Ser Leu
2330                2335                2340

Asp Asn Glu Thr Thr Val Lys Thr Ser Asp Ile Leu Asp Ala Arg
2345                2350                2355

Lys Thr Asn Glu Leu Pro Ser Asp Ser Ser Ser Ser Ser Asp Leu
2360                2365                2370

Ile Asn Thr Ser Ile Ala Ser Ser Thr Met Asp Val Thr Lys Thr
2375                2380                2385

Ala Ser Ile Ser Pro Thr Ser Ile Ser Gly Met Thr Ala Ser Ser
2390                2395                2400

Ser Pro Ser Leu Phe Ser Ser Asp Arg Pro Gln Val Pro Thr Ser
2405                2410                2415

Thr Thr Glu Thr Asn Thr Ala Thr Ser Pro Ser Val Ser Ser Asn
2420                2425                2430

Thr Tyr Ser Leu Asp Gly Gly Ser Asn Val Gly Gly Thr Pro Ser
2435                2440                2445

Thr Leu Pro Pro Phe Thr Ile Thr His Pro Val Glu Thr Ser Ser
2450                2455                2460

Ala Leu Leu Ala Trp Ser Arg Pro Val Arg Thr Phe Ser Thr Met
2465                2470                2475

Val Ser Thr Asp Thr Ala Ser Gly Glu Asn Pro Thr Ser Ser Asn
2480                2485                2490

Ser Val Val Thr Ser Val Pro Ala Pro Gly Thr Trp Thr Ser Val
2495                2500                2505

Gly Ser Thr Thr Asp Leu Pro Ala Met Gly Phe Leu Lys Thr Ser
2510                2515                2520

Pro Ala Gly Glu Ala His Ser Leu Leu Ala Ser Thr Ile Glu Pro
2525                2530                2535

Ala Thr Ala Phe Thr Pro His Leu Ser Ala Ala Val Val Thr Gly
2540                2545                2550

Ser Ser Ala Thr Ser Glu Ala Ser Leu Leu Thr Thr Ser Glu Ser
```

```
                   2555                2560                2565
Lys Ala Ile His Ser Ser Pro Gln Thr Pro Thr Pro Thr Ser
     2570                2575                2580
Gly Ala Asn Trp Glu Thr Ser Ala Thr Pro Glu Ser Leu Leu Val
 2585                2590                2595
Val Thr Glu Thr Ser Asp Thr Thr Leu Thr Ser Lys Ile Leu Val
 2600                2605                2610
Thr Asp Thr Ile Leu Phe Ser Thr Val Ser Thr Pro Pro Ser Lys
 2615                2620                2625
Phe Pro Ser Thr Gly Thr Leu Ser Gly Ala Ser Phe Pro Thr Leu
 2630                2635                2640
Leu Pro Asp Thr Pro Ala Ile Pro Leu Thr Ala Thr Glu Pro Thr
 2645                2650                2655
Ser Ser Leu Ala Thr Ser Phe Asp Ser Thr Pro Leu Val Thr Ile
 2660                2665                2670
Ala Ser Asp Ser Leu Gly Thr Val Pro Glu Thr Thr Leu Thr Met
 2675                2680                2685
Ser Glu Thr Ser Asn Gly Asp Ala Leu Val Leu Lys Thr Val Ser
 2690                2695                2700
Asn Pro Asp Arg Ser Ile Pro Gly Ile Thr Ile Gln Gly Val Thr
 2705                2710                2715
Glu Ser Pro Leu His Pro Ser Ser Thr Ser Pro Ser Lys Ile Val
 2720                2725                2730
Ala Pro Arg Asn Thr Thr Tyr Glu Gly Ser Ile Thr Val Ala Leu
 2735                2740                2745
Ser Thr Leu Pro Ala Gly Thr Thr Gly Ser Leu Val Phe Ser Gln
 2750                2755                2760
Ser Ser Glu Asn Ser Glu Thr Thr Ala Leu Val Asp Ser Ser Ala
 2765                2770                2775
Gly Leu Glu Arg Ala Ser Val Met Pro Leu Thr Thr Gly Ser Gln
 2780                2785                2790
Gly Met Ala Ser Ser Gly Gly Ile Arg Ser Gly Ser Thr His Ser
 2795                2800                2805
Thr Gly Thr Lys Thr Phe Ser Ser Leu Pro Leu Thr Met Asn Pro
 2810                2815                2820
Gly Glu Val Thr Ala Met Ser Glu Ile Thr Thr Asn Arg Leu Thr
 2825                2830                2835
Ala Thr Gln Ser Thr Ala Pro Lys Gly Ile Pro Val Lys Pro Thr
 2840                2845                2850
Ser Ala Glu Ser Gly Leu Leu Thr Pro Val Ser Ala Ser Ser Ser
 2855                2860                2865
Pro Ser Lys Ala Phe Ala Ser Leu Thr Thr Ala Pro Pro Thr Trp
 2870                2875                2880
Gly Ile Pro Gln Ser Thr Leu Thr Phe Glu Phe Ser Glu Val Pro
 2885                2890                2895
Ser Leu Asp Thr Lys Ser Ala Ser Leu Pro Thr Pro Gly Gln Ser
 2900                2905                2910
Leu Asn Thr Ile Pro Asp Ser Asp Ala Ser Thr Ala Ser Ser Ser
 2915                2920                2925
Leu Ser Lys Ser Pro Glu Lys Asn Pro Arg Ala Arg Met Met Thr
 2930                2935                2940
Ser Thr Lys Ala Ile Ser Ala Ser Ser Phe Gln Ser Thr Gly Phe
 2945                2950                2955
```

```
Thr Glu Thr Pro Glu Gly Ser Ala Ser Pro Ser Met Ala Gly His
    2960            2965                2970

Glu Pro Arg Val Pro Thr Ser Gly Thr Gly Asp Pro Arg Tyr Ala
    2975            2980                2985

Ser Glu Ser Met Ser Tyr Pro Asp Pro Ser Lys Ala Ser Ser Ala
    2990            2995                3000

Met Thr Ser Thr Ser Leu Ala Ser Lys Leu Thr Thr Leu Phe Ser
    3005            3010                3015

Thr Gly Gln Ala Ala Arg Ser Gly Ser Ser Ser Pro Ile Ser
    3020            3025                3030

Leu Ser Thr Glu Lys Glu Thr Ser Phe Leu Ser Pro Thr Ala Ser
    3035            3040                3045

Thr Ser Arg Lys Thr Ser Leu Phe Leu Gly Pro Ser Met Ala Arg
    3050            3055                3060

Gln Pro Asn Ile Leu Val His Leu Gln Thr Ser Ala Leu Thr Leu
    3065            3070                3075

Ser Pro Thr Ser Thr Leu Asn Met Ser Gln Glu Glu Pro Pro Glu
    3080            3085                3090

Leu Thr Ser Ser Gln Thr Ile Ala Glu Glu Glu Gly Thr Thr Ala
    3095            3100                3105

Glu Thr Gln Thr Leu Thr Phe Thr Pro Ser Glu Thr Pro Thr Ser
    3110            3115                3120

Leu Leu Pro Val Ser Ser Pro Thr Glu Pro Thr Ala Arg Arg Lys
    3125            3130                3135

Ser Ser Pro Glu Thr Trp Ala Ser Ser Ile Ser Val Pro Ala Lys
    3140            3145                3150

Thr Ser Leu Val Glu Thr Thr Asp Gly Thr Leu Val Thr Thr Ile
    3155            3160                3165

Lys Met Ser Ser Gln Ala Ala Gln Gly Asn Ser Thr Trp Pro Ala
    3170            3175                3180

Pro Ala Glu Glu Thr Gly Ser Ser Pro Ala Gly Thr Ser Pro Gly
    3185            3190                3195

Ser Pro Glu Met Ser Thr Thr Leu Lys Ile Met Ser Ser Lys Glu
    3200            3205                3210

Pro Ser Ile Ser Pro Glu Ile Arg Ser Thr Val Arg Asn Ser Pro
    3215            3220                3225

Trp Lys Thr Pro Glu Thr Thr Val Pro Met Glu Thr Thr Val Glu
    3230            3235                3240

Pro Val Thr Leu Gln Ser Thr Ala Leu Gly Ser Gly Ser Thr Ser
    3245            3250                3255

Ile Ser His Leu Pro Thr Gly Thr Thr Ser Pro Thr Lys Ser Pro
    3260            3265                3270

Thr Glu Asn Met Leu Ala Thr Glu Arg Val Ser Leu Ser Pro Ser
    3275            3280                3285

Pro Pro Glu Ala Trp Thr Asn Leu Tyr Ser Gly Thr Pro Gly Gly
    3290            3295                3300

Thr Arg Gln Ser Leu Ala Thr Met Ser Ser Val Ser Leu Glu Ser
    3305            3310                3315

Pro Thr Ala Arg Ser Ile Thr Gly Thr Gly Gln Gln Ser Ser Pro
    3320            3325                3330

Glu Leu Val Ser Lys Thr Thr Gly Met Glu Phe Ser Met Trp His
    3335            3340                3345
```

```
Gly Ser Thr Gly Gly Thr Thr Gly Asp Thr His Val Ser Leu Ser
    3350            3355            3360

Thr Ser Ser Asn Ile Leu Glu Asp Pro Val Thr Ser Pro Asn Ser
    3365            3370            3375

Val Ser Ser Leu Thr Asp Lys Ser Lys His Lys Thr Glu Thr Trp
    3380            3385            3390

Val Ser Thr Thr Ala Ile Pro Ser Thr Val Leu Asn Asn Lys Ile
    3395            3400            3405

Met Ala Ala Glu Gln Gln Thr Ser Arg Ser Val Asp Glu Ala Tyr
    3410            3415            3420

Ser Ser Thr Ser Ser Trp Ser Asp Gln Thr Ser Gly Ser Asp Ile
    3425            3430            3435

Thr Leu Gly Ala Ser Pro Asp Val Thr Asn Thr Leu Tyr Ile Thr
    3440            3445            3450

Ser Thr Ala Gln Thr Thr Ser Leu Val Ser Leu Pro Ser Gly Asp
    3455            3460            3465

Gln Gly Ile Thr Ser Leu Thr Asn Pro Ser Gly Gly Lys Thr Ser
    3470            3475            3480

Ser Ala Ser Ser Val Thr Ser Pro Ser Ile Gly Leu Glu Thr Leu
    3485            3490            3495

Arg Ala Asn Val Ser Ala Val Lys Ser Asp Ile Ala Pro Thr Ala
    3500            3505            3510

Gly His Leu Ser Gln Thr Ser Ser Pro Ala Glu Val Ser Ile Leu
    3515            3520            3525

Asp Val Thr Thr Ala Pro Thr Pro Gly Ile Ser Thr Thr Ile Thr
    3530            3535            3540

Thr Met Gly Thr Asn Ser Ile Ser Thr Thr Thr Pro Asn Pro Glu
    3545            3550            3555

Val Gly Met Ser Thr Met Asp Ser Thr Pro Ala Thr Glu Arg Arg
    3560            3565            3570

Thr Thr Ser Thr Glu His Pro Ser Thr Trp Ser Ser Thr Ala Ala
    3575            3580            3585

Ser Asp Ser Trp Thr Val Thr Asp Met Thr Ser Asn Leu Lys Val
    3590            3595            3600

Ala Arg Ser Pro Gly Thr Ile Ser Thr Met His Thr Thr Ser Phe
    3605            3610            3615

Leu Ala Ser Ser Thr Glu Leu Asp Ser Met Ser Thr Pro His Gly
    3620            3625            3630

Arg Ile Thr Val Ile Gly Thr Ser Leu Val Thr Pro Ser Ser Asp
    3635            3640            3645

Ala Ser Ala Val Lys Thr Glu Thr Ser Thr Ser Glu Arg Thr Leu
    3650            3655            3660

Ser Pro Ser Asp Thr Thr Ala Ser Thr Pro Ile Ser Thr Phe Ser
    3665            3670            3675

Arg Val Gln Arg Met Ser Ile Ser Val Pro Asp Ile Leu Ser Thr
    3680            3685            3690

Ser Trp Thr Pro Ser Ser Thr Glu Ala Glu Asp Val Pro Val Ser
    3695            3700            3705

Met Val Ser Thr Asp His Ala Ser Thr Lys Thr Asp Pro Asn Thr
    3710            3715            3720

Pro Leu Ser Thr Phe Leu Phe Asp Ser Leu Ser Thr Leu Asp Trp
    3725            3730            3735

Asp Thr Gly Arg Ser Leu Ser Ser Ala Thr Ala Thr Thr Ser Ala
```

```
                 3740                3745                3750
Pro Gln Gly Ala Thr Thr Pro Gln Glu Leu Thr Leu Glu Thr Met
    3755                3760                3765
Ile Ser Pro Ala Thr Ser Gln Leu Pro Phe Ser Ile Gly His Ile
    3770                3775                3780
Thr Ser Ala Val Thr Pro Ala Ala Met Ala Arg Ser Ser Gly Val
    3785                3790                3795
Thr Phe Ser Arg Pro Asp Pro Thr Ser Lys Lys Ala Glu Gln Thr
    3800                3805                3810
Ser Thr Gln Leu Pro Thr Thr Ser Ala His Pro Gly Gln Val
    3815                3820                3825
Pro Arg Ser Ala Ala Thr Thr Leu Asp Val Ile Pro His Thr Ala
    3830                3835                3840
Lys Thr Pro Asp Ala Thr Phe Gln Arg Gln Gly Gln Thr Ala Leu
    3845                3850                3855
Thr Thr Glu Ala Arg Ala Thr Ser Asp Ser Trp Asn Glu Lys Glu
    3860                3865                3870
Lys Ser Thr Pro Ser Ala Pro Trp Ile Thr Glu Met Met Asn Ser
    3875                3880                3885
Val Ser Glu Asp Thr Ile Lys Glu Val Thr Ser Ser Ser Ser Val
    3890                3895                3900
Leu Arg Thr Leu Asn Thr Leu Asp Ile Asn Leu Glu Ser Gly Thr
    3905                3910                3915
Thr Ser Ser Pro Ser Trp Lys Ser Ser Pro Tyr Glu Arg Ile Ala
    3920                3925                3930
Pro Ser Glu Ser Thr Thr Asp Lys Glu Ala Ile His Pro Ser Thr
    3935                3940                3945
Asn Thr Val Glu Thr Thr Gly Trp Val Thr Ser Ser Glu His Ala
    3950                3955                3960
Ser His Ser Thr Ile Pro Ala His Ser Ala Ser Ser Lys Leu Thr
    3965                3970                3975
Ser Pro Val Val Thr Thr Ser Thr Arg Glu Gln Ala Ile Val Ser
    3980                3985                3990
Met Ser Thr Thr Thr Trp Pro Glu Ser Thr Arg Ala Arg Thr Glu
    3995                4000                4005
Pro Asn Ser Phe Leu Thr Ile Glu Leu Arg Asp Val Ser Pro Tyr
    4010                4015                4020
Met Asp Thr Ser Ser Thr Thr Gln Thr Ser Ile Ile Ser Ser Pro
    4025                4030                4035
Gly Ser Thr Ala Ile Thr Lys Gly Pro Arg Thr Glu Ile Thr Ser
    4040                4045                4050
Ser Lys Arg Ile Ser Ser Ser Phe Leu Ala Gln Ser Met Arg Ser
    4055                4060                4065
Ser Asp Ser Pro Ser Glu Ala Ile Thr Arg Leu Ser Asn Phe Pro
    4070                4075                4080
Ala Met Thr Glu Ser Gly Gly Met Ile Leu Ala Met Gln Thr Ser
    4085                4090                4095
Pro Pro Gly Ala Thr Ser Leu Ser Ala Pro Thr Leu Asp Thr Ser
    4100                4105                4110
Ala Thr Ala Ser Trp Thr Gly Thr Pro Leu Ala Thr Thr Gln Arg
    4115                4120                4125
Phe Thr Tyr Ser Glu Lys Thr Thr Leu Phe Ser Lys Gly Pro Glu
    4130                4135                4140
```

-continued

```
Asp Thr Ser Gln Pro Ser Pro Pro Ser Val Glu Glu Thr Ser Ser
    4145            4150            4155

Ser Ser Ser Leu Val Pro Ile His Ala Thr Thr Ser Pro Ser Asn
    4160            4165            4170

Ile Leu Leu Thr Ser Gln Gly His Ser Pro Ser Ser Thr Pro Pro
    4175            4180            4185

Val Thr Ser Val Phe Leu Ser Glu Thr Ser Gly Leu Gly Lys Thr
    4190            4195            4200

Thr Asp Met Ser Arg Ile Ser Leu Glu Pro Gly Thr Ser Leu Pro
    4205            4210            4215

Pro Asn Leu Ser Ser Thr Ala Gly Glu Ala Leu Ser Thr Tyr Glu
    4220            4225            4230

Ala Ser Arg Asp Thr Lys Ala Ile His His Ser Ala Asp Thr Ala
    4235            4240            4245

Val Thr Asn Met Glu Ala Thr Ser Ser Glu Tyr Ser Pro Ile Pro
    4250            4255            4260

Gly His Thr Lys Pro Ser Lys Ala Thr Ser Pro Leu Val Thr Ser
    4265            4270            4275

His Ile Met Gly Asp Ile Thr Ser Ser Thr Ser Val Phe Gly Ser
    4280            4285            4290

Ser Glu Thr Thr Glu Ile Glu Thr Val Ser Ser Val Asn Gln Gly
    4295            4300            4305

Leu Gln Glu Arg Ser Thr Ser Gln Val Ala Ser Ser Ala Thr Glu
    4310            4315            4320

Thr Ser Thr Val Ile Thr His Val Ser Ser Gly Asp Ala Thr Thr
    4325            4330            4335

His Val Thr Lys Thr Gln Ala Thr Phe Ser Ser Gly Thr Ser Ile
    4340            4345            4350

Ser Ser Pro His Gln Phe Ile Thr Ser Thr Asn Thr Phe Thr Asp
    4355            4360            4365

Val Ser Thr Asn Pro Ser Thr Ser Leu Ile Met Thr Glu Ser Ser
    4370            4375            4380

Gly Val Thr Ile Thr Thr Gln Thr Gly Pro Thr Gly Ala Ala Thr
    4385            4390            4395

Gln Gly Pro Tyr Leu Leu Asp Thr Ser Thr Met Pro Tyr Leu Thr
    4400            4405            4410

Glu Thr Pro Leu Ala Val Thr Pro Asp Phe Met Gln Ser Glu Lys
    4415            4420            4425

Thr Thr Leu Ile Ser Lys Gly Pro Lys Asp Val Ser Trp Thr Ser
    4430            4435            4440

Pro Pro Ser Val Ala Glu Thr Ser Tyr Pro Ser Ser Leu Thr Pro
    4445            4450            4455

Phe Leu Val Thr Thr Ile Pro Pro Ala Thr Ser Thr Leu Gln Gly
    4460            4465            4470

Gln His Thr Ser Ser Pro Val Ser Ala Thr Ser Val Leu Thr Ser
    4475            4480            4485

Gly Leu Val Lys Thr Thr Asp Met Leu Asn Thr Ser Met Glu Pro
    4490            4495            4500

Val Thr Asn Ser Pro Gln Asn Leu Asn Asn Pro Ser Asn Glu Ile
    4505            4510            4515

Leu Ala Thr Leu Ala Ala Thr Thr Asp Ile Glu Thr Ile His Pro
    4520            4525            4530
```

```
Ser Ile Asn Lys Ala Val Thr Asn Met Gly Thr Ala Ser Ser Ala
4535                4540                4545

His Val Leu His Ser Thr Leu Pro Val Ser Ser Glu Pro Ser Thr
4550                4555                4560

Ala Thr Ser Pro Met Val Pro Ala Ser Ser Met Gly Asp Ala Leu
4565                4570                4575

Ala Ser Ile Ser Ile Pro Gly Ser Glu Thr Thr Asp Ile Glu Gly
4580                4585                4590

Glu Pro Thr Ser Ser Leu Thr Ala Gly Arg Lys Glu Asn Ser Thr
4595                4600                4605

Leu Gln Glu Met Asn Ser Thr Thr Glu Ser Asn Ile Ile Leu Ser
4610                4615                4620

Asn Val Ser Val Gly Ala Ile Thr Glu Ala Thr Lys Met Glu Val
4625                4630                4635

Pro Ser Phe Asp Ala Thr Phe Ile Pro Thr Pro Ala Gln Ser Thr
4640                4645                4650

Lys Phe Pro Asp Ile Phe Ser Val Ala Ser Ser Arg Leu Ser Asn
4655                4660                4665

Ser Pro Pro Met Thr Ile Ser Thr His Met Thr Thr Gln Thr
4670                4675                4680

Gly Ser Ser Gly Ala Thr Ser Lys Ile Pro Leu Ala Leu Asp Thr
4685                4690                4695

Ser Thr Leu Glu Thr Ser Ala Gly Thr Pro Ser Val Val Thr Glu
4700                4705                4710

Gly Phe Ala His Ser Lys Ile Thr Thr Ala Met Asn Asn Asp Val
4715                4720                4725

Lys Asp Val Ser Gln Thr Asn Pro Pro Phe Gln Asp Glu Ala Ser
4730                4735                4740

Ser Pro Ser Ser Gln Ala Pro Val Leu Val Thr Thr Leu Pro Ser
4745                4750                4755

Ser Val Ala Phe Thr Pro Gln Trp His Ser Thr Ser Ser Pro Val
4760                4765                4770

Ser Met Ser Ser Val Leu Thr Ser Ser Leu Val Lys Thr Ala Gly
4775                4780                4785

Lys Val Asp Thr Ser Leu Glu Thr Val Thr Ser Ser Pro Gln Ser
4790                4795                4800

Met Ser Asn Thr Leu Asp Asp Ile Ser Val Thr Ser Ala Ala Thr
4805                4810                4815

Thr Asp Ile Glu Thr Thr His Pro Ser Ile Asn Thr Val Val Thr
4820                4825                4830

Asn Val Gly Thr Thr Gly Ser Ala Phe Glu Ser His Ser Thr Val
4835                4840                4845

Ser Ala Tyr Pro Glu Pro Ser Lys Val Thr Ser Pro Asn Val Thr
4850                4855                4860

Thr Ser Thr Met Glu Asp Thr Thr Ile Ser Arg Ser Ile Pro Lys
4865                4870                4875

Ser Ser Lys Thr Thr Arg Thr Glu Thr Glu Thr Ser Ser Leu
4880                4885                4890

Thr Pro Lys Leu Arg Glu Thr Ser Ile Ser Gln Glu Ile Thr Ser
4895                4900                4905

Ser Thr Glu Thr Ser Thr Val Pro Tyr Lys Glu Leu Thr Gly Ala
4910                4915                4920

Thr Thr Glu Val Ser Arg Thr Asp Val Thr Ser Ser Ser Ser Thr
```

-continued

```
              4925                4930                4935
Ser Phe Pro Gly Pro Asp Gln Ser Thr Val Ser Leu Asp Ile Ser
    4940                4945                4950
Thr Glu Thr Asn Thr Arg Leu Ser Thr Ser Pro Ile Met Thr Glu
    4955                4960                4965
Ser Ala Glu Ile Thr Ile Thr Thr Gln Thr Gly Pro His Gly Ala
    4970                4975                4980
Thr Ser Gln Asp Thr Phe Thr Met Asp Pro Ser Asn Thr Thr Pro
    4985                4990                4995
Gln Ala Gly Ile His Ser Ala Met Thr His Gly Phe Ser Gln Leu
    5000                5005                5010
Asp Val Thr Thr Leu Met Ser Arg Ile Pro Gln Asp Val Ser Trp
    5015                5020                5025
Thr Ser Pro Pro Ser Val Asp Lys Thr Ser Ser Pro Ser Ser Phe
    5030                5035                5040
Leu Ser Ser Pro Ala Met Thr Thr Pro Ser Leu Ile Ser Ser Thr
    5045                5050                5055
Leu Pro Glu Asp Lys Leu Ser Ser Pro Met Thr Ser Leu Leu Thr
    5060                5065                5070
Ser Gly Leu Val Lys Ile Thr Asp Ile Leu Arg Thr Arg Leu Glu
    5075                5080                5085
Pro Val Thr Ser Ser Leu Pro Asn Phe Ser Ser Thr Ser Asp Lys
    5090                5095                5100
Ile Leu Ala Thr Ser Lys Asp Ser Lys Asp Thr Lys Glu Ile Phe
    5105                5110                5115
Pro Ser Ile Asn Thr Glu Glu Thr Asn Val Lys Ala Asn Asn Ser
    5120                5125                5130
Gly His Glu Ser His Ser Pro Ala Leu Ala Asp Ser Glu Thr Pro
    5135                5140                5145
Lys Ala Thr Thr Gln Met Val Ile Thr Thr Val Gly Asp Pro
    5150                5155                5160
Ala Pro Ser Thr Ser Met Pro Val His Gly Ser Ser Glu Thr Thr
    5165                5170                5175
Asn Ile Lys Arg Glu Pro Thr Tyr Phe Leu Thr Pro Arg Leu Arg
    5180                5185                5190
Glu Thr Ser Thr Ser Gln Glu Ser Ser Phe Pro Thr Asp Thr Ser
    5195                5200                5205
Phe Leu Leu Ser Lys Val Pro Thr Gly Thr Ile Thr Glu Val Ser
    5210                5215                5220
Ser Thr Gly Val Asn Ser Ser Ser Lys Ile Ser Thr Pro Asp His
    5225                5230                5235
Asp Lys Ser Thr Val Pro Pro Asp Thr Phe Thr Gly Glu Ile Pro
    5240                5245                5250
Arg Val Phe Thr Ser Ser Ile Lys Thr Lys Ser Ala Glu Met Thr
    5255                5260                5265
Ile Thr Thr Gln Ala Ser Pro Pro Glu Ser Ala Ser His Ser Thr
    5270                5275                5280
Leu Pro Leu Asp Thr Ser Thr Thr Leu Ser Gln Gly Gly Thr His
    5285                5290                5295
Ser Thr Val Thr Gln Gly Phe Pro Tyr Ser Glu Val Thr Thr Leu
    5300                5305                5310
Met Gly Met Gly Pro Gly Asn Val Ser Trp Met Thr Thr Pro Pro
    5315                5320                5325
```

-continued

```
Val Glu Glu Thr Ser Ser Val Ser Ser Leu Met Ser Ser Pro Ala
    5330                5335                5340

Met Thr Ser Pro Ser Pro Val Ser Ser Thr Ser Pro Gln Ser Ile
    5345                5350                5355

Pro Ser Ser Pro Leu Pro Val Thr Ala Leu Pro Thr Ser Val Leu
    5360                5365                5370

Val Thr Thr Thr Asp Val Leu Gly Thr Thr Ser Pro Glu Ser Val
    5375                5380                5385

Thr Ser Ser Pro Pro Asn Leu Ser Ser Ile Thr His Glu Arg Pro
    5390                5395                5400

Ala Thr Tyr Lys Asp Thr Ala His Thr Glu Ala Ala Met His His
    5405                5410                5415

Ser Thr Asn Thr Ala Val Thr Asn Val Gly Thr Ser Gly Ser Gly
    5420                5425                5430

His Lys Ser Gln Ser Ser Val Leu Ala Asp Ser Glu Thr Ser Lys
    5435                5440                5445

Ala Thr Pro Leu Met Ser Thr Thr Ser Thr Leu Gly Asp Thr Ser
    5450                5455                5460

Val Ser Thr Ser Thr Pro Asn Ile Ser Gln Thr Asn Gln Ile Gln
    5465                5470                5475

Thr Glu Pro Thr Ala Ser Leu Ser Pro Arg Leu Arg Glu Ser Ser
    5480                5485                5490

Thr Ser Glu Lys Thr Ser Ser Thr Thr Glu Thr Asn Thr Ala Phe
    5495                5500                5505

Ser Tyr Val Pro Thr Gly Ala Ile Thr Gln Ala Ser Arg Thr Glu
    5510                5515                5520

Ile Ser Ser Ser Arg Thr Ser Ile Ser Asp Leu Asp Arg Pro Thr
    5525                5530                5535

Ile Ala Pro Asp Ile Ser Thr Gly Met Ile Thr Arg Leu Phe Thr
    5540                5545                5550

Ser Pro Ile Met Thr Lys Ser Ala Glu Met Thr Val Thr Thr Gln
    5555                5560                5565

Thr Thr Thr Pro Gly Ala Thr Ser Gln Gly Ile Leu Pro Trp Asp
    5570                5575                5580

Thr Ser Thr Thr Leu Phe Gln Gly Gly Thr His Ser Thr Val Ser
    5585                5590                5595

Gln Gly Phe Pro His Ser Glu Ile Thr Thr Leu Arg Ser Arg Thr
    5600                5605                5610

Pro Gly Asp Val Ser Trp Met Thr Thr Pro Pro Val Glu Glu Thr
    5615                5620                5625

Ser Ser Gly Phe Ser Leu Met Ser Pro Ser Met Thr Ser Pro Ser
    5630                5635                5640

Pro Val Ser Ser Thr Ser Pro Glu Ser Ile Pro Ser Ser Pro Leu
    5645                5650                5655

Pro Val Thr Ala Leu Leu Thr Ser Val Leu Val Thr Thr Thr Asn
    5660                5665                5670

Val Leu Gly Thr Thr Ser Pro Glu Pro Val Thr Ser Ser Pro Pro
    5675                5680                5685

Asn Leu Ser Ser Pro Thr Gln Glu Arg Leu Thr Thr Tyr Lys Asp
    5690                5695                5700

Thr Ala His Thr Glu Ala Met His Ala Ser Met His Thr Asn Thr
    5705                5710                5715
```

-continued

```
Ala Val Ala Asn Val Gly Thr Ser Ile Ser Gly His Glu Ser Gln
    5720            5725            5730

Ser Ser Val Pro Ala Asp Ser His Thr Ser Lys Ala Thr Ser Pro
    5735            5740            5745

Met Gly Ile Thr Phe Ala Met Gly Asp Thr Ser Val Ser Thr Ser
    5750            5755            5760

Thr Pro Ala Phe Phe Glu Thr Arg Ile Gln Thr Glu Ser Thr Ser
    5765            5770            5775

Ser Leu Ile Pro Gly Leu Arg Asp Thr Arg Thr Ser Glu Glu Ile
    5780            5785            5790

Asn Thr Val Thr Glu Thr Ser Thr Val Leu Ser Glu Val Pro Thr
    5795            5800            5805

Thr Thr Thr Thr Glu Val Ser Arg Thr Glu Val Ile Thr Ser Ser
    5810            5815            5820

Arg Thr Thr Ile Ser Gly Pro Asp His Ser Lys Met Ser Pro Tyr
    5825            5830            5835

Ile Ser Thr Glu Thr Ile Thr Arg Leu Ser Thr Phe Pro Phe Val
    5840            5845            5850

Thr Gly Ser Thr Glu Met Ala Ile Thr Asn Gln Thr Gly Pro Ile
    5855            5860            5865

Gly Thr Ile Ser Gln Ala Thr Leu Thr Leu Asp Thr Ser Ser Thr
    5870            5875            5880

Ala Ser Trp Glu Gly Thr His Ser Pro Val Thr Gln Arg Phe Pro
    5885            5890            5895

His Ser Glu Glu Thr Thr Thr Met Ser Arg Ser Thr Lys Gly Val
    5900            5905            5910

Ser Trp Gln Ser Pro Pro Ser Val Glu Glu Thr Ser Ser Pro Ser
    5915            5920            5925

Ser Pro Val Pro Leu Pro Ala Ile Thr Ser His Ser Ser Leu Tyr
    5930            5935            5940

Ser Ala Val Ser Gly Ser Ser Pro Thr Ser Ala Leu Pro Val Thr
    5945            5950            5955

Ser Leu Leu Thr Ser Gly Arg Arg Lys Thr Ile Asp Met Leu Asp
    5960            5965            5970

Thr His Ser Glu Leu Val Thr Ser Ser Leu Pro Ser Ala Ser Ser
    5975            5980            5985

Phe Ser Gly Glu Ile Leu Thr Ser Glu Ala Ser Thr Asn Thr Glu
    5990            5995            6000

Thr Ile His Phe Ser Glu Asn Thr Ala Glu Thr Asn Met Gly Thr
    6005            6010            6015

Thr Asn Ser Met His Lys Leu His Ser Ser Val Ser Ile His Ser
    6020            6025            6030

Gln Pro Ser Gly His Thr Pro Pro Lys Val Thr Gly Ser Met Met
    6035            6040            6045

Glu Asp Ala Ile Val Ser Thr Ser Thr Pro Gly Ser Pro Glu Thr
    6050            6055            6060

Lys Asn Val Asp Arg Asp Ser Thr Ser Pro Leu Thr Pro Glu Leu
    6065            6070            6075

Lys Glu Asp Ser Thr Ala Leu Val Met Asn Ser Thr Thr Glu Ser
    6080            6085            6090

Asn Thr Val Phe Ser Ser Val Ser Leu Asp Ala Ala Thr Glu Val
    6095            6100            6105

Ser Arg Ala Glu Val Thr Tyr Tyr Asp Pro Thr Phe Met Pro Ala
```

-continued

```
                6110                6115                6120

Ser Ala Gln Ser Thr Lys Ser Pro Asp Ile Ser Pro Glu Ala Ser
        6125                6130                6135

Ser Ser His Ser Asn Ser Pro Pro Leu Thr Ile Ser Thr His Lys
        6140                6145                6150

Thr Ile Ala Thr Gln Thr Gly Pro Ser Gly Val Thr Ser Leu Gly
        6155                6160                6165

Gln Leu Thr Leu Asp Thr Ser Thr Ile Ala Thr Ser Ala Gly Thr
        6170                6175                6180

Pro Ser Ala Arg Thr Gln Asp Phe Val Asp Ser Glu Thr Thr Ser
        6185                6190                6195

Val Met Asn Asn Asp Leu Asn Asp Val Leu Lys Thr Ser Pro Phe
        6200                6205                6210

Ser Ala Glu Glu Ala Asn Ser Leu Ser Ser Gln Ala Pro Leu Leu
        6215                6220                6225

Val Thr Thr Ser Pro Ser Pro Val Thr Ser Thr Leu Gln Glu His
        6230                6235                6240

Ser Thr Ser Ser Leu Val Ser Val Thr Ser Val Pro Thr Pro Thr
        6245                6250                6255

Leu Ala Lys Ile Thr Asp Met Asp Thr Asn Leu Glu Pro Val Thr
        6260                6265                6270

Arg Ser Pro Gln Asn Leu Arg Asn Thr Leu Ala Thr Ser Glu Ala
        6275                6280                6285

Thr Thr Asp Thr His Thr Met His Pro Ser Ile Asn Thr Ala Val
        6290                6295                6300

Ala Asn Val Gly Thr Thr Ser Ser Pro Asn Glu Phe Tyr Phe Thr
        6305                6310                6315

Val Ser Pro Asp Ser Asp Pro Tyr Lys Ala Thr Ser Ala Val Val
        6320                6325                6330

Ile Thr Ser Thr Ser Gly Asp Ser Ile Val Ser Thr Ser Met Pro
        6335                6340                6345

Arg Ser Ser Ala Met Lys Lys Ile Glu Ser Glu Thr Thr Phe Ser
        6350                6355                6360

Leu Ile Phe Arg Leu Arg Glu Thr Ser Thr Ser Gln Lys Ile Gly
        6365                6370                6375

Ser Ser Ser Asp Thr Ser Thr Val Phe Asp Lys Ala Phe Thr Ala
        6380                6385                6390

Ala Thr Thr Glu Val Ser Arg Thr Glu Leu Thr Ser Ser Ser Arg
        6395                6400                6405

Thr Ser Ile Gln Gly Thr Glu Lys Pro Thr Met Ser Pro Asp Thr
        6410                6415                6420

Ser Thr Arg Ser Val Thr Met Leu Ser Thr Phe Ala Gly Leu Thr
        6425                6430                6435

Lys Ser Glu Glu Arg Thr Ile Ala Thr Gln Thr Gly Pro His Arg
        6440                6445                6450

Ala Thr Ser Gln Gly Thr Leu Thr Trp Asp Thr Ser Ile Thr Thr
        6455                6460                6465

Ser Gln Ala Gly Thr His Ser Ala Met Thr His Gly Phe Ser Gln
        6470                6475                6480

Leu Asp Leu Ser Thr Leu Thr Ser Arg Val Pro Glu Tyr Ile Ser
        6485                6490                6495

Gly Thr Ser Pro Pro Ser Val Glu Lys Thr Ser Ser Ser Ser Ser
        6500                6505                6510
```

-continued

```
Leu Leu Ser Leu Pro Ala Ile Thr Ser Pro Ser Pro Val Pro Thr
6515                6520                6525

Thr Leu Pro Glu Ser Arg Pro Ser Ser Pro Val His Leu Thr Ser
6530                6535                6540

Leu Pro Thr Ser Gly Leu Val Lys Thr Thr Asp Met Leu Ala Ser
6545                6550                6555

Val Ala Ser Leu Pro Pro Asn Leu Gly Ser Thr Ser His Lys Ile
6560                6565                6570

Pro Thr Thr Ser Glu Asp Ile Lys Asp Thr Glu Lys Met Tyr Pro
6575                6580                6585

Ser Thr Asn Ile Ala Val Thr Asn Val Gly Thr Thr Ser Glu
6590                6595                6600

Lys Glu Ser Tyr Ser Ser Val Pro Ala Tyr Ser Glu Pro Pro Lys
6605                6610                6615

Val Thr Ser Pro Met Val Thr Ser Phe Asn Ile Arg Asp Thr Ile
6620                6625                6630

Val Ser Thr Ser Met Pro Gly Ser Ser Glu Ile Thr Arg Ile Glu
6635                6640                6645

Met Glu Ser Thr Phe Ser Leu Ala His Gly Leu Lys Gly Thr Ser
6650                6655                6660

Thr Ser Gln Asp Pro Ile Val Ser Thr Glu Lys Ser Ala Val Leu
6665                6670                6675

His Lys Leu Thr Thr Gly Ala Thr Glu Thr Ser Arg Thr Glu Val
6680                6685                6690

Ala Ser Ser Arg Arg Thr Ser Ile Pro Gly Pro Asp His Ser Thr
6695                6700                6705

Glu Ser Pro Asp Ile Ser Thr Glu Val Ile Pro Ser Leu Pro Ile
6710                6715                6720

Ser Leu Gly Ile Thr Glu Ser Ser Asn Met Thr Ile Ile Thr Arg
6725                6730                6735

Thr Gly Pro Pro Leu Gly Ser Thr Ser Gln Gly Thr Phe Thr Leu
6740                6745                6750

Asp Thr Pro Thr Thr Ser Ser Arg Ala Gly Thr His Ser Met Ala
6755                6760                6765

Thr Gln Glu Phe Pro His Ser Glu Met Thr Thr Val Met Asn Lys
6770                6775                6780

Asp Pro Glu Ile Leu Ser Trp Thr Ile Pro Pro Ser Ile Glu Lys
6785                6790                6795

Thr Ser Phe Ser Ser Ser Leu Met Pro Ser Pro Ala Met Thr Ser
6800                6805                6810

Pro Pro Val Ser Ser Thr Leu Pro Lys Thr Ile His Thr Thr Pro
6815                6820                6825

Ser Pro Met Thr Ser Leu Leu Thr Pro Ser Leu Val Met Thr Thr
6830                6835                6840

Asp Thr Leu Gly Thr Ser Pro Glu Pro Thr Thr Ser Ser Pro Pro
6845                6850                6855

Asn Leu Ser Ser Thr Ser His Glu Ile Leu Thr Thr Asp Glu Asp
6860                6865                6870

Thr Thr Ala Ile Glu Ala Met His Pro Ser Ser Thr Ala Ala
6875                6880                6885

Thr Asn Val Glu Thr Thr Ser Ser Gly His Gly Ser Gln Ser Ser
6890                6895                6900
```

| | | | | | | | | | | | | |
|---|---|---|---|---|---|---|---|---|---|---|---|---|
| Val | Leu | Ala | Asp | Ser | Glu | Lys | Thr | Lys | Ala | Thr | Ala | Pro | Met | Asp |
| | 6905 | | | | | 6910 | | | | | 6915 | | | |
| Thr | Thr | Ser | Thr | Met | Gly | His | Thr | Thr | Val | Ser | Thr | Ser | Met | Ser |
| | 6920 | | | | | 6925 | | | | | 6930 | | | |
| Val | Ser | Ser | Glu | Thr | Thr | Lys | Ile | Lys | Arg | Glu | Ser | Thr | Tyr | Ser |
| | 6935 | | | | | 6940 | | | | | 6945 | | | |
| Leu | Thr | Pro | Gly | Leu | Arg | Glu | Thr | Ser | Ile | Ser | Gln | Asn | Ala | Ser |
| | 6950 | | | | | 6955 | | | | | 6960 | | | |
| Phe | Ser | Thr | Asp | Thr | Ser | Ile | Val | Leu | Ser | Glu | Val | Pro | Thr | Gly |
| | 6965 | | | | | 6970 | | | | | 6975 | | | |
| Thr | Thr | Ala | Glu | Val | Ser | Arg | Thr | Glu | Val | Thr | Ser | Ser | Gly | Arg |
| | 6980 | | | | | 6985 | | | | | 6990 | | | |
| Thr | Ser | Ile | Pro | Gly | Pro | Ser | Gln | Ser | Thr | Val | Leu | Pro | Glu | Ile |
| | 6995 | | | | | 7000 | | | | | 7005 | | | |
| Ser | Thr | Arg | Thr | Met | Thr | Arg | Leu | Phe | Ala | Ser | Pro | Thr | Met | Thr |
| | 7010 | | | | | 7015 | | | | | 7020 | | | |
| Glu | Ser | Ala | Glu | Met | Thr | Ile | Pro | Thr | Gln | Thr | Gly | Pro | Ser | Gly |
| | 7025 | | | | | 7030 | | | | | 7035 | | | |
| Ser | Thr | Ser | Gln | Asp | Thr | Leu | Thr | Leu | Asp | Thr | Ser | Thr | Thr | Lys |
| | 7040 | | | | | 7045 | | | | | 7050 | | | |
| Ser | Gln | Ala | Lys | Thr | His | Ser | Thr | Leu | Thr | Gln | Arg | Phe | Pro | His |
| | 7055 | | | | | 7060 | | | | | 7065 | | | |
| Ser | Glu | Met | Thr | Thr | Leu | Met | Ser | Arg | Gly | Pro | Gly | Asp | Met | Ser |
| | 7070 | | | | | 7075 | | | | | 7080 | | | |
| Trp | Gln | Ser | Ser | Pro | Ser | Leu | Glu | Asn | Pro | Ser | Ser | Leu | Pro | Ser |
| | 7085 | | | | | 7090 | | | | | 7095 | | | |
| Leu | Leu | Ser | Leu | Pro | Ala | Thr | Thr | Ser | Pro | Pro | Pro | Ile | Ser | Ser |
| | 7100 | | | | | 7105 | | | | | 7110 | | | |
| Thr | Leu | Pro | Val | Thr | Ile | Ser | Ser | Ser | Pro | Leu | Pro | Val | Thr | Ser |
| | 7115 | | | | | 7120 | | | | | 7125 | | | |
| Leu | Leu | Thr | Ser | Ser | Pro | Val | Thr | Thr | Thr | Asp | Met | Leu | His | Thr |
| | 7130 | | | | | 7135 | | | | | 7140 | | | |
| Ser | Pro | Glu | Leu | Val | Thr | Ser | Ser | Pro | Pro | Lys | Leu | Ser | His | Thr |
| | 7145 | | | | | 7150 | | | | | 7155 | | | |
| Ser | Asp | Glu | Arg | Leu | Thr | Thr | Gly | Lys | Asp | Thr | Thr | Asn | Thr | Glu |
| | 7160 | | | | | 7165 | | | | | 7170 | | | |
| Ala | Val | His | Pro | Ser | Thr | Asn | Thr | Ala | Ala | Ser | Asn | Val | Glu | Ile |
| | 7175 | | | | | 7180 | | | | | 7185 | | | |
| Pro | Ser | Ser | Gly | His | Glu | Ser | Pro | Ser | Ser | Ala | Leu | Ala | Asp | Ser |
| | 7190 | | | | | 7195 | | | | | 7200 | | | |
| Glu | Thr | Ser | Lys | Ala | Thr | Ser | Pro | Met | Phe | Ile | Thr | Ser | Thr | Gln |
| | 7205 | | | | | 7210 | | | | | 7215 | | | |
| Glu | Asp | Thr | Thr | Val | Ala | Ile | Ser | Thr | Pro | His | Phe | Leu | Glu | Thr |
| | 7220 | | | | | 7225 | | | | | 7230 | | | |
| Ser | Arg | Ile | Gln | Lys | Glu | Ser | Ile | Ser | Ser | Leu | Ser | Pro | Lys | Leu |
| | 7235 | | | | | 7240 | | | | | 7245 | | | |
| Arg | Glu | Thr | Gly | Ser | Ser | Val | Glu | Thr | Ser | Ser | Ala | Ile | Glu | Thr |
| | 7250 | | | | | 7255 | | | | | 7260 | | | |
| Ser | Ala | Val | Leu | Ser | Glu | Val | Ser | Ile | Gly | Ala | Thr | Thr | Glu | Ile |
| | 7265 | | | | | 7270 | | | | | 7275 | | | |
| Ser | Arg | Thr | Glu | Val | Thr | Ser | Ser | Ser | Arg | Thr | Ser | Ile | Ser | Gly |
| | 7280 | | | | | 7285 | | | | | 7290 | | | |
| Ser | Ala | Glu | Ser | Thr | Met | Leu | Pro | Glu | Ile | Ser | Thr | Thr | Arg | Lys |

-continued

```
            7295                7300                7305
Ile Ile Lys Phe Pro Thr Ser Pro Ile Leu Ala Glu Ser Ser Glu
            7310                7315                7320
Met Thr Ile Lys Thr Gln Thr Ser Pro Pro Gly Ser Thr Ser Glu
            7325                7330                7335
Ser Thr Phe Thr Leu Asp Thr Ser Thr Pro Ser Leu Val Ile
            7340                7345                7350
Thr His Ser Thr Met Thr Gln Arg Leu Pro His Ser Glu Ile Thr
            7355                7360                7365
Thr Leu Val Ser Arg Gly Ala Gly Asp Val Pro Arg Pro Ser Ser
            7370                7375                7380
Leu Pro Val Glu Glu Thr Ser Pro Pro Ser Ser Gln Leu Ser Leu
            7385                7390                7395
Ser Ala Met Ile Ser Pro Ser Pro Val Ser Ser Thr Leu Pro Ala
            7400                7405                7410
Ser Ser His Ser Ser Ser Ala Ser Val Thr Ser Leu Leu Thr Pro
            7415                7420                7425
Gly Gln Val Lys Thr Thr Glu Val Leu Asp Ala Ser Ala Glu Pro
            7430                7435                7440
Glu Thr Ser Ser Pro Pro Ser Leu Ser Ser Thr Ser Val Glu Ile
            7445                7450                7455
Leu Ala Thr Ser Glu Val Thr Thr Asp Thr Glu Lys Ile His Pro
            7460                7465                7470
Phe Ser Asn Thr Ala Val Thr Lys Val Gly Thr Ser Ser Ser Gly
            7475                7480                7485
His Glu Ser Pro Ser Ser Val Leu Pro Asp Ser Glu Thr Thr Lys
            7490                7495                7500
Ala Thr Ser Ala Met Gly Thr Ile Ser Ile Met Gly Asp Thr Ser
            7505                7510                7515
Val Ser Thr Leu Thr Pro Ala Leu Ser Asn Thr Arg Lys Ile Gln
            7520                7525                7530
Ser Glu Pro Ala Ser Ser Leu Thr Thr Arg Leu Arg Glu Thr Ser
            7535                7540                7545
Thr Ser Glu Glu Thr Ser Leu Ala Thr Glu Ala Asn Thr Val Leu
            7550                7555                7560
Ser Lys Val Ser Thr Gly Ala Thr Thr Glu Val Ser Arg Thr Glu
            7565                7570                7575
Ala Ile Ser Phe Ser Arg Thr Ser Met Ser Gly Pro Glu Gln Ser
            7580                7585                7590
Thr Met Ser Gln Asp Ile Ser Ile Gly Thr Ile Pro Arg Ile Ser
            7595                7600                7605
Ala Ser Ser Val Leu Thr Glu Ser Ala Lys Met Thr Ile Thr Thr
            7610                7615                7620
Gln Thr Gly Pro Ser Glu Ser Thr Leu Glu Ser Thr Leu Asn Leu
            7625                7630                7635
Asn Thr Ala Thr Thr Pro Ser Trp Val Glu Thr His Ser Ile Val
            7640                7645                7650
Ile Gln Gly Phe Pro His Pro Glu Met Thr Thr Ser Met Gly Arg
            7655                7660                7665
Gly Pro Gly Gly Val Ser Trp Pro Ser Pro Phe Val Lys Glu
            7670                7675                7680
Thr Ser Pro Pro Ser Ser Pro Leu Ser Leu Pro Ala Val Thr Ser
            7685                7690                7695
```

-continued

```
Pro His Pro Val Ser Thr Thr Phe Leu Ala His Ile Pro Pro Ser
    7700            7705            7710

Pro Leu Pro Val Thr Ser Leu Leu Thr Ser Gly Pro Ala Thr Thr
    7715            7720            7725

Thr Asp Ile Leu Gly Thr Ser Thr Glu Pro Gly Thr Ser Ser Ser
    7730            7735            7740

Ser Ser Leu Ser Thr Thr Ser His Glu Arg Leu Thr Thr Tyr Lys
    7745            7750            7755

Asp Thr Ala His Thr Glu Ala Val His Pro Ser Thr Asn Thr Gly
    7760            7765            7770

Gly Thr Asn Val Ala Thr Thr Ser Ser Gly Tyr Lys Ser Gln Ser
    7775            7780            7785

Ser Val Leu Ala Asp Ser Ser Pro Met Cys Thr Thr Ser Thr Met
    7790            7795            7800

Gly Asp Thr Ser Val Leu Thr Ser Thr Pro Ala Phe Leu Glu Thr
    7805            7810            7815

Arg Arg Ile Gln Thr Glu Leu Ala Ser Ser Leu Thr Pro Gly Leu
    7820            7825            7830

Arg Glu Ser Ser Gly Ser Glu Gly Thr Ser Ser Gly Thr Lys Met
    7835            7840            7845

Ser Thr Val Leu Ser Lys Val Pro Thr Gly Ala Thr Thr Glu Ile
    7850            7855            7860

Ser Lys Glu Asp Val Thr Ser Ile Pro Gly Pro Ala Gln Ser Thr
    7865            7870            7875

Ile Ser Pro Asp Ile Ser Thr Arg Thr Val Ser Trp Phe Ser Thr
    7880            7885            7890

Ser Pro Val Met Thr Glu Ser Ala Glu Ile Thr Met Asn Thr His
    7895            7900            7905

Thr Ser Pro Leu Gly Ala Thr Thr Gln Gly Thr Ser Thr Leu Asp
    7910            7915            7920

Thr Ser Ser Thr Thr Ser Leu Thr Met Thr His Ser Thr Ile Ser
    7925            7930            7935

Gln Gly Phe Ser His Ser Gln Met Ser Thr Leu Met Arg Arg Gly
    7940            7945            7950

Pro Glu Asp Val Ser Trp Met Ser Pro Pro Leu Leu Glu Lys Thr
    7955            7960            7965

Arg Pro Ser Phe Ser Leu Met Ser Ser Pro Ala Thr Thr Ser Pro
    7970            7975            7980

Ser Pro Val Ser Ser Thr Leu Pro Glu Ser Ile Ser Ser Ser Pro
    7985            7990            7995

Leu Pro Val Thr Ser Leu Leu Thr Ser Gly Leu Ala Lys Thr Thr
    8000            8005            8010

Asp Met Leu His Lys Ser Ser Glu Pro Val Thr Asn Ser Pro Ala
    8015            8020            8025

Asn Leu Ser Ser Thr Ser Val Glu Ile Leu Ala Thr Ser Glu Val
    8030            8035            8040

Thr Thr Asp Thr Glu Lys Thr His Pro Ser Ser Asn Arg Thr Val
    8045            8050            8055

Thr Asp Val Gly Thr Ser Ser Gly His Glu Ser Thr Ser Phe
    8060            8065            8070

Val Leu Ala Asp Ser Gln Thr Ser Lys Val Thr Ser Pro Met Val
    8075            8080            8085
```

```
Ile Thr Ser Thr Met Glu Asp Thr Ser Val Ser Thr Ser Thr Pro
    8090            8095            8100

Gly Phe Phe Glu Thr Ser Arg Ile Gln Thr Glu Pro Thr Ser Ser
    8105            8110            8115

Leu Thr Leu Gly Leu Arg Lys Thr Ser Ser Glu Gly Thr Ser
    8120            8125            8130

Leu Ala Thr Glu Met Ser Thr Val Leu Ser Gly Val Pro Thr Gly
    8135            8140            8145

Ala Thr Ala Glu Val Ser Arg Thr Glu Val Thr Ser Ser Ser Arg
    8150            8155            8160

Thr Ser Ile Ser Gly Phe Ala Gln Leu Thr Val Ser Pro Glu Thr
    8165            8170            8175

Ser Thr Glu Thr Ile Thr Arg Leu Pro Thr Ser Ser Ile Met Thr
    8180            8185            8190

Glu Ser Ala Glu Met Met Ile Lys Thr Gln Thr Asp Pro Pro Gly
    8195            8200            8205

Ser Thr Pro Glu Ser Thr His Thr Val Asp Ile Ser Thr Thr Pro
    8210            8215            8220

Asn Trp Val Glu Thr His Ser Thr Val Thr Gln Arg Phe Ser His
    8225            8230            8235

Ser Glu Met Thr Thr Leu Val Ser Arg Ser Pro Gly Asp Met Leu
    8240            8245            8250

Trp Pro Ser Gln Ser Ser Val Glu Glu Thr Ser Ser Ala Ser Ser
    8255            8260            8265

Leu Leu Ser Leu Pro Ala Thr Thr Ser Pro Ser Pro Val Ser Ser
    8270            8275            8280

Thr Leu Val Glu Asp Phe Pro Ser Ala Ser Leu Pro Val Thr Ser
    8285            8290            8295

Leu Leu Asn Pro Gly Leu Val Ile Thr Thr Asp Arg Met Gly Ile
    8300            8305            8310

Ser Arg Glu Pro Gly Thr Ser Ser Thr Ser Asn Leu Ser Ser Thr
    8315            8320            8325

Ser His Glu Arg Leu Thr Thr Leu Glu Asp Thr Val Asp Thr Glu
    8330            8335            8340

Asp Met Gln Pro Ser Thr His Thr Ala Val Thr Asn Val Arg Thr
    8345            8350            8355

Ser Ile Ser Gly His Glu Ser Gln Ser Ser Val Leu Ser Asp Ser
    8360            8365            8370

Glu Thr Pro Lys Ala Thr Ser Pro Met Gly Thr Thr Tyr Thr Met
    8375            8380            8385

Gly Glu Thr Ser Val Ser Ile Ser Thr Ser Asp Phe Phe Glu Thr
    8390            8395            8400

Ser Arg Ile Gln Ile Glu Pro Thr Ser Ser Leu Thr Ser Gly Leu
    8405            8410            8415

Arg Glu Thr Ser Ser Ser Glu Arg Ile Ser Ser Ala Thr Glu Gly
    8420            8425            8430

Ser Thr Val Leu Ser Glu Val Pro Ser Gly Ala Thr Thr Glu Val
    8435            8440            8445

Ser Arg Thr Glu Val Ile Ser Ser Arg Gly Thr Ser Met Ser Gly
    8450            8455            8460

Pro Asp Gln Phe Thr Ile Ser Pro Asp Ile Ser Thr Glu Ala Ile
    8465            8470            8475

Thr Arg Leu Ser Thr Ser Pro Ile Met Thr Glu Ser Ala Glu Ser
```

```
                  8480              8485              8490
Ala Ile Thr Ile Glu Thr Gly Ser Pro Gly Ala Thr Ser Glu Gly
        8495              8500              8505
Thr Leu Thr Leu Asp Thr Ser Thr Thr Thr Phe Trp Ser Gly Thr
        8510              8515              8520
His Ser Thr Ala Ser Pro Gly Phe Ser His Ser Glu Met Thr Thr
        8525              8530              8535
Leu Met Ser Arg Thr Pro Gly Asp Val Pro Trp Pro Ser Leu Pro
        8540              8545              8550
Ser Val Glu Glu Ala Ser Ser Val Ser Ser Ser Leu Ser Ser Pro
        8555              8560              8565
Ala Met Thr Ser Thr Ser Phe Phe Ser Thr Leu Pro Glu Ser Ile
        8570              8575              8580
Ser Ser Ser Pro His Pro Val Thr Ala Leu Leu Thr Leu Gly Pro
        8585              8590              8595
Val Lys Thr Thr Asp Met Leu Arg Thr Ser Ser Glu Pro Glu Thr
        8600              8605              8610
Ser Ser Pro Pro Asn Leu Ser Ser Thr Ser Ala Glu Ile Leu Ala
        8615              8620              8625
Thr Ser Glu Val Thr Lys Asp Arg Glu Lys Ile His Pro Ser Ser
        8630              8635              8640
Asn Thr Pro Val Val Asn Val Gly Thr Val Ile Tyr Lys His Leu
        8645              8650              8655
Ser Pro Ser Ser Val Leu Ala Asp Leu Val Thr Thr Lys Pro Thr
        8660              8665              8670
Ser Pro Met Ala Thr Thr Ser Thr Leu Gly Asn Thr Ser Val Ser
        8675              8680              8685
Thr Ser Thr Pro Ala Phe Pro Glu Thr Met Met Thr Gln Pro Thr
        8690              8695              8700
Ser Ser Leu Thr Ser Gly Leu Arg Glu Ile Ser Thr Ser Gln Glu
        8705              8710              8715
Thr Ser Ser Ala Thr Glu Arg Ser Ala Ser Leu Ser Gly Met Pro
        8720              8725              8730
Thr Gly Ala Thr Thr Lys Val Ser Arg Thr Glu Ala Leu Ser Leu
        8735              8740              8745
Gly Arg Thr Ser Thr Pro Gly Pro Ala Gln Ser Thr Ile Ser Pro
        8750              8755              8760
Glu Ile Ser Thr Glu Thr Ile Thr Arg Ile Ser Thr Pro Leu Thr
        8765              8770              8775
Thr Thr Gly Ser Ala Glu Met Thr Ile Thr Pro Lys Thr Gly His
        8780              8785              8790
Ser Gly Ala Ser Ser Gln Gly Thr Phe Thr Leu Asp Thr Ser Ser
        8795              8800              8805
Arg Ala Ser Trp Pro Gly Thr His Ser Ala Ala Thr His Arg Ser
        8810              8815              8820
Pro His Ser Gly Met Thr Thr Pro Met Ser Arg Gly Pro Glu Asp
        8825              8830              8835
Val Ser Trp Pro Ser Arg Pro Ser Val Glu Lys Thr Ser Pro Pro
        8840              8845              8850
Ser Ser Leu Val Ser Leu Ala Val Thr Ser Pro Ser Pro Leu
        8855              8860              8865
Tyr Ser Thr Pro Ser Glu Ser Ser His Ser Ser Pro Leu Arg Val
        8870              8875              8880
```

-continued

```
Thr Ser Leu Phe Thr Pro Val Met Met Lys Thr Thr Asp Met Leu
8885                 8890            8895

Asp Thr Ser Leu Glu Pro Val Thr Thr Ser Pro Pro Ser Met Asn
8900                 8905            8910

Ile Thr Ser Asp Glu Ser Leu Ala Thr Ser Lys Ala Thr Met Glu
8915                 8920            8925

Thr Glu Ala Ile Gln Leu Ser Glu Asn Thr Ala Val Thr Gln Met
8930                 8935            8940

Gly Thr Ile Ser Ala Arg Gln Glu Phe Tyr Ser Ser Tyr Pro Gly
8945                 8950            8955

Leu Pro Glu Pro Ser Lys Val Thr Ser Pro Val Val Thr Ser Ser
8960                 8965            8970

Thr Ile Lys Asp Ile Val Ser Thr Thr Ile Pro Ala Ser Ser Glu
8975                 8980            8985

Ile Thr Arg Ile Glu Met Glu Ser Thr Ser Thr Leu Thr Pro Thr
8990                 8995            9000

Pro Arg Glu Thr Ser Thr Ser Gln Glu Ile His Ser Ala Thr Lys
9005                 9010            9015

Pro Ser Thr Val Pro Tyr Lys Ala Leu Thr Ser Ala Thr Ile Glu
9020                 9025            9030

Asp Ser Met Thr Gln Val Met Ser Ser Ser Arg Gly Pro Ser Pro
9035                 9040            9045

Asp Gln Ser Thr Met Ser Gln Asp Ile Ser Thr Glu Val Ile Thr
9050                 9055            9060

Arg Leu Ser Thr Ser Pro Ile Lys Thr Glu Ser Thr Glu Met Thr
9065                 9070            9075

Ile Thr Thr Gln Thr Gly Ser Pro Gly Ala Thr Ser Arg Gly Thr
9080                 9085            9090

Leu Thr Leu Asp Thr Ser Thr Thr Phe Met Ser Gly Thr His Ser
9095                 9100            9105

Thr Ala Ser Gln Gly Phe Ser His Ser Gln Met Thr Ala Leu Met
9110                 9115            9120

Ser Arg Thr Pro Gly Asp Val Pro Trp Leu Ser His Pro Ser Val
9125                 9130            9135

Glu Glu Ala Ser Ser Ala Ser Phe Ser Leu Ser Pro Val Met
9140                 9145            9150

Thr Ser Ser Ser Pro Val Ser Ser Thr Leu Pro Asp Ser Ile His
9155                 9160            9165

Ser Ser Ser Leu Pro Val Thr Ser Leu Leu Thr Ser Gly Leu Val
9170                 9175            9180

Lys Thr Thr Glu Leu Leu Gly Thr Ser Ser Glu Pro Glu Thr Ser
9185                 9190            9195

Ser Pro Pro Asn Leu Ser Ser Thr Ser Ala Glu Ile Leu Ala Ile
9200                 9205            9210

Thr Glu Val Thr Thr Asp Thr Glu Lys Leu Glu Met Thr Asn Val
9215                 9220            9225

Val Thr Ser Gly Tyr Thr His Glu Ser Pro Ser Ser Val Leu Ala
9230                 9235            9240

Asp Ser Val Thr Thr Lys Ala Thr Ser Ser Met Gly Ile Thr Tyr
9245                 9250            9255

Pro Thr Gly Asp Thr Asn Val Leu Thr Ser Thr Pro Ala Phe Ser
9260                 9265            9270
```

-continued

```
Asp Thr Ser Arg Ile Gln Thr Lys Ser Lys Leu Ser Leu Thr Pro
    9275             9280             9285
Gly Leu Met Glu Thr Ser Ile Ser Glu Glu Thr Ser Ser Ala Thr
    9290             9295             9300
Glu Lys Ser Thr Val Leu Ser Ser Val Pro Thr Gly Ala Thr Thr
    9305             9310             9315
Glu Val Ser Arg Thr Glu Ala Ile Ser Ser Ser Arg Thr Ser Ile
    9320             9325             9330
Pro Gly Pro Ala Gln Ser Thr Met Ser Ser Asp Thr Ser Met Glu
    9335             9340             9345
Thr Ile Thr Arg Ile Ser Thr Pro Leu Thr Arg Lys Glu Ser Thr
    9350             9355             9360
Asp Met Ala Ile Thr Pro Lys Thr Gly Pro Ser Gly Ala Thr Ser
    9365             9370             9375
Gln Gly Thr Phe Thr Leu Asp Ser Ser Ser Thr Ala Ser Trp Pro
    9380             9385             9390
Gly Thr His Ser Ala Thr Thr Gln Arg Phe Pro Gln Ser Val Val
    9395             9400             9405
Thr Thr Pro Met Ser Arg Gly Pro Glu Asp Val Ser Trp Pro Ser
    9410             9415             9420
Pro Leu Ser Val Glu Lys Asn Ser Pro Ser Ser Leu Val Ser
    9425             9430             9435
Ser Ser Ser Val Thr Ser Pro Ser Pro Leu Tyr Ser Thr Pro Ser
    9440             9445             9450
Gly Ser Ser His Ser Ser Pro Val Pro Val Thr Ser Leu Phe Thr
    9455             9460             9465
Ser Ile Met Met Lys Ala Thr Asp Met Leu Asp Ala Ser Leu Glu
    9470             9475             9480
Pro Glu Thr Thr Ser Ala Pro Asn Met Asn Ile Thr Ser Asp Glu
    9485             9490             9495
Ser Leu Ala Ala Ser Lys Ala Thr Thr Glu Thr Glu Ala Ile His
    9500             9505             9510
Val Phe Glu Asn Thr Ala Ala Ser His Val Glu Thr Thr Ser Ala
    9515             9520             9525
Thr Glu Glu Leu Tyr Ser Ser Pro Gly Phe Ser Glu Pro Thr
    9530             9535             9540
Lys Val Ile Ser Pro Val Val Thr Ser Ser Ser Ile Arg Asp Asn
    9545             9550             9555
Met Val Ser Thr Thr Met Pro Gly Ser Ser Gly Ile Thr Arg Ile
    9560             9565             9570
Glu Ile Glu Ser Met Ser Ser Leu Thr Pro Gly Leu Arg Glu Thr
    9575             9580             9585
Arg Thr Ser Gln Asp Ile Thr Ser Ser Glu Thr Ser Thr Val
    9590             9595             9600
Leu Tyr Lys Met Pro Ser Gly Ala Thr Pro Glu Val Ser Arg Thr
    9605             9610             9615
Glu Val Met Pro Ser Ser Arg Thr Ser Ile Pro Gly Pro Ala Gln
    9620             9625             9630
Ser Thr Met Ser Leu Asp Ile Ser Asp Glu Val Val Thr Arg Leu
    9635             9640             9645
Ser Thr Ser Pro Ile Met Thr Glu Ser Ala Glu Ile Thr Ile Thr
    9650             9655             9660
Thr Gln Thr Gly Tyr Ser Leu Ala Thr Ser Gln Val Thr Leu Pro
```

```
                      9665                9670                9675
Leu Gly Thr Ser Met Thr Phe Leu Ser Gly Thr His Ser Thr Met
    9680                9685                9690

Ser Gln Gly Leu Ser His Ser Glu Met Thr Asn Leu Met Ser Arg
    9695                9700                9705

Gly Pro Glu Ser Leu Ser Trp Thr Ser Pro Arg Phe Val Glu Thr
    9710                9715                9720

Thr Arg Ser Ser Ser Ser Leu Thr Ser Leu Pro Leu Thr Thr Ser
    9725                9730                9735

Leu Ser Pro Val Ser Ser Thr Leu Leu Asp Ser Ser Pro Ser Ser
    9740                9745                9750

Pro Leu Pro Val Thr Ser Leu Ile Leu Pro Gly Leu Val Lys Thr
    9755                9760                9765

Thr Glu Val Leu Asp Thr Ser Ser Glu Pro Lys Thr Ser Ser Ser
    9770                9775                9780

Pro Asn Leu Ser Ser Thr Ser Val Glu Ile Pro Ala Thr Ser Glu
    9785                9790                9795

Ile Met Thr Asp Thr Glu Lys Ile His Pro Ser Ser Asn Thr Ala
    9800                9805                9810

Val Ala Lys Val Arg Thr Ser Ser Ser Val His Glu Ser His Ser
    9815                9820                9825

Ser Val Leu Ala Asp Ser Glu Thr Thr Ile Thr Ile Pro Ser Met
    9830                9835                9840

Gly Ile Thr Ser Ala Val Asp Asp Thr Thr Val Phe Thr Ser Asn
    9845                9850                9855

Pro Ala Phe Ser Glu Thr Arg Arg Ile Pro Thr Glu Pro Thr Phe
    9860                9865                9870

Ser Leu Thr Pro Gly Phe Arg Glu Thr Ser Thr Ser Glu Glu Thr
    9875                9880                9885

Thr Ser Ile Thr Glu Thr Ser Ala Val Leu Tyr Gly Val Pro Thr
    9890                9895                9900

Ser Ala Thr Thr Glu Val Ser Met Thr Glu Ile Met Ser Ser Asn
    9905                9910                9915

Arg Ile His Ile Pro Asp Ser Asp Gln Ser Thr Met Ser Pro Asp
    9920                9925                9930

Ile Ile Thr Glu Val Ile Thr Arg Leu Ser Ser Ser Ser Met Met
    9935                9940                9945

Ser Glu Ser Thr Gln Met Thr Ile Thr Thr Gln Lys Ser Ser Pro
    9950                9955                9960

Gly Ala Thr Ala Gln Ser Thr Leu Thr Leu Ala Thr Thr Thr Ala
    9965                9970                9975

Pro Leu Ala Arg Thr His Ser Thr Val Pro Pro Arg Phe Leu His
    9980                9985                9990

Ser Glu Met Thr Thr Leu Met Ser Arg Ser Pro Glu Asn Pro Ser
    9995                10000               10005

Trp Lys Ser Ser Leu Phe Val Glu Lys Thr Ser Ser Ser Ser Ser
    10010               10015               10020

Leu Leu Ser Leu Pro Val Thr Thr Ser Pro Ser Val Ser Ser Thr
    10025               10030               10035

Leu Pro Gln Ser Ile Pro Ser Ser Ser Phe Ser Val Thr Ser Leu
    10040               10045               10050

Leu Thr Pro Gly Met Val Lys Thr Thr Asp Thr Ser Thr Glu Pro
    10055               10060               10065
```

```
Gly Thr Ser Leu Ser Pro Asn Leu Ser Gly Thr Ser Val Glu Ile
10070           10075               10080

Leu Ala Ala Ser Glu Val Thr Thr Asp Thr Glu Lys Ile His Pro
10085           10090               10095

Ser Ser Ser Met Ala Val Thr Asn Val Gly Thr Thr Ser Ser Gly
10100           10105               10110

His Glu Leu Tyr Ser Ser Val Ser Ile His Ser Glu Pro Ser Lys
10115           10120               10125

Ala Thr Tyr Pro Val Gly Thr Pro Ser Ser Met Ala Glu Thr Ser
10130           10135               10140

Ile Ser Thr Ser Met Pro Ala Asn Phe Glu Thr Thr Gly Phe Glu
10145           10150               10155

Ala Glu Pro Phe Ser His Leu Thr Ser Gly Phe Arg Lys Thr Asn
10160           10165               10170

Met Ser Leu Asp Thr Ser Ser Val Thr Pro Thr Asn Thr Pro Ser
10175           10180               10185

Ser Pro Gly Ser Thr His Leu Leu Gln Ser Ser Lys Thr Asp Phe
10190           10195               10200

Thr Ser Ser Ala Lys Thr Ser Ser Pro Asp Trp Pro Pro Ala Ser
10205           10210               10215

Gln Tyr Thr Glu Ile Pro Val Asp Ile Ile Thr Pro Phe Asn Ala
10220           10225               10230

Ser Pro Ser Ile Thr Glu Ser Thr Gly Ile Thr Ser Phe Pro Glu
10235           10240               10245

Ser Arg Phe Thr Met Ser Val Thr Glu Ser Thr His His Leu Ser
10250           10255               10260

Thr Asp Leu Leu Pro Ser Ala Glu Thr Ile Ser Thr Gly Thr Val
10265           10270               10275

Met Pro Ser Leu Ser Glu Ala Met Thr Ser Phe Ala Thr Thr Gly
10280           10285               10290

Val Pro Arg Ala Ile Ser Gly Ser Gly Ser Pro Phe Ser Arg Thr
10295           10300               10305

Glu Ser Gly Pro Gly Asp Ala Thr Leu Ser Thr Ile Ala Glu Ser
10310           10315               10320

Leu Pro Ser Ser Thr Pro Val Pro Phe Ser Ser Ser Thr Phe Thr
10325           10330               10335

Thr Thr Asp Ser Ser Thr Ile Pro Ala Leu His Glu Ile Thr Ser
10340           10345               10350

Ser Ser Ala Thr Pro Tyr Arg Val Asp Thr Ser Leu Gly Thr Glu
10355           10360               10365

Ser Ser Thr Thr Glu Gly Arg Leu Val Met Val Ser Thr Leu Asp
10370           10375               10380

Thr Ser Ser Gln Pro Gly Arg Thr Ser Ser Pro Ile Leu Asp
10385           10390               10395

Thr Arg Met Thr Glu Ser Val Glu Leu Gly Thr Val Thr Ser Ala
10400           10405               10410

Tyr Gln Val Pro Ser Leu Ser Thr Arg Leu Thr Arg Thr Asp Gly
10415           10420               10425

Ile Met Glu His Ile Thr Lys Ile Pro Asn Glu Ala Ala His Arg
10430           10435               10440

Gly Thr Ile Arg Pro Val Lys Gly Pro Gln Thr Ser Thr Ser Pro
10445           10450               10455
```

-continued

| | | | | | | | | | | | |
|---|---|---|---|---|---|---|---|---|---|---|---|
| Ala | Ser | Pro | Lys | Gly | Leu | His | Thr | Gly | Gly | Thr | Lys | Arg | Met | Glu |
| | 10460 | | | | | 10465 | | | | | 10470 | | | |
| Thr | Thr | Thr | Thr | Ala | Leu | Lys | Thr | Thr | Thr | Thr | Ala | Leu | Lys | Thr |
| | 10475 | | | | | 10480 | | | | | 10485 | | | |
| Thr | Ser | Arg | Ala | Thr | Leu | Thr | Thr | Ser | Val | Tyr | Thr | Pro | Thr | Leu |
| | 10490 | | | | | 10495 | | | | | 10500 | | | |
| Gly | Thr | Leu | Thr | Pro | Leu | Asn | Ala | Ser | Met | Gln | Met | Ala | Ser | Thr |
| | 10505 | | | | | 10510 | | | | | 10515 | | | |
| Ile | Pro | Thr | Glu | Met | Met | Ile | Thr | Thr | Pro | Tyr | Val | Phe | Pro | Asp |
| | 10520 | | | | | 10525 | | | | | 10530 | | | |
| Val | Pro | Glu | Thr | Thr | Ser | Ser | Leu | Ala | Thr | Ser | Leu | Gly | Ala | Glu |
| | 10535 | | | | | 10540 | | | | | 10545 | | | |
| Thr | Ser | Thr | Ala | Leu | Pro | Arg | Thr | Thr | Pro | Ser | Val | Phe | Asn | Arg |
| | 10550 | | | | | 10555 | | | | | 10560 | | | |
| Glu | Ser | Glu | Thr | Thr | Ala | Ser | Leu | Val | Ser | Arg | Ser | Gly | Ala | Glu |
| | 10565 | | | | | 10570 | | | | | 10575 | | | |
| Arg | Ser | Pro | Val | Ile | Gln | Thr | Leu | Asp | Val | Ser | Ser | Ser | Glu | Pro |
| | 10580 | | | | | 10585 | | | | | 10590 | | | |
| Asp | Thr | Thr | Ala | Ser | Trp | Val | Ile | His | Pro | Ala | Glu | Thr | Ile | Pro |
| | 10595 | | | | | 10600 | | | | | 10605 | | | |
| Thr | Val | Ser | Lys | Thr | Thr | Pro | Asn | Phe | Phe | His | Ser | Glu | Leu | Asp |
| | 10610 | | | | | 10615 | | | | | 10620 | | | |
| Thr | Val | Ser | Ser | Thr | Ala | Thr | Ser | His | Gly | Ala | Asp | Val | Ser | Ser |
| | 10625 | | | | | 10630 | | | | | 10635 | | | |
| Ala | Ile | Pro | Thr | Asn | Ile | Ser | Pro | Ser | Glu | Leu | Asp | Ala | Leu | Thr |
| | 10640 | | | | | 10645 | | | | | 10650 | | | |
| Pro | Leu | Val | Thr | Ile | Ser | Gly | Thr | Asp | Thr | Ser | Thr | Thr | Phe | Pro |
| | 10655 | | | | | 10660 | | | | | 10665 | | | |
| Thr | Leu | Thr | Lys | Ser | Pro | His | Glu | Thr | Glu | Thr | Arg | Thr | Thr | Trp |
| | 10670 | | | | | 10675 | | | | | 10680 | | | |
| Leu | Thr | His | Pro | Ala | Glu | Thr | Ser | Ser | Thr | Ile | Pro | Arg | Thr | Ile |
| | 10685 | | | | | 10690 | | | | | 10695 | | | |
| Pro | Asn | Phe | Ser | His | His | Glu | Ser | Asp | Ala | Thr | Pro | Ser | Ile | Ala |
| | 10700 | | | | | 10705 | | | | | 10710 | | | |
| Thr | Ser | Pro | Gly | Ala | Glu | Thr | Ser | Ser | Ala | Ile | Pro | Ile | Met | Thr |
| | 10715 | | | | | 10720 | | | | | 10725 | | | |
| Val | Ser | Pro | Gly | Ala | Glu | Asp | Leu | Val | Thr | Ser | Gln | Val | Thr | Ser |
| | 10730 | | | | | 10735 | | | | | 10740 | | | |
| Ser | Gly | Thr | Asp | Arg | Asn | Met | Thr | Ile | Pro | Thr | Leu | Thr | Leu | Ser |
| | 10745 | | | | | 10750 | | | | | 10755 | | | |
| Pro | Gly | Glu | Pro | Lys | Thr | Ile | Ala | Ser | Leu | Val | Thr | His | Pro | Glu |
| | 10760 | | | | | 10765 | | | | | 10770 | | | |
| Ala | Gln | Thr | Ser | Ser | Ala | Ile | Pro | Thr | Ser | Thr | Ile | Ser | Pro | Ala |
| | 10775 | | | | | 10780 | | | | | 10785 | | | |
| Val | Ser | Arg | Leu | Val | Thr | Ser | Met | Val | Thr | Ser | Leu | Ala | Ala | Lys |
| | 10790 | | | | | 10795 | | | | | 10800 | | | |
| Thr | Ser | Thr | Thr | Asn | Arg | Ala | Leu | Thr | Asn | Ser | Pro | Gly | Glu | Pro |
| | 10805 | | | | | 10810 | | | | | 10815 | | | |
| Ala | Thr | Thr | Val | Ser | Leu | Val | Thr | His | Pro | Ala | Gln | Thr | Ser | Pro |
| | 10820 | | | | | 10825 | | | | | 10830 | | | |
| Thr | Val | Pro | Trp | Thr | Thr | Ser | Ile | Phe | Phe | His | Ser | Lys | Ser | Asp |
| | 10835 | | | | | 10840 | | | | | 10845 | | | |
| Thr | Thr | Pro | Ser | Met | Thr | Thr | Ser | His | Gly | Ala | Glu | Ser | Ser | Ser |

```
                10850              10855              10860
Ala Val Pro Thr Pro Thr Val Ser Thr Glu Val Pro Gly Val Val
                10865              10870              10875
Thr Pro Leu Val Thr Ser Ser Arg Ala Val Ile Ser Thr Thr Ile
                10880              10885              10890
Pro Ile Leu Thr Leu Ser Pro Gly Glu Pro Glu Thr Thr Pro Ser
                10895              10900              10905
Met Ala Thr Ser His Gly Glu Glu Ala Ser Ser Ala Ile Pro Thr
                10910              10915              10920
Pro Thr Val Ser Pro Gly Val Pro Gly Val Val Thr Ser Leu Val
                10925              10930              10935
Thr Ser Ser Arg Ala Val Thr Ser Thr Thr Ile Pro Ile Leu Thr
                10940              10945              10950
Phe Ser Leu Gly Glu Pro Glu Thr Thr Pro Ser Met Ala Thr Ser
                10955              10960              10965
His Gly Thr Glu Ala Gly Ser Ala Val Pro Thr Val Leu Pro Glu
                10970              10975              10980
Val Pro Gly Met Val Thr Ser Leu Val Ala Ser Ser Arg Ala Val
                10985              10990              10995
Thr Ser Thr Thr Leu Pro Thr Leu Thr Leu Ser Pro Gly Glu Pro
                11000              11005              11010
Glu Thr Thr Pro Ser Met Ala Thr Ser His Gly Ala Glu Ala Ser
                11015              11020              11025
Ser Thr Val Pro Thr Val Ser Pro Glu Val Pro Gly Val Val Thr
                11030              11035              11040
Ser Leu Val Thr Ser Ser Ser Gly Val Asn Ser Thr Ser Ile Pro
                11045              11050              11055
Thr Leu Ile Leu Ser Pro Gly Glu Leu Glu Thr Thr Pro Ser Met
                11060              11065              11070
Ala Thr Ser His Gly Ala Glu Ala Ser Ser Ala Val Pro Thr Pro
                11075              11080              11085
Thr Val Ser Pro Gly Val Ser Gly Val Val Thr Pro Leu Val Thr
                11090              11095              11100
Ser Ser Arg Ala Val Thr Ser Thr Thr Ile Pro Ile Leu Thr Leu
                11105              11110              11115
Ser Ser Ser Glu Pro Glu Thr Thr Pro Ser Met Ala Thr Ser His
                11120              11125              11130
Gly Val Glu Ala Ser Ser Ala Val Leu Thr Val Ser Pro Glu Val
                11135              11140              11145
Pro Gly Met Val Thr Ser Leu Val Thr Ser Ser Arg Ala Val Thr
                11150              11155              11160
Ser Thr Thr Ile Pro Thr Leu Thr Ile Ser Ser Asp Glu Pro Glu
                11165              11170              11175
Thr Thr Thr Ser Leu Val Thr His Ser Glu Ala Lys Met Ile Ser
                11180              11185              11190
Ala Ile Pro Thr Leu Ala Val Ser Pro Thr Val Gln Gly Leu Val
                11195              11200              11205
Thr Ser Leu Val Thr Ser Ser Gly Ser Glu Thr Ser Ala Phe Ser
                11210              11215              11220
Asn Leu Thr Val Ala Ser Ser Gln Pro Glu Thr Ile Asp Ser Trp
                11225              11230              11235
Val Ala His Pro Gly Thr Glu Ala Ser Ser Val Val Pro Thr Leu
                11240              11245              11250
```

```
Thr Val Ser Thr Gly Glu Pro Phe Thr Asn Ile Ser Leu Val Thr
    11255           11260               11265

His Pro Ala Glu Ser Ser Thr Leu Pro Arg Thr Thr Ser Arg
    11270           11275               11280

Phe Ser His Ser Glu Leu Asp Thr Met Pro Ser Thr Val Thr Ser
    11285           11290               11295

Pro Glu Ala Glu Ser Ser Ala Ile Ser Thr Thr Ile Ser Pro
    11300           11305               11310

Gly Ile Pro Gly Val Leu Thr Ser Leu Val Thr Ser Ser Gly Arg
    11315           11320               11325

Asp Ile Ser Ala Thr Phe Pro Thr Val Pro Glu Ser Pro His Glu
    11330           11335               11340

Ser Glu Ala Thr Ala Ser Trp Val Thr His Pro Ala Val Thr Ser
    11345           11350               11355

Thr Thr Val Pro Arg Thr Thr Pro Asn Tyr Ser His Ser Glu Pro
    11360           11365               11370

Asp Thr Thr Pro Ser Ile Ala Thr Ser Pro Gly Ala Glu Ala Thr
    11375           11380               11385

Ser Asp Phe Pro Thr Ile Thr Val Ser Pro Asp Val Pro Asp Met
    11390           11395               11400

Val Thr Ser Gln Val Thr Ser Ser Gly Thr Asp Thr Ser Ile Thr
    11405           11410               11415

Ile Pro Thr Leu Thr Leu Ser Ser Gly Glu Pro Glu Thr Thr Thr
    11420           11425               11430

Ser Phe Ile Thr Tyr Ser Glu Thr His Thr Ser Ser Ala Ile Pro
    11435           11440               11445

Thr Leu Pro Val Ser Pro Gly Ala Ser Lys Met Leu Thr Ser Leu
    11450           11455               11460

Val Ile Ser Ser Gly Thr Asp Ser Thr Thr Thr Phe Pro Thr Leu
    11465           11470               11475

Thr Glu Thr Pro Tyr Glu Pro Glu Thr Thr Ala Ile Gln Leu Ile
    11480           11485               11490

His Pro Ala Glu Thr Asn Thr Met Val Pro Arg Thr Thr Pro Lys
    11495           11500               11505

Phe Ser His Ser Lys Ser Asp Thr Thr Leu Pro Val Ala Ile Thr
    11510           11515               11520

Ser Pro Gly Pro Glu Ala Ser Ser Ala Val Ser Thr Thr Thr Ile
    11525           11530               11535

Ser Pro Asp Met Ser Asp Leu Val Thr Ser Leu Val Pro Ser Ser
    11540           11545               11550

Gly Thr Asp Thr Ser Thr Thr Phe Pro Thr Leu Ser Glu Thr Pro
    11555           11560               11565

Tyr Glu Pro Glu Thr Thr Ala Thr Trp Leu Thr His Pro Ala Glu
    11570           11575               11580

Thr Ser Thr Thr Val Ser Gly Thr Ile Pro Asn Phe Ser His Arg
    11585           11590               11595

Gly Ser Asp Thr Ala Pro Ser Met Val Thr Ser Pro Gly Val Asp
    11600           11605               11610

Thr Arg Ser Gly Val Pro Thr Thr Thr Ile Pro Pro Ser Ile Pro
    11615           11620               11625

Gly Val Val Thr Ser Gln Val Thr Ser Ser Ala Thr Asp Thr Ser
    11630           11635               11640
```

-continued

```
Thr Ala Ile Pro Thr Leu Thr  Pro Ser Pro Gly Glu  Pro Glu Thr
    11645            11650              11655

Thr Ala Ser Ser Ala Thr His  Pro Gly Thr Gln Thr   Gly Phe Thr
    11660            11665              11670

Val Pro Ile Arg Thr Val Pro  Ser Ser Glu Pro Asp   Thr Met Ala
    11675            11680              11685

Ser Trp Val Thr His Pro Pro  Gln Thr Ser Thr Pro   Val Ser Arg
    11690            11695              11700

Thr Thr Ser Ser Phe Ser His  Ser Ser Pro Asp Ala   Thr Pro Val
    11705            11710              11715

Met Ala Thr Ser Pro Arg Thr  Glu Ala Ser Ser Ala   Val Leu Thr
    11720            11725              11730

Thr Ile Ser Pro Gly Ala Pro  Glu Met Val Thr Ser   Gln Ile Thr
    11735            11740              11745

Ser Ser Gly Ala Ala Thr Ser  Thr Thr Val Pro Thr   Leu Thr His
    11750            11755              11760

Ser Pro Gly Met Pro Glu Thr  Thr Ala Leu Leu Ser   Thr His Pro
    11765            11770              11775

Arg Thr Glu Thr Ser Lys Thr  Phe Pro Ala Ser Thr   Val Phe Pro
    11780            11785              11790

Gln Val Ser Glu Thr Thr Ala  Ser Leu Thr Ile Arg   Pro Gly Ala
    11795            11800              11805

Glu Thr Ser Thr Ala Leu Pro  Thr Gln Thr Thr Ser   Ser Leu Phe
    11810            11815              11820

Thr Leu Leu Val Thr Gly Thr  Ser Arg Val Asp Leu   Ser Pro Thr
    11825            11830              11835

Ala Ser Pro Gly Val Ser Ala  Lys Thr Ala Pro Leu   Ser Thr His
    11840            11845              11850

Pro Gly Thr Glu Thr Ser Thr  Met Ile Pro Thr Ser   Thr Leu Ser
    11855            11860              11865

Leu Gly Leu Leu Glu Thr Thr  Gly Leu Leu Ala Thr   Ser Ser Ser
    11870            11875              11880

Ala Glu Thr Ser Thr Ser Thr  Leu Thr Leu Thr Val   Ser Pro Ala
    11885            11890              11895

Val Ser Gly Leu Ser Ser Ala  Ser Ile Thr Thr Asp   Lys Pro Gln
    11900            11905              11910

Thr Val Thr Ser Trp Asn Thr  Glu Thr Ser Pro Ser   Val Thr Ser
    11915            11920              11925

Val Gly Pro Pro Glu Phe Ser  Arg Thr Val Thr Gly   Thr Thr Met
    11930            11935              11940

Thr Leu Ile Pro Ser Glu Met  Pro Thr Pro Pro Lys   Thr Ser His
    11945            11950              11955

Gly Glu Gly Val Ser Pro Thr  Thr Ile Leu Arg Thr   Thr Met Val
    11960            11965              11970

Glu Ala Thr Asn Leu Ala Thr  Thr Gly Ser Ser Pro   Thr Val Ala
    11975            11980              11985

Lys Thr Thr Thr Phe Asn Thr  Thr Leu Ala Gly Ser   Leu Phe Thr
    11990            11995              12000

Pro Leu Thr Thr Pro Gly Met  Ser Thr Leu Ala Ser   Glu Ser Val
    12005            12010              12015

Thr Ser Arg Thr Ser Tyr Asn  His Arg Ser Trp Ile   Ser Thr Thr
    12020            12025              12030

Ser Ser     Tyr Asn Arg Arg Tyr  Trp Thr Pro Ala Thr   Ser Thr Pro
```

-continued

|   |   |   |   |   |   |   |   |   |   |   |   |   |   |   |
|---|---|---|---|---|---|---|---|---|---|---|---|---|---|---|
|   |   | 12035 |   |   |   | 12040 |   |   |   | 12045 |   |   |   |   |
| Val | Thr | Ser | Thr | Phe | Ser | Pro | Gly | Ile | Ser | Thr | Ser | Ser | Ile | Pro |
|   |   | 12050 |   |   |   | 12055 |   |   |   | 12060 |   |   |   |   |
| Ser | Ser | Thr | Ala | Ala | Thr | Val | Pro | Phe | Met | Val | Pro | Phe | Thr | Leu |
|   |   | 12065 |   |   |   | 12070 |   |   |   | 12075 |   |   |   |   |
| Asn | Phe | Thr | Ile | Thr | Asn | Leu | Gln | Tyr | Glu | Glu | Asp | Met | Arg | His |
|   |   | 12080 |   |   |   | 12085 |   |   |   | 12090 |   |   |   |   |
| Pro | Gly | Ser | Arg | Lys | Phe | Asn | Ala | Thr | Glu | Arg | Glu | Leu | Gln | Gly |
|   |   | 12095 |   |   |   | 12100 |   |   |   | 12105 |   |   |   |   |
| Leu | Leu | Lys | Pro | Leu | Phe | Arg | Asn | Ser | Ser | Leu | Glu | Tyr | Leu | Tyr |
|   |   | 12110 |   |   |   | 12115 |   |   |   | 12120 |   |   |   |   |
| Ser | Gly | Cys | Arg | Leu | Ala | Ser | Leu | Arg | Pro | Glu | Lys | Asp | Ser | Ser |
|   |   | 12125 |   |   |   | 12130 |   |   |   | 12135 |   |   |   |   |
| Ala | Thr | Ala | Val | Asp | Ala | Ile | Cys | Thr | His | Arg | Pro | Asp | Pro | Glu |
|   |   | 12140 |   |   |   | 12145 |   |   |   | 12150 |   |   |   |   |
| Asp | Leu | Gly | Leu | Asp | Arg | Glu | Arg | Leu | Tyr | Trp | Glu | Leu | Ser | Asn |
|   |   | 12155 |   |   |   | 12160 |   |   |   | 12165 |   |   |   |   |
| Leu | Thr | Asn | Gly | Ile | Gln | Glu | Leu | Gly | Pro | Tyr | Thr | Leu | Asp | Arg |
|   |   | 12170 |   |   |   | 12175 |   |   |   | 12180 |   |   |   |   |
| Asn | Ser | Leu | Tyr | Val | Asn | Gly | Phe | Thr | His | Arg | Ser | Ser | Met | Pro |
|   |   | 12185 |   |   |   | 12190 |   |   |   | 12195 |   |   |   |   |
| Thr | Thr | Ser | Thr | Pro | Gly | Thr | Ser | Thr | Val | Asp | Val | Gly | Thr | Ser |
|   |   | 12200 |   |   |   | 12205 |   |   |   | 12210 |   |   |   |   |
| Gly | Thr | Pro | Ser | Ser | Ser | Pro | Ser | Pro | Thr | Thr | Ala | Gly | Pro | Leu |
|   |   | 12215 |   |   |   | 12220 |   |   |   | 12225 |   |   |   |   |
| Leu | Met | Pro | Phe | Thr | Leu | Asn | Phe | Thr | Ile | Thr | Asn | Leu | Gln | Tyr |
|   |   | 12230 |   |   |   | 12235 |   |   |   | 12240 |   |   |   |   |
| Glu | Glu | Asp | Met | Arg | Arg | Thr | Gly | Ser | Arg | Lys | Phe | Asn | Thr | Met |
|   |   | 12245 |   |   |   | 12250 |   |   |   | 12255 |   |   |   |   |
| Glu | Ser | Val | Leu | Gln | Gly | Leu | Leu | Lys | Pro | Leu | Phe | Lys | Asn | Thr |
|   |   | 12260 |   |   |   | 12265 |   |   |   | 12270 |   |   |   |   |
| Ser | Val | Gly | Pro | Leu | Tyr | Ser | Gly | Cys | Arg | Leu | Thr | Leu | Leu | Arg |
|   |   | 12275 |   |   |   | 12280 |   |   |   | 12285 |   |   |   |   |
| Pro | Glu | Lys | Asp | Gly | Ala | Ala | Thr | Gly | Val | Asp | Ala | Ile | Cys | Thr |
|   |   | 12290 |   |   |   | 12295 |   |   |   | 12300 |   |   |   |   |
| His | Arg | Leu | Asp | Pro | Lys | Ser | Pro | Gly | Leu | Asn | Arg | Glu | Gln | Leu |
|   |   | 12305 |   |   |   | 12310 |   |   |   | 12315 |   |   |   |   |
| Tyr | Trp | Glu | Leu | Ser | Lys | Leu | Thr | Asn | Asp | Ile | Glu | Glu | Leu | Gly |
|   |   | 12320 |   |   |   | 12325 |   |   |   | 12330 |   |   |   |   |
| Pro | Tyr | Thr | Leu | Asp | Arg | Asn | Ser | Leu | Tyr | Val | Asn | Gly | Phe | Thr |
|   |   | 12335 |   |   |   | 12340 |   |   |   | 12345 |   |   |   |   |
| His | Gln | Ser | Ser | Val | Ser | Thr | Thr | Ser | Thr | Pro | Gly | Thr | Ser | Thr |
|   |   | 12350 |   |   |   | 12355 |   |   |   | 12360 |   |   |   |   |
| Val | Asp | Leu | Arg | Thr | Ser | Gly | Thr | Pro | Ser | Ser | Leu | Ser | Ser | Pro |
|   |   | 12365 |   |   |   | 12370 |   |   |   | 12375 |   |   |   |   |
| Thr | Ile | Met | Ala | Ala | Gly | Pro | Leu | Leu | Val | Pro | Phe | Thr | Leu | Asn |
|   |   | 12380 |   |   |   | 12385 |   |   |   | 12390 |   |   |   |   |
| Phe | Thr | Ile | Thr | Asn | Leu | Gln | Tyr | Gly | Glu | Asp | Met | Gly | His | Pro |
|   |   | 12395 |   |   |   | 12400 |   |   |   | 12405 |   |   |   |   |
| Gly | Ser | Arg | Lys | Phe | Asn | Thr | Thr | Glu | Arg | Val | Leu | Gln | Gly | Leu |
|   |   | 12410 |   |   |   | 12415 |   |   |   | 12420 |   |   |   |   |
| Leu | Gly | Pro | Ile | Phe | Lys | Asn | Thr | Ser | Val | Gly | Pro | Leu | Tyr | Ser |
|   |   | 12425 |   |   |   | 12430 |   |   |   | 12435 |   |   |   |   |

```
Gly Cys Arg Leu Thr Ser Leu Arg Ser Glu Lys Asp     Gly Ala Ala
    12440               12445               12450

Thr Gly Val Asp Ala Ile Cys Ile His His Leu Asp     Pro Lys Ser
    12455               12460               12465

Pro Gly Leu Asn Arg Glu Arg Leu Tyr Trp Glu Leu     Ser Gln Leu
    12470               12475               12480

Thr Asn Gly Ile Lys Glu Leu Gly Pro Tyr Thr Leu     Asp Arg Asn
    12485               12490               12495

Ser Leu Tyr Val Asn Gly Phe Thr His Arg Thr Ser     Val Pro Thr
    12500               12505               12510

Ser Ser Thr Pro Gly Thr Ser Thr Val Asp Leu Gly     Thr Ser Gly
    12515               12520               12525

Thr Pro Phe Ser Leu Pro Ser Pro Ala Thr Ala Gly     Pro Leu Leu
    12530               12535               12540

Val Leu Phe Thr Leu Asn Phe Thr Ile Thr Asn Leu     Lys Tyr Glu
    12545               12550               12555

Glu Asp Met His Arg Pro Gly Ser Arg Lys Phe Asn     Thr Thr Glu
    12560               12565               12570

Arg Val Leu Gln Thr Leu Leu Gly Pro Met Phe Lys     Asn Thr Ser
    12575               12580               12585

Val Gly Leu Leu Tyr Ser Gly Cys Arg Leu Thr Leu     Leu Arg Ser
    12590               12595               12600

Glu Lys Asp Gly Ala Ala Thr Gly Val Asp Ala Ile     Cys Thr His
    12605               12610               12615

Arg Leu Asp Pro Lys Ser Pro Gly Val Asp Arg Glu     Gln Leu Tyr
    12620               12625               12630

Trp Glu Leu Ser Gln Leu Thr Asn Gly Ile Lys Glu     Leu Gly Pro
    12635               12640               12645

Tyr Thr Leu Asp Arg Asn Ser Leu Tyr Val Asn Gly     Phe Thr His
    12650               12655               12660

Trp Ile Pro Val Pro Thr Ser Ser Thr Pro Gly Thr     Ser Thr Val
    12665               12670               12675

Asp Leu Gly Ser Gly Thr Pro Ser Ser Leu Pro Ser     Pro Thr Thr
    12680               12685               12690

Ala Gly Pro Leu Leu Val Pro Phe Thr Leu Asn Phe     Thr Ile Thr
    12695               12700               12705

Asn Leu Lys Tyr Glu Glu Asp Met His Cys Pro Gly     Ser Arg Lys
    12710               12715               12720

Phe Asn Thr Thr Glu Arg Val Leu Gln Ser Leu Leu     Gly Pro Met
    12725               12730               12735

Phe Lys Asn Thr Ser Val Gly Pro Leu Tyr Ser Gly     Cys Arg Leu
    12740               12745               12750

Thr Leu Leu Arg Ser Glu Lys Asp Gly Ala Ala Thr     Gly Val Asp
    12755               12760               12765

Ala Ile Cys Thr His Arg Leu Asp Pro Lys Ser Pro     Gly Val Asp
    12770               12775               12780

Arg Glu Gln Leu Tyr Trp Glu Leu Ser Gln Leu Thr     Asn Gly Ile
    12785               12790               12795

Lys Glu Leu Gly Pro Tyr Thr Leu Asp Arg Asn Ser     Leu Tyr Val
    12800               12805               12810

Asn Gly Phe Thr His Gln Thr Ser Ala Pro Asn Thr     Ser Thr Pro
    12815               12820               12825
```

```
Gly Thr Ser Thr Val Asp Leu Gly Thr Ser Gly Thr Pro Ser Ser
    12830             12835             12840

Leu Pro Ser Pro Thr Ser Ala Gly Pro Leu Leu Val Pro Phe Thr
    12845             12850             12855

Leu Asn Phe Thr Ile Thr Asn Leu Gln Tyr Glu Glu Asp Met His
    12860             12865             12870

His Pro Gly Ser Arg Lys Phe Asn Thr Thr Glu Arg Val Leu Gln
    12875             12880             12885

Gly Leu Leu Gly Pro Met Phe Lys Asn Thr Ser Val Gly Leu Leu
    12890             12895             12900

Tyr Ser Gly Cys Arg Leu Thr Leu Leu Arg Pro Glu Lys Asn Gly
    12905             12910             12915

Ala Ala Thr Gly Met Asp Ala Ile Cys Ser His Arg Leu Asp Pro
    12920             12925             12930

Lys Ser Pro Gly Leu Asn Arg Glu Gln Leu Tyr Trp Glu Leu Ser
    12935             12940             12945

Gln Leu Thr His Gly Ile Lys Glu Leu Gly Pro Tyr Thr Leu Asp
    12950             12955             12960

Arg Asn Ser Leu Tyr Val Asn Gly Phe Thr His Arg Ser Ser Val
    12965             12970             12975

Ala Pro Thr Ser Thr Pro Gly Thr Ser Thr Val Asp Leu Gly Thr
    12980             12985             12990

Ser Gly Thr Pro Ser Ser Leu Pro Ser Pro Thr Thr Ala Val Pro
    12995             13000             13005

Leu Leu Val Pro Phe Thr Leu Asn Phe Thr Ile Thr Asn Leu Gln
    13010             13015             13020

Tyr Gly Glu Asp Met Arg His Pro Gly Ser Arg Lys Phe Asn Thr
    13025             13030             13035

Thr Glu Arg Val Leu Gln Gly Leu Leu Gly Pro Leu Phe Lys Asn
    13040             13045             13050

Ser Ser Val Gly Pro Leu Tyr Ser Gly Cys Arg Leu Ile Ser Leu
    13055             13060             13065

Arg Ser Glu Lys Asp Gly Ala Ala Thr Gly Val Asp Ala Ile Cys
    13070             13075             13080

Thr His His Leu Asn Pro Gln Ser Pro Gly Leu Asp Arg Glu Gln
    13085             13090             13095

Leu Tyr Trp Gln Leu Ser Gln Met Thr Asn Gly Ile Lys Glu Leu
    13100             13105             13110

Gly Pro Tyr Thr Leu Asp Arg Asn Ser Leu Tyr Val Asn Gly Phe
    13115             13120             13125

Thr His Arg Ser Ser Gly Leu Thr Thr Ser Thr Pro Trp Thr Ser
    13130             13135             13140

Thr Val Asp Leu Gly Thr Ser Gly Thr Pro Ser Pro Val Pro Ser
    13145             13150             13155

Pro Thr Thr Thr Gly Pro Leu Leu Val Pro Phe Thr Leu Asn Phe
    13160             13165             13170

Thr Ile Thr Asn Leu Gln Tyr Glu Glu Asn Met Gly His Pro Gly
    13175             13180             13185

Ser Arg Lys Phe Asn Ile Thr Glu Ser Val Leu Gln Gly Leu Leu
    13190             13195             13200

Lys Pro Leu Phe Lys Ser Thr Ser Val Gly Pro Leu Tyr Ser Gly
    13205             13210             13215

Cys Arg Leu Thr Leu Leu Arg Pro Glu Lys Asp Gly Val Ala Thr
```

```
                13220                    13225                    13230
Arg Val     Asp Ala Ile Cys Thr     His Arg Pro Asp Pro     Lys Ile Pro
    13235                    13240                    13245

Gly Leu     Asp Arg Gln Gln Leu     Tyr Trp Glu Leu Ser     Gln Leu Thr
    13250                    13255                    13260

His Ser     Ile Thr Glu Leu Gly     Pro Tyr Thr Leu Asp     Arg Asp Ser
    13265                    13270                    13275

Leu Tyr     Val Asn Gly Phe Thr     Gln Arg Ser Ser Val     Pro Thr Thr
    13280                    13285                    13290

Ser Thr     Pro Gly Thr Phe Thr     Val Gln Pro Glu Thr     Ser Glu Thr
    13295                    13300                    13305

Pro Ser     Ser Leu Pro Gly Pro     Thr Ala Thr Gly Pro     Val Leu Leu
    13310                    13315                    13320

Pro Phe     Thr Leu Asn Phe Thr     Ile Thr Asn Leu Gln     Tyr Glu Glu
    13325                    13330                    13335

Asp Met     Arg Arg Pro Gly Ser     Arg Lys Phe Asn Thr     Thr Glu Arg
    13340                    13345                    13350

Val Leu     Gln Gly Leu Leu Met     Pro Leu Phe Lys Asn     Thr Ser Val
    13355                    13360                    13365

Ser Ser     Leu Tyr Ser Gly Cys     Arg Leu Thr Leu Leu     Arg Pro Glu
    13370                    13375                    13380

Lys Asp     Gly Ala Ala Thr Arg     Val Asp Ala Val Cys     Thr His Arg
    13385                    13390                    13395

Pro Asp     Pro Lys Ser Pro Gly     Leu Asp Arg Glu Arg     Leu Tyr Trp
    13400                    13405                    13410

Lys Leu     Ser Gln Leu Thr His     Gly Ile Thr Glu Leu     Gly Pro Tyr
    13415                    13420                    13425

Thr Leu     Asp Arg His Ser Leu     Tyr Val Asn Gly Phe     Thr His Gln
    13430                    13435                    13440

Ser Ser     Met Thr Thr Thr Arg     Thr Pro Asp Thr Ser     Thr Met His
    13445                    13450                    13455

Leu Ala     Thr Ser Arg Thr Pro     Ala Ser Leu Ser Gly     Pro Met Thr
    13460                    13465                    13470

Ala Ser     Pro Leu Leu Val Leu     Phe Thr Ile Asn Phe     Thr Ile Thr
    13475                    13480                    13485

Asn Leu     Arg Tyr Glu Glu Asn     Met His His Pro Gly     Ser Arg Lys
    13490                    13495                    13500

Phe Asn     Thr Thr Glu Arg Val     Leu Gln Gly Leu Leu     Arg Pro Val
    13505                    13510                    13515

Phe Lys     Asn Thr Ser Val Gly     Pro Leu Tyr Ser Gly     Cys Arg Leu
    13520                    13525                    13530

Thr Leu     Leu Arg Pro Lys Lys     Asp Gly Ala Ala Thr     Lys Val Asp
    13535                    13540                    13545

Ala Ile     Cys Thr Tyr Arg Pro     Asp Pro Lys Ser Pro     Gly Leu Asp
    13550                    13555                    13560

Arg Glu     Gln Leu Tyr Trp Glu     Leu Ser Gln Leu Thr     His Ser Ile
    13565                    13570                    13575

Thr Glu     Leu Gly Pro Tyr Thr     Leu Asp Arg Asp Ser     Leu Tyr Val
    13580                    13585                    13590

Asn Gly     Phe Thr Gln Arg Ser     Ser Val Pro Thr Thr     Ser Ile Pro
    13595                    13600                    13605

Gly Thr     Pro Thr Val Asp Leu     Gly Thr Ser Gly Thr     Pro Val Ser
    13610                    13615                    13620
```

```
Lys Pro Gly Pro Ser Ala Ala     Ser Pro Leu Leu Val     Leu Phe Thr
    13625           13630                   13635

Leu Asn Phe Thr Ile Thr Asn     Leu Arg Tyr Glu Glu     Asn Met Gln
    13640           13645                   13650

His Pro Gly Ser Arg Lys Phe     Asn Thr Thr Glu Arg     Val Leu Gln
    13655           13660                   13665

Gly Leu Leu Arg Ser Leu Phe     Lys Ser Thr Ser Val     Gly Pro Leu
    13670           13675                   13680

Tyr Ser Gly Cys Arg Leu Thr     Leu Leu Arg Pro Glu     Lys Asp Gly
    13685           13690                   13695

Thr Ala Thr Gly Val Asp Ala     Ile Cys Thr His His     Pro Asp Pro
    13700           13705                   13710

Lys Ser Pro Arg Leu Asp Arg     Glu Gln Leu Tyr Trp     Glu Leu Ser
    13715           13720                   13725

Gln Leu Thr His Asn Ile Thr     Glu Leu Gly Pro Tyr     Ala Leu Asp
    13730           13735                   13740

Asn Asp Ser Leu Phe Val Asn     Gly Phe Thr His Arg     Ser Ser Val
    13745           13750                   13755

Ser Thr Thr Ser Thr Pro Gly     Thr Pro Thr Val Tyr     Leu Gly Ala
    13760           13765                   13770

Ser Lys Thr Pro Ala Ser Ile     Phe Gly Pro Ser Ala     Ala Ser His
    13775           13780                   13785

Leu Leu Ile Leu Phe Thr Leu     Asn Phe Thr Ile Thr     Asn Leu Arg
    13790           13795                   13800

Tyr Glu Glu Asn Met Trp Pro     Gly Ser Arg Lys Phe     Asn Thr Thr
    13805           13810                   13815

Glu Arg Val Leu Gln Gly Leu     Leu Arg Pro Leu Phe     Lys Asn Thr
    13820           13825                   13830

Ser Val Gly Pro Leu Tyr Ser     Gly Cys Arg Leu Thr     Leu Leu Arg
    13835           13840                   13845

Pro Glu Lys Asp Gly Glu Ala     Thr Gly Val Asp Ala     Ile Cys Thr
    13850           13855                   13860

His Arg Pro Asp Pro Thr Gly     Pro Gly Leu Asp Arg     Glu Gln Leu
    13865           13870                   13875

Tyr Leu Glu Leu Ser Gln Leu     Thr His Ser Ile Thr     Glu Leu Gly
    13880           13885                   13890

Pro Tyr Thr Leu Asp Arg Asp     Ser Leu Tyr Val Asn     Gly Phe Thr
    13895           13900                   13905

His Arg Ser Ser Val Pro Thr     Thr Ser Thr Gly Val     Val Ser Glu
    13910           13915                   13920

Glu Pro Phe Thr Leu Asn Phe     Thr Ile Asn Asn Leu     Arg Tyr Met
    13925           13930                   13935

Ala Asp Met Gly Gln Pro Gly     Ser Leu Lys Phe Asn     Ile Thr Asp
    13940           13945                   13950

Asn Val Met Gln His Leu Leu     Ser Pro Leu Phe Gln     Arg Ser Ser
    13955           13960                   13965

Leu Gly Ala Arg Tyr Thr Gly     Cys Arg Val Ile Ala     Leu Arg Ser
    13970           13975                   13980

Val Lys Asn Gly Ala Glu Thr     Arg Val Asp Leu Leu     Cys Thr Tyr
    13985           13990                   13995

Leu Gln Pro Leu Ser Gly Pro     Gly Leu Pro Ile Lys     Gln Val Phe
    14000           14005                   14010
```

-continued

| | | | | | | | | | | | |
|---|---|---|---|---|---|---|---|---|---|---|---|
|His|Glu|Leu|Ser|Gln|Gln|Thr|His|Gly|Ile|Thr|Arg|Leu|Gly|Pro|
| |14015| | | | |14020| | | | |14025| | | |

Tyr Ser Leu Asp Lys Asp Ser Leu Tyr Leu Asn Gly Tyr Asn Glu
14030                    14035                    14040

Pro Gly Pro Asp Glu Pro Pro Thr Thr Pro Lys Pro Ala Thr Thr
14045                    14050                    14055

Phe Leu Pro Pro Leu Ser Glu Ala Thr Thr Ala Met Gly Tyr His
14060                    14065                    14070

Leu Lys Thr Leu Thr Leu Asn Phe Thr Ile Ser Asn Leu Gln Tyr
14075                    14080                    14085

Ser Pro Asp Met Gly Lys Gly Ser Ala Thr Phe Asn Ser Thr Glu
14090                    14095                    14100

Gly Val Leu Gln His Leu Leu Arg Pro Leu Phe Gln Lys Ser Ser
14105                    14110                    14115

Met Gly Pro Phe Tyr Leu Gly Cys Gln Leu Ile Ser Leu Arg Pro
14120                    14125                    14130

Glu Lys Asp Gly Ala Ala Thr Gly Val Asp Thr Thr Cys Thr Tyr
14135                    14140                    14145

His Pro Asp Pro Val Gly Pro Gly Leu Asp Ile Gln Gln Leu Tyr
14150                    14155                    14160

Trp Glu Leu Ser Gln Leu Thr His Gly Val Thr Gln Leu Gly Phe
14165                    14170                    14175

Tyr Val Leu Asp Arg Asp Ser Leu Phe Ile Asn Gly Tyr Ala Pro
14180                    14185                    14190

Gln Asn Leu Ser Ile Arg Gly Glu Tyr Gln Ile Asn Phe His Ile
14195                    14200                    14205

Val Asn Trp Asn Leu Ser Asn Pro Asp Pro Thr Ser Ser Glu Tyr
14210                    14215                    14220

Ile Thr Leu Leu Arg Asp Ile Gln Asp Lys Val Thr Thr Leu Tyr
14225                    14230                    14235

Lys Gly Ser Gln Leu His Asp Thr Phe Arg Phe Cys Leu Val Thr
14240                    14245                    14250

Asn Leu Thr Met Asp Ser Val Leu Val Thr Val Lys Ala Leu Phe
14255                    14260                    14265

Ser Ser Asn Leu Asp Pro Ser Leu Val Glu Gln Val Phe Leu Asp
14270                    14275                    14280

Lys Thr Leu Asn Ala Ser Phe His Trp Leu Gly Ser Thr Tyr Gln
14285                    14290                    14295

Leu Val Asp Ile His Val Thr Glu Met Glu Ser Ser Val Tyr Gln
14300                    14305                    14310

Pro Thr Ser Ser Ser Ser Thr Gln His Phe Tyr Leu Asn Phe Thr
14315                    14320                    14325

Ile Thr Asn Leu Pro Tyr Ser Gln Asp Lys Ala Gln Pro Gly Thr
14330                    14335                    14340

Thr Asn Tyr Gln Arg Asn Lys Arg Asn Ile Glu Asp Ala Leu Asn
14345                    14350                    14355

Gln Leu Phe Arg Asn Ser Ser Ile Lys Ser Tyr Phe Ser Asp Cys
14360                    14365                    14370

Gln Val Ser Thr Phe Arg Ser Val Pro Asn Arg His His Thr Gly
14375                    14380                    14385

Val Asp Ser Leu Cys Asn Phe Ser Pro Leu Ala Arg Arg Val Asp
14390                    14395                    14400

Arg Val Ala Ile Tyr Glu Glu Phe Leu Arg Met Thr Arg Asn Gly

| | | | | | | | | | | | |
|---|---|---|---|---|---|---|---|---|---|---|---|
| | 14405 | | | | 14410 | | | | 14415 | | |
| Thr | Gln | Leu | Gln | Asn | Phe | Thr | Leu | Asp | Arg | Ser | Ser | Val | Leu | Val |
| | 14420 | | | | | 14425 | | | | 14430 | |
| Asp | Gly | Tyr | Ser | Pro | Asn | Arg | Asn | Glu | Pro | Leu | Thr | Gly | Asn | Ser |
| | 14435 | | | | | 14440 | | | | 14445 | |
| Asp | Leu | Pro | Phe | Trp | Ala | Val | Ile | Leu | Ile | Gly | Leu | Ala | Gly | Leu |
| | 14450 | | | | | 14455 | | | | 14460 | |
| Leu | Gly | Val | Ile | Thr | Cys | Leu | Ile | Cys | Gly | Val | Leu | Val | Thr | Thr |
| | 14465 | | | | | 14470 | | | | 14475 | |
| Arg | Arg | Arg | Lys | Lys | Glu | Gly | Glu | Tyr | Asn | Val | Gln | Gln | Gln | Cys |
| | 14480 | | | | | 14485 | | | | 14490 | |
| Pro | Gly | Tyr | Tyr | Gln | Ser | His | Leu | Asp | Leu | Glu | Asp | Leu | Gln |
| | 14495 | | | | | 14500 | | | | 14505 | |

MOLECULAR BIOMARKER SET FOR EARLY DETECTION OF OVARIAN CANCER

This application is a continuation of U.S. Non-Provisional patent application Ser. No. 13/415,004, filed Mar. 8, 2012, which claims priority to U.S. Provisional Patent Application Ser. No. 61/450,212, filed Mar. 8, 2011. The entire contents of each of the above-referenced disclosures are specifically incorporated herein by reference without disclaimer.

TECHNICAL FIELD

The present invention generally concerns at least the fields of molecular biology, cell biology, and medicine. In particular aspects, the field concerns detection of cancer, including ovarian cancer.

BACKGROUND OF THE INVENTION

Ovarian cancer is the leading cause of death among gynecological malignancies and represents the fifth leading cause of cancer-related deaths in women. The disease is diagnosed at a stage when cancer has already metastasized beyond the ovary in approximately 70% of patients and only 30% of these patients with this advanced-stage ovarian cancer survive 5 years after initial diagnosis. Early diagnosis greatly enhances the chances of successful cancer treatment. To this date, very few early-detection approaches have shown promise for routine clinical use. However, the most commonly used marker of ovarian cancer is CA125, but it is only expressed in 50-60% of patients during early stages of the disease.

BRIEF SUMMARY OF THE INVENTION

The present invention is directed to methods and compositions that regard a biomarker set for detection of ovarian cancer in both early and late stages. In some embodiments, the present invention concerns identification of the increased risk for an individual to develop ovarian cancer. In embodiments of the invention, the level of TFAP2A, CA125, and E2F5 (or TFAP2A alone or in other combinations) is assayed in an individual for the detection of ovarian cancer or other cancers. The individual may be suspected of having ovarian cancer (as an example), based on, for example, family history, testing, and/or symptoms that persist, for example, for two or more weeks (for example, abdominal swelling/bloating; abdominal/pelvic pain or pressure or feeling "full"; gastrointestinal symptoms (such as gas, indigestion, nausea, or changes in bowel movements); vaginal bleeding or discharge; urinary problems (urgency, burning, or spasms); fatigue and/or fever; pain during intercourse; back pain; and/or difficulty breathing). In some embodiments the individual has no symptoms of cancer, including ovarian cancer, yet the individual is subjected to methods of the invention as a part of routine testing.

Individuals with an increased risk of developing ovarian cancer may be subjected to methods of the present invention. In specific cases, an individual with an increased risk is of a particular age (such as over about 40, over about 45, over about 50, over about 55, over about 60, or over about 65); has reached menopause; is obese; has no biological children; has taken fertility drugs or androgens; has had estrogen therapy; has a family history of ovarian and/or breast cancer; has a personal history of breast cancer; or uses talcum powder on the genitalia, for example. In some embodiments, the individual has no personal or family history of ovarian cancer and is not necessarily considered at risk but undergoes testing at least by methods of the invention as routine testing in preventative health care (similar to periodic Pap smear testing for cervical cancer, for example).

In some embodiments, the levels of TFAP2A and optionally one or both of CA125 and E2F5 are assayed to monitor the effectiveness of an ovarian cancer treatment. Exemplary ovarian cancer treatments include surgery, radiation, and/or primary therapy with drugs that contain platinum and taxane compounds (e.g., cisplatin, carboplatin, paclitaxel); however, other drugs, such as "mustards" (e.g., melphalan) and anthracyclines (e.g., doxorubicin) are also useful for first-line activity in ovarian cancer. Other drugs include altretamine, 5-fluorouracil, topotecan, ifosamide, and/or etoposide, for example. The regimen of ovarian chemotherapies are determined by a variety of factors, including the type and/or stage of ovarian cancer, health status, etc. In some embodiments, the levels of TFAP2A and optionally CA125, and/or E2F5 are utilized for determination of a treatment regimen for ovarian cancer. In some embodiments of the invention, the methods are employed to determine if an individual should be given a particular cancer therapy, for example whether an individual would be resistant to a particular cancer drug.

The present invention allows detection of any type of ovarian cancer, in particular embodiments. Thus, in certain embodiments the present invention may detect ovarian cancers of the three main types of ovarian tumors, including epithelial ovarian tumors (the most common), which are derived from the cells on the surface of the ovary; germ cell ovarian tumors, which are derived from the egg-producing cells within the ovarian body; and sex cord stromal ovarian tumors, which are a type that often produces steroid hormones. Epithelial tumors are further subdivided into (a) benign, (b) borderline (low-malignant potential [LMP] or atypical proliferative), and (c) invasive carcinoma, and the present invention determines any of these types, in specific embodiments. The present invention may be utilized to detect any stage of ovarian cancer, including those identified in the American Joint Committee on Cancer (AJCC) TNM (Tumor size, Lymph Nodes affected, Metastases) system for ovarian cancer: Stage IA, IB, IC, IIA, IIB, IIC, IIIA, IIIB, IIIC, or IV, although in specific embodiments the detection occurs for early stage ovarian cancer, such as Stage IA, IB, or IC.

Levels of TFAP2A and optionally CA125 and/or E2F5 may be determined by any suitable means, but in specific embodiments the levels are determined for protein or mRNA, or both. The levels may be determined from a sample from the individual, including from a fluid or tissue, for example. In specific embodiments, the sample is blood or ovarian tissue, such as from a biopsy. The blood may be further fractionated before analysis, in specific embodiments. Samples used in the invention may be subjected to methods of the invention directly from the individual, or the samples may be stored in a suitable storage means, such as under refrigeration, and the sample may be transported from the individual to a separate facility for analysis, for example. The person that extracts the sample may or may not be the person that performs the method(s) of the invention, and the facility in which the person that extracts the sample is located may not be the facility in which the method(s) of the invention is performed.

In some methods of the invention, the method further comprises the step(s) of obtaining a sample from the individual, isolating nucleic acid (including mRNA) and/or protein from the sample; and analyzing the levels of TFAP2A and optionally CA125 and/or E2F5 in the sample.

The same sample may be used for processing of each of TFAP2A and optionally CA125 and/or E2F5, although in other embodiments different samples from the same area or type from the same individual are used to analyze TFAP2A, CA125, and/or E2F5, respectively. The analysis of each of TFAP2A, CA125, and/or E2F5 may be performed substantially concomitantly or may be performed successively. In some embodiments, a sample is analyzed for one or more of TFAP2A and optionally CA125 and/or E2F5, and upon determination of a particular outcome of such analysis, the one or more of TFAP2A, CA125, and/or E2F5, respectively, that were not originally analyzed are thereafter analyzed.

In one embodiment of the invention, there is a method of evaluating the probability of the presence of ovarian cancer in a subject, the method comprising measuring the amounts of TFAP2A and optionally CA125 and E2F5 in a biological sample from the subject; comparing the measured amounts of TFAP2A and optionally CA125 and E2F5 in the biological sample to a standard for TFAP2A and optionally CA125 and E2F5, respectively, wherein the standard is a level of TFAP2A, CA125, and E2F5, respectively, obtained from a sample of a member of the group consisting of a healthy subject or a subject with normal or benign ovarian tissue, and identifying an increase in the amount of the respective TFAP2A, CA125, and E2F5 in the biological sample as compared to the standard, wherein the increase is indicative of the presence of or the probability of the presence of malignant or pre-malignant cells of ovarian cancer.

In one embodiment of the invention, there is a method of identifying ovarian cancer in an individual or the risk of developing ovarian cancer in an individual, comprising the step of comparing the level of TFAP2A and optionally CA125 and/or E2F5 from the individual with the expression level of the respective TFAP2A, CA125, and E2F5 from a control. In a specific embodiment of the invention, when the levels of the respective TFAP2A, CA125, and E2F5 are higher in the individual compared to the control, the individual has ovarian cancer or has a risk of developing ovarian cancer. In particular aspects of the invention, the protein level of TFAP2A and optionally CA125 and/or E2F5 from the individual is determined, such as determined from the blood of the individual. The protein level of TFAP2A, CA125, and/or E2F5 may be determined with an antibody, such as a monoclonal antibody, for example.

In some aspects of the invention, the mRNA level of TFAP2A and optionally CA125 and E2F5 from the individual is determined, such as determined from ovarian tissue from the individual. The mRNA level may be determined by microarray, Northern, or RT-PCR, for example.

In specific embodiments of the invention, the control is from blood or tissue from one or more normal individuals. In particular aspects, the method detects the stage of ovarian cancer in the individual. In certain embodiments, the stage is stage IA, IC, IIIC, or a combination thereof. In some embodiments, the control is from normal tissue from the individual being screened.

In some embodiments of the invention, the method further comprises the step of performing an additional ovarian cancer detection method, such as one selected from the group consisting of palpitation, ultrasound, magnetic resonance imaging, X-ray, CT scan, blood testing, and biopsy, for example.

In some embodiments, the method further comprises the step of administering treatment for ovarian cancer. Exemplary treatments for ovarian cancer include surgery, radiation, and/or primary therapy with drugs that contain platinum and taxane compounds (e.g., cisplatin, carboplatin, paclitaxel); "mustards" (e.g., melphalan), anthracyclines (e.g., doxorubicin), altretamine, 5-fluorouracil, topotecan, ifosamide, and etoposide.

In specific aspects, the method further comprises the step of obtaining a sample from the individual. The sample may be obtained by routine methods in the art.

In some cases, the method further comprises the step of isolating TFAP2A, CA125, and E2F5 protein and/or mRNA from the sample. In specific aspects, the method further comprises the steps of obtaining a sample from the individual and isolating TFAP2A, CA125, and E2F5 protein and/or mRNA from the sample.

In one embodiment of the invention, there is a kit comprising one or more detection reagents for TFAP2A, CA125, and E2F5, said reagents housed in a suitable container, and in some cases the reagent is selected from the group consisting of antibody, microarray, oligonucleotide, polymerase, deoxyribonucleotides, buffer, or a combination thereof. In specific aspects, the method further comprises an apparatus for obtaining a sample from an individual, such as drawing blood or taking a biopsy from an individual.

In one embodiment, there is a method of identifying ovarian cancer in an individual or the risk of developing ovarian cancer in an individual, comprising the step of comparing the level of TFAP2A from the individual with the expression level of TFAP2A from a control. In a specific embodiment, the method further comprises the step of comparing the level of CA125 or E2F5 or both from the individual with the expression level of CA125 or E2F5 or both, respectively, from a control.

In a particular embodiment, there is a method of identifying ovarian cancer in an individual or the risk of developing ovarian cancer in an individual, comprising the step of comparing the level of TFAP2A and one or both of CA125 or E2F5 from the individual with the expression level of TFAP2A and one or both of CA125 or E2F5, respectively, from a control.

In some embodiments, there are methods of identifying ovarian cancer in an individual or the risk of developing ovarian cancer in an individual, comprising the steps of a) obtaining a sample from the individual, b) determining the expression level of TFAP2A from the sample, and c) comparing the expression level of TFAP2A from the individual with the expression level of TFAP2A from a control, wherein when the level of TFAP2A is higher in the individual compared to the control, the individual has ovarian cancer or has a risk of developing ovarian cancer.

In some embodiments, there are methods of identifying ovarian cancer in an individual or the risk of developing ovarian cancer in an individual, comprising the steps of a) obtaining a sample from the individual, b) determining the expression level of TFAP2A from the sample, c) determining the expression level of CA125 and/or E2F5 from the sample, d) comparing the expression level of TFAP2A from the individual with the expression level of TFAP2A from a control, and e) comparing the expression level of CA125 and/or E2F5 from the individual with the expression level of CA125 and/or E2F5 from a control, wherein when the level of TFAP2A and CA125 or E2F5 is higher in the individual compared to the control, the individual has ovarian cancer or has a risk of developing ovarian cancer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

DETAILED DESCRIPTION OF THE INVENTION

Figure 1:
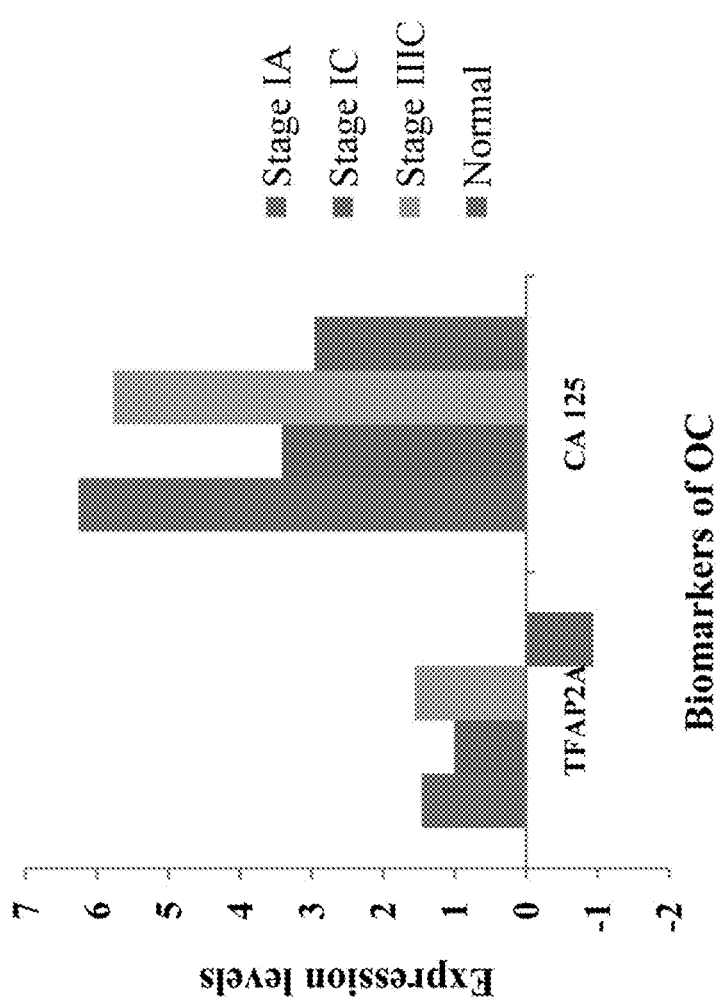
FIG. 1 shows the comparison of the expression levels of TFAP2A and CA125 in randomly chosen ovarian serous adenocarcinoma tissue samples categorized at stages IA, IC, and IIIC in comparison to normal tissue based on an ovarian cancer study by Lu et al. (2004).

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "biomarker" refers to a marker (expressed gene, including mRNA and/or protein) that allows detection of disease in an individual when compared to a healthy individual, including detection of disease in its early stages. In specific embodiments, the expression level of the biomarker as determined by mRNA and/or protein levels in tissue or biological material from an individual to be tested is compared with respective levels in normal ovarian tissue or biological material from the same individual or another healthy individual.

As used herein, the term "control" refers to any entity used in comparison of the biomarkers expression. For example, in the cases when disease biomarkers are in question, a control could be the expression pattern of the biomarkers in an individual not affected by the disease; it could be the averaged expression pattern of the biomarkers from a group of individuals not affected by the disease; it could be the expression of another gene/protein in the same individual; for one biomarker it could be the expression of another biomarker in the same individual; it could be a threshold on the score produced by a mathematical model that uses the expressions of biomarkers and possibly expression of other genes/proteins so that scores for disease-affected individuals and for individuals not affected by the disease significantly differ (this for example includes all model-based classifiers of disease-affected and disease-nonaffected cases). The expression and the expression pattern could be either absolute or relative, i.e. determined relative to the expression of some other gene(s)/protein(s). In specific embodiments, the control is derived at least in part from the level of expression of a reference gene/protein from a single individual without ovarian cancer. One of skill in the art recognizes that the control expression level may be normalized by standard means in the art. The normalization may include standardization to a reference protein (such as a housekeeping gene including GAPDH and RN18S1), for example (see also Tunbridge et al., 2011; Bär et al., 2009). In certain embodiments, the identification of ovarian cancer (or another respective type of cancer) is achieved when the level of expression of a biomarker is above a normalized threshold compared to a control. In some cases, the identification of ovarian cancer (or another respective type of cancer) is achieved when the level of expression of a biomarker is below a normalized threshold compared to a control.

In specific embodiments of the invention, the control is from blood or tissue from one or more normal individuals or is from blood or tissue from the individual being screened. In specific aspects, the control is derived at least in part from the average level of expression of a reference gene/protein in a collection of individuals that do not have ovarian cancer, although the individuals in the collection may or may not have another type of cancer.

I. General Embodiments of the Invention

The present invention concerns detection of ovarian cancer in an individual or identifying an individual with an increased risk of developing ovarian cancer. In some embodiments, the invention offers diagnostic benefits for patients with ovarian cancer, for example by helping medical care providers diagnose ovarian cancer in very early stages that can substantially improve the survival rate in these patients. The invention is useful for the health care industry in embodiments where diagnostic kits are routinely used, in specific cases.

Using computational analysis, the inventors have identified TFAP2A, which controls the expression of several ovarian cancer genes in the cell, as a new biomarker for early diagnosis of ovarian cancer. The computation analysis described in this disclosure shows that TFAP2A is useful as a biomarker for detection of early stages of ovarian cancer, because the data indicate that it is expressed in patients with early stages of ovarian cancer, but no expression is seen in normal individuals. For the same set of patients, the analysis shows that CA125, a known biomarker of ovarian cancer, has detectable expression level in both normal as well as ovarian cancer individuals. Therefore, CA125 does not have the power to differentiate the cancer from normal states in many cases, whereas the TFAP2A has clearly detectable higher expression levels in ovarian cancer patients as compared to normal. A combination of biomarkers TFAP2A, E2F5 and CA125 is a more accurate means for diagnosing ovarian cancer.

In certain embodiments of the invention, the technology is based on a unique combination of three biomarkers for use as a diagnostic tool for ovarian cancer. All three biomarkers were evaluated individually as well as in certain combinations for use in diagnosis of cancer. In certain embodiments, the invention concerns identification of a new set of a combination of biomarkers for use in simultaneous diagnosis and early detection of ovarian cancer. The biomarker set consists of three gene products: TFAP2A, E2F5, and CA125. In specific aspects, the presence of these biomarkers in blood, for example, is an indicator of ovarian cancer, although other fluids or tissues may be assayed. Different combinations of these biomarkers result in different sensitivity and specificity of ovarian cancer detection. That is, the CA125 is in use as a standard biomarker for detection of ovarian cancer, but it does not have good accuracy of ovarian cancer detection (Sasaroli et al., 2009). Another biomarker, E2F5, has been recently discovered (Kothandaraman et al., 2010) where it has been shown that in combination with CA125 there was significant improvement of the accuracy of ovarian cancer detection and ability to detect ovarian cancer in early stages. The third biomarker for use in combination with CA125 and E2F5 is TFAP2A that shows expression in early ovarian cancer stages but not in normal individuals.

In some embodiments of the invention, there is a single biomarker used as a diagnostic tool for cancer, including ovarian cancer. In specific aspects, the presence of this biomarker in blood, for example, is an indicator of ovarian cancer, although other fluids or tissues may be assayed.

Thus, in embodiments of the invention, presence of TFAP2A, E2F5, and CA125 in different combinations in human blood samples improves the accuracy of diagnosis of ovarian cancer in clinical settings and enhances the capability to detect ovarian cancer, for example in early stages.

In some embodiments, the mere presence or absence of a marker, without quantifying the amount of marker, is useful and can be correlated with a diagnosis of ovarian cancer or increased risk of developing ovarian cancer. For example, TFAP2A, E2F5, and CA125 can be more frequently detected in human ovarian cancer patients than in normal subjects. Thus, a detected presence of these markers in a subject being tested indicates that the subject has ovarian cancer or has a higher probability of having ovarian cancer.

In other embodiments, the measurement of markers can involve quantifying the markers to correlate the detection of markers with a probable diagnosis of ovarian cancer. Thus, if the amount of the markers detected in a subject being tested is different compared to a control amount (i.e., higher or lower than the control, depending on the marker), then the subject being tested has a higher probability of having ovarian cancer.

The correlation may take into account the amount of the marker or markers in the sample compared to a control amount of the marker or markers (up or down regulation of the marker or markers) (e.g., in normal subjects in whom human cancer is undetectable). A control can be, e.g., the average or median amount of marker present in comparable samples of normal subjects in whom human cancer is undetectable. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determination of ovarian cancer status.

In certain embodiments of the methods of qualifying ovarian cancer status, the methods further comprise managing subject treatment based on the status. As aforesaid, such management describes the actions of the physician or clinician subsequent to determining ovarian cancer status. For example, if the result of the methods of the present invention is inconclusive or there is reason that confirmation of status is necessary, the physician may order more tests. Alternatively, if the status indicates that surgery is appropriate, the physician may schedule the patient for surgery. In other instances, the patient may receive chemotherapy or radiation treatments, either in lieu of, or in addition to, surgery. Likewise, if the result is negative, no further action may be warranted. Furthermore, if the results show that treatment has been successful, no further management may be necessary.

The invention also provides for such methods where the biomarkers (or specific combination of biomarkers) are measured again after subject management. In these cases, the methods are used to monitor the status of the cancer, e.g., response to cancer treatment, remission of the disease or progression of the disease. Because of the ease of use of the methods and the lack of invasiveness at least in certain embodiments of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

The methods of the present invention have other applications as well. For example, the markers can be used to screen for compounds that modulate the expression of the markers in vitro or in vivo, which compounds in turn may be useful in treating or preventing ovarian cancer in patients. In another example, the markers can be used to monitor the response to treatments for ovarian cancer. In yet another example, the markers can be used in heredity studies to determine if the subject is at risk for developing ovarian cancer. For instance, certain markers may be genetically linked. This can be determined by, e.g., analyzing samples from a population of ovarian cancer patients whose families have a history of ovarian cancer. The results can then be compared with data obtained from, e.g., ovarian cancer patients whose families do not have a history of ovarian cancer. The markers that are genetically linked may be used as a tool to determine if a subject whose family has a history of ovarian cancer is pre-disposed to having ovarian cancer.

II. Gene Products Used in Embodiments of the Invention

The present invention employs methods and reagents related to assaying for expression levels of one or more particular genes, including TFAP2A and, in embodiments of the invention, also of CA125 and E2F5. The expression level may be determined by measuring levels of mRNA and/or protein, in specific embodiments.

TFAP2A is also referred to as transcription factor AP-2 alpha (activating enhancer binding protein 2 alpha); RP1-290I10.1; AP-2; AP-2alpha; AP2TF; BOFS; FLJ51761; TFAP2; AP-2 transcription factor; AP2-alpha; OTTHUMP00000214240; OTTHUMP00000214243; activating enhancer-binding protein 2-alpha; and activator protein 2; for example. Exemplary GenBank® TFAP2A mRNA sequences are provided in NM_001032280.2; NM_001042425.1; and NM_003220.2 (SEQ ID NO:1) (the three of which correspond to isoforms b, c, and a, respectively), all of which sequences are incorporated by reference herein. Exemplary GenBank® TFAP2A protein sequences are provided in NP_001027451.1; NP_001035890.1; and NP_003211.1 (SEQ ID NO:2) (the three of which correspond to isoforms b, c, and a, respectively), all of which sequences are incorporated by reference herein.

E2F5 is also referred to as E2F transcription factor 5, E2F-5, and p130-binding. Exemplary GenBank® E2F5 mRNA sequences are provided in NM_001083588.1; NM_001083589.1; and NM_001951.3 (SEQ ID NO:3) (the three of which correspond to isoforms 2, 3, and 1, respectively), all of which sequences are incorporated by reference herein. Exemplary GenBank®E2F5 protein sequences are provided in NP_001077057.1; NP_001077058.1; and NP_001942.2 (SEQ ID NO:4) (the three of which correspond to isoforms 2, 3, and 1, respectively), all of which sequences are incorporated by reference herein.

CA125 is also referred to as cancer antigen 125; carbohydrate antigen 125; MUC16; mucin 16, cell surface associated; FLJ14303; CA-125; CA125 ovarian cancer antigen; MUC-16; mucin-16; ovarian cancer-related tumor marker CA125; and ovarian carcinoma antigen CA125. Exemplary GenBank® CA125 mRNA sequence is provided in NM_024690.2 (SEQ ID NO:5), which is incorporated by reference herein. Exemplary GenBank® CA125 protein sequence is provided in NP_078966.2 (SEQ ID NO:6), which is incorporated by reference herein.

Other Markers

In some embodiments of the invention, additional markers to TFAP2A, E2F5, and CA125 are utilized in the invention. In exemplary embodiments, ovarian cancer markers described in U.S. Pat. No. 7,605,003, which is incorporated herein by reference, are employed in the invention. Exemplary markers include CA15-3, CA19-9, CA72-4, CA 195, TATI, CEA, PLAP, Sialyl TN, galactosyltransferase, M-CSF, CSF-1, LPA, p110EGFR, tissue kallikreins, prostasin, HE4, CKB, LASA, HER-2/neu, urinary gonadotropin peptide, Dianon NB 70/K, TPA, osteopontin and haptoglobin, and protein variants (e.g., cleavage forms, isoforms) of the markers; in specific embodiments, the levels of these markers are different in individuals with cancer compared to normal individuals. For example, CA 19-9, CA 72.4, CA 195, TATI, inhibin and PLAP, and others, are known to be elevated in the blood of women with ovarian cancer.

Other markers that may be used in the methods of the invention include those described in U.S. Pat. No. 7,745,149, which is incorporated by reference herein, and encompasses galectin-1, cathepsin B, MHC class I antigen, heat shock protein (HSP) 27, ubiquitin carboxy-termal esterase L1, plasma retinol-binding protein (PRBP), transthyretin, SH3 binding glutamate-rich protein, tubulin-specific chaperone A, RNA binding protein regulatory subunit, γ-actin, tropomyosin and calcium/calmodulin-stimulated cyclic nucleotide phosphatase.

Additional markers that may be used in the methods of the invention include hK10 and/or hK6, described in U.S. Pat. No. 7,741,019, which is incorporated by reference herein.

III. Test Samples

A. Subject Types

Samples are collected from subjects, e.g., women, who want to establish ovarian cancer status. The subjects may be women who have been determined to have a high risk of ovarian cancer, for example based on their family history. Other patients include women who have ovarian cancer and the test is being used to determine the effectiveness of therapy or treatment they are receiving. Also, patients could include healthy women who are having a test as part of a routine examination, or to establish baseline levels of the biomarkers. Samples may be collected from women who had been diagnosed with ovarian cancer and received treatment to eliminate the cancer, or perhaps are in remission.

B. Types of Sample and Preparation of the Sample

The markers can be measured in different types of biological samples. The sample is preferably a biological fluid sample. Examples of a biological fluid sample useful in this invention include blood, blood serum, plasma, vaginal secretions, urine, tears, saliva, etc. Blood is a preferred sample source for certain embodiments of the invention because of its non-invasiveness. In alternative embodiments, the sample is from biopsy.

If desired, the sample can be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used, in some embodiments. For example, sample preparation may be unnecessary if antibodies that specifically bind markers are used to detect the presence of markers in a sample.

Typically, sample preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in PCT/US03/00531 (incorporated herein in its entirety).

In some cases, the sample is pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomolecules in a sample that are more negatively charged from other types of biomolecules. Proteins that are eluted with an eluant having a high pH is likely to be weakly negatively charged, and a fraction that is eluted with an eluant having a low pH is likely to be strongly negatively charged. Thus, in addition to reducing complexity of a sample, anion exchange chromatography separates proteins according to their binding characteristics.

In certain embodiments, the serum samples are fractionated via anion exchange chromatography. Signal suppression of lower abundance proteins by high abundance proteins presents a significant challenge to SELDI mass spectrometry. Fractionation of a sample reduces the complexity of the constituents of each fraction. This method can also be used to attempt to isolate high abundance proteins into a fraction, and thereby reduce its signal suppression effect on lower abundance proteins. Anion exchange fractionation separates proteins by their isoelectric point (pI). Proteins are comprised of amino acids, which are ambivalent-their charge changes based on the pH of the environment to which they are exposed. A protein's pI is the pH at which the protein has no net charge. A protein assumes a neutral charge when the pH of the environment is equivalent to pI of the protein. When the pH rises above the pI of the protein, the protein assumes a net negative charge. Similarly, when the pH of the environment falls below the pH of the protein, the protein has a net positive charge. The serum samples were fractionated according to the protocol set forth in the Examples below to obtain the markers described herein.

After capture on anion exchange, proteins were eluted in a series of step washes at pH 9, pH 7, pH 5, pH 4 and pH 3. A panel of three potential biomarkers was discovered by UMSA analysis of profiling data of three fractions (pH 9/flow through, pH 4, and organic solvent). Two of the peaks were from fraction pH 4 at m/z of 12828 and 28043, both down-regulated in the cancer group, and the third was from fraction pH 9/flow through at m/z of 3272, up-regulated in the cancer group. All bound to the immobilized metal affinity chromatography array charged with copper ions (IMAC3-Cu) (spectra in FIG. 1).

Biomolecules in a sample can also be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomolecules, including one or more markers. See, e.g., Jungblut and Thiede, Mass Specir. Rev. 16:145-162 (1997).

The two-dimensional gel electrophoresis can be performed using methods known in the art. See, e.g., Deutscher ed., Methods In Enzymology vol. 182. Typically, biomolecules in a sample are separated by, e.g., isoelectric focusing, during which biomolecules in a sample are separated in a pH gradient until they reach a spot where their net charge is zero (i.e., isoelectric point). This first separation step results in one-dimensional array of biomolecules. The biomolecules in one-dimensional array is further separated using a technique generally distinct from that used in the first separation step. For example, in the second dimension, biomolecules separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomolecules. Typically, two-dimensional gel electrophoresis can separate chemically different biomolecules in the molecular mass range from 1000-200,000 Da within complex mixtures. The pI range of these gels is about 3-10 (wide range gels).

Biomolecules in the two-dimensional array can be detected using any suitable methods known in the art. For example, biomolecules in a gel can be labeled or stained (e.g., Coomassie Blue or silver staining). If gel electrophoresis generates spots that correspond to the molecular weight of one or more markers of the invention, the spot can be further analyzed by gas phase ion spectrometry. For example, spots can be excised from the gel and analyzed by gas phase ion spectrometry. Alternatively, the gel containing biomolecules can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip® array) as described herein.

Prior to gas phase ion spectrometry analysis, it may be desirable to cleave biomolecules in the spot into smaller fragments using cleaving reagents, such as proteases (e.g., trypsin). The digestion of biomolecules into small fragments provides a mass fingerprint of the biomolecules in the spot, which can be used to determine the identity of markers if desired.

High performance liquid chromatography (HPLC) can also be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers. For example, the spots can be analyzed using either MALDI or SELDI (e.g., using ProteinChip® array) as described herein.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomolecules can be modified to improve detection resolution. For instance, neuraminidase can be used to remove terminal sialic acid residues from glycoproteins to improve binding to an anionic adsorbent (e.g., cationic exchange ProteinChip® arrays) and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt).

C. Capture of Markers

Biomarkers may be captured with capture reagents immobilized to a solid support, such as any biochip described herein, a multiwell microtiter plate or a resin. In particular, the biomarkers of this invention are preferably captured on SELDI protein biochips. Capture can be on a chromatographic surface or a biospecific surface. Any of the SELDI protein biochips comprising reactive surfaces can be used to capture and detect the biomarkers of this invention. However, the biomarkers of this invention bind well to immobilized metal chelates. The IMAC-3 and IMAC 30 biochips, which nitriloacetic acid functionalities that adsorb transition metal ions, such as $Cu^{++}$ and $Ni^{++}$, by chelation, are the preferred SELDI biochips for capturing the biomarkers of this invention. Any of the SELDI protein biochips comprising reactive surfaces can be used to capture and detect the biomarkers of this invention. These biochips can be derivatized with the antibodies that specifically capture the biomarkers, or they can be derivatized with capture reagents, such as protein A or protein G that bind immunoglobulins. Then the biomarkers can be captured in solution using specific antibodies and the captured markers isolated on chip through the capture reagent.

In general, a sample containing the biomarkers, such as blood or serum, is placed on the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash. The retained protein biomarkers now can be detected by appropriate means.

D. Detection and Measurement of Markers

Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy and radio frequency methods. Using these methods, one or more markers can be detected.

1. SELDI

One preferred method of detection and/or measurement of the biomarkers uses mass spectrometry and, in particular, "Surface-enhanced laser desorption/ionization" or "SELDI". SELDI refers to a method of desorption/ionization gas phase ion spectrometry (e.g., mass spectrometry) in which the analyte is captured on the surface of a SELDI probe that engages the probe interface. In "SELDI MS," the gas phase ion spectrometer is a mass spectrometer. SELDI technology is described in more detail above. ApoA1, transthyretin .DELTA.N10 and IAIH4 fragment are detected as peaks at m/z of 28043, m/z of about 12870.9, and m/z of 3272, respectively.

2. Immunoassay

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). The immunoassay is characterized by the use of specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

Using the purified markers or their nucleic acid sequences, antibodies that specifically bind to a marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)). Typically a specific or selective reaction will be at least twice background signal or noise and more typically more than 10 to 100 times background.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array described above. The sample is preferably a biological fluid sample taken from a subject. Examples of biological fluid samples include blood, serum, plasma, nipple aspirate, urine, tears, saliva etc. In a preferred embodiment, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid human cancer diagnosis or prognosis. In another example, the methods for detection of the markers can be used to monitor responses in a subject to cancer treatment. In another example, the methods for detecting markers can be used to assay for and to identify compounds that modulate expression of these markers in vivo or in vitro. In a preferred example, the biomarkers are used to differentiate between the different stages of tumor progression, thus aiding in determining appropriate treatment and extent of metastasis of the tumor.

IV. Combination Methods for Detection of Ovarian Cancer

In embodiments of the invention, the results of the inventive detection methods are employed with other detection methods or information to provide a diagnosis for an individual. Exemplary ovarian cancer detection methods include analysis of blood, urine or a biopsy of a suspicious area. Examples of blood and urine tests used in combination with methods of the invention include, for example, complete blood count (CBC); urine cytology; blood protein testing (for example, to detect certain abnormal immune system proteins (immunoglobulins); and tumor marker tests. In some embodiments of the invention, an individual with a pelvic mass is subjected to one or more methods of the invention.

Although in some embodiments of the invention the gene product levels are used to monitor patients with a known cancer, for example to determine the stage of cancer or to monitor effectiveness of a cancer therapy, in other embodiments the methods are employed as one of several tests in the workup of an individual suspected of having a tumor.

Thus, in individuals who are known to have a malignancy, such as ovarian cancer, the TFAP2A, E2F5, and CA 125 levels can be monitored periodically, for example. A changed level generally may indicate that therapy, including chemotherapy, has been effective, a level changed in the opposite direction may indicate tumor recurrence, while a stagnant level may indicate lack of effectiveness.

V. Nucleic Acid Detection

In some embodiments of the invention, the expression of TFAP2A, E2F5, and CA125 nucleic acid sequences disclosed herein is determined for ovarian cancer detection or propensity for developing ovarian cancer.

A. Hybridization

In some embodiments, hybridization of respective probes to TFAP2A, E2F5, and CA125 mRNAs are employed in the invention. The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR®, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to TFAP2A, E2F5, and CA125 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification for TFAP2A, E2F5, or CA125, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

VI. Methods of Measuring Protein Expression

In certain embodiments, immunodetection methods are used to measure expression levels, such as increased expression levels of TFAP2A, E2F5, and CA125. Examples of particular immunodetection methods include enzyme linked immunosorbent assay (ELISA), radioimmunoassay (RIA), immunoradiometric assay, immunohistochemistry, fluoroimmunoassay, chemiluminescent assay, bioluminescent assay, Western blot, and so forth. The steps of various useful immunodetection methods have been described in the scientific literature, such as, e.g., Doolittle and Ben-Zeev, 1999; Gulbis and Galand, 1993; De Jager et al., 1993; Nakamura et al., 1987, each incorporated herein by reference.

In general, the immunobinding methods involve measurement of the formation of immunocomplexes. Other methods include methods for isolating and purifying the TFAP2A, E2F5, and CA125 protein from a cell, tissue or organism's samples (such as blood, for example). In these instances, the antibody removes the antigenic TFAP2A, E2F5, and CA125 protein or message from a sample. The antibody will preferably be linked to a solid support, such as in the form of a column matrix, and the sample suspected of containing the message, protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the TFAP2A, E2F5, and CA125 protein, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any TFAP2A, E2F5, and CA125 antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

Any TFAP2A, E2F5, and CA125 antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. Western Blot Analysis

Western blot analysis is an established technique that is commonly employed for analyzing and identifying proteins. The proteins are first separated by electrophoresis in polyacrylamide gel, then transferred ("blotted") onto a nitrocellulose membrane or treated paper, where they bind in the same pattern as they formed in the gel. The antigen is overlaid first with antibody, then with anti-immunoglobulin or protein A labeled with a radioisotope, fluorescent dye, or enzyme. One of ordinary skill in the art would be familiar with this commonly used technique for quantifying protein in a sample.

B. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used. One of ordinary skill in the art would be familiar with use of ELISAs and other immunohistochemical assays.

C. Immunohistochemistry

The antibodies of the present invention may also be used in conjunction with both fresh-frozen and/or formalin-fixed, paraffin-embedded tissue blocks, such as blocks prepared from a tumor biopsy, prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

D. Protein Array Technology

Protein array technology allows high-throughput screening for gene expression and molecular interactions. Protein arrays appear as new and versatile tools in functional genomics, enabling the translation of gene expression patterns of normal and diseased tissues into protein product catalog. Protein function, such as enzyme activity, antibody specificity, and other ligand-receptor interactions and binding of nucleic acids or small molecules can be analyzed on a whole-genome level.

1. Protein Biochip Assays

These arrays, which contain thousands of different proteins or antibodies spotted onto glass slides or immobilized in tiny wells, allow one to examine the biochemical activities and binding profiles of a large number of proteins at once. To examine protein interactions with such an array, a labeled protein is incubated with each of the target proteins immobilized on the slide, and then one determines which of the many proteins the labeled molecule binds.

The basic construction of protein chips has some similarities to DNA chips, such as the use of a glass or plastic surface dotted with an array of molecules. These molecules can be DNA or antibodies that are designed to capture proteins. Defined quantities of proteins are immobilized on each spot, while retaining some activity of the protein. With fluorescent markers or other methods of detection revealing the spots that have captured these proteins, protein microarrays are being used as powerful tools in high-throughput proteomics and drug discovery.

Glass slides are still widely used, since they are inexpensive and compatible with standard microarrayer and detection equipment. However, their limitations include multiple-based reactions, high evaporation rates, and possible cross-contamination.

Matrix slides offer a number of advantages, such as reduced evaporation and no possibility of cross-contamination, but they are expensive. Nanochips for proteomics have the same advantages, in addition to reduced cost and the capability of multiple-component reactions.

The earliest and best-known protein chip is the ProteinChip by Ciphergen Biosystems Inc. (Fremont, Calif.). The ProteinChip is based on the surface-enhanced laser desorption and ionization (SELDI) process. Known proteins are analyzed using functional assays that are on the chip. For example, chip surfaces can contain enzymes, receptor proteins, or antibodies that enable researchers to conduct protein-protein interaction studies, ligand binding studies, or immunoassays. With state-of-the-art ion optic and laser optic technologies, the ProteinChip system detects proteins ranging from small peptides of less than 1000 Da up to proteins of 300 kDa and calculates the mass based on time-of-flight (TOF).

The ProteinChip biomarker system is the first protein biochip-based system that enables biomarker pattern recognition analysis to be done. This system allows researchers to address important clinical questions by investigating the proteome from a range of crude clinical samples (i.e., laser capture microdissected cells, biopsies, tissue, urine, and serum). The system also utilizes biomarker pattern software that automates pattern recognition-based statistical analysis methods to correlate protein expression patterns from clinical samples with disease phenotypes.

Some systems can perform biomarker discovery in days and validation of large sample sets within weeks. Its robotics system accessory automates sample processing, allowing hundreds of samples to be run per week and enabling a sufficient number of samples to be run, which provides high statistical confidence in comprehensive studies for marker discovery and validation.

2. Microfluidic Chip-Based Immunoassays

Microfluidics is one of the most important innovations in biochip technology. Since microfluidic chips can be combined with mass spectrometric analysis, a microfluidic device has been devised in which an electrospray interface to a mass spectrometer is integrated with a capillary electrophoresis channel, an injector, and a protein digestion bed on a monolithic substrate (Wang et al., 2000). This chip thus provides a convenient platform for automated sample processing in proteomics applications.

These chips can also analyze expression levels of serum proteins with detection limits comparable to commercial enzyme-linked immunosorbent assays, with the advantage that the required volume sample is markedly lower compared with conventional technologies.

Biosite (San Diego) manufactures the Triage protein chip that simultaneously measures 100 different proteins by immunoassays. The Triage protein chip immunoassays are performed in a microfluidic plastic chip, and the results are achieved in 15 minutes with picomolar sensitivities. Microfluidic fluid flow is controlled in the protein chip by the surface architecture and surface hydrophobicity in the microcapillaries. The immunoassays utilize high-affinity antibodies and a near-infrared fluorescent label, which is read by a fluorometer.

3. Tissue Microarray Technology

Tissue microarray technology provides a high-throughput approach for linking genes and gene products with normal and disease tissues at the cellular level in a parallel fashion. Compared with classical in situ technologies in molecular pathology that are very time-consuming, tissue microarrays provide increased throughput in two ways: up to 1000 tissue specimens can be analyzed in a single experiment, either at the DNA, RNA, or protein level; and tens of thousands of replicate tissue microarrays can be generated from a set of tissues. This process provides a template for analyzing many more biomarkers than has ever been possible previously in a clinical setting, even using archival, formalin-fixed specimens.

4. Nanoscale Protein Analysis

Most current protocols including protein purification and automated identification schemes yield low recoveries that limit the overall process in terms of sensitivity and speed. Such low protein yields and proteins that can only be isolated from limited source material (e.g., biopsies) can be subjected to nanoscale protein analysis: a nanocapture of specific proteins and complexes, and optimization of all subsequent sample-handling steps, leading to a mass analysis of peptide fragments. This focused approach, also termed targeted proteomics, involves examining subsets of the proteome (e.g., those proteins that are specifically modified, bind to a particular DNA sequence, or exist as members of higher-order complexes or any combination thereof). This approach is used to identify genetic determinants of cancer that alter cellular physiology and respond to agonists.

A new detection technique called multiphoton detection, by Biotrace Inc. (Cincinnati), can quantify subzeptomole amounts of proteins and will be used for diagnostic proteomics, particularly for cytokines and other low-abundance proteins. Biotrace is also developing supersensitive protein biochips to detect concentrations of proteins as low as 5 fg/ml (0.2 attomole/ml), thereby permitting sensitivity that is 1000 times greater than current protein biochips.

VII. Kits of the Invention

All of the essential materials and/or reagents required for detecting TFA2P2A, E2F5, and/or CA125 in a sample may be assembled together in a kit. In particular embodiments, the kit comprises respective antibodies to TFA2P2A, E2F5, and/or CA125. This may comprise a probe or primers designed to hybridize specifically to individual nucleic acids of interest in the practice of the present invention, including TFA2P2A, E2F5, and/or CA125, in some cases. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

Any of the compositions described herein may be comprised in a kit. In a non-limiting example, a composition of the invention may be comprised in a kit. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow molded plastic containers into which the desired vials are retained, for example.

When the components of the kit are provided in one and/or more liquid solutions, the liquid solution is an aqueous solution, with a sterile aqueous solution being particularly preferred. In specific cases, the container means may itself be a syringe, pipette, and/or other such like apparatus, from which the formulation may be applied to the pancreas, for example. However, the components of the kit may be provided as dried powder(s). When reagents and/or components are provided as a dry powder, the powder can be reconstituted by the addition of a suitable solvent. It is envisioned that the solvent may also be provided in another container means.

VIII. TFAP2A as a Marker for Other Cancers

In some embodiments of the invention, TFAP2A level is assayed for detection of a cancer other than ovarian cancer. Although TFAP2A may be indicative of having or being at greater risk for having any cancer other than ovarian cancer, in specific embodiments, the cancer is of the uterus, breast, lung, prostate, colon, brain, bone, liver, pancreas, cervix, testes, spleen, skin, gall bladder, esophagus, bladder, kidney, thyroid, blood, and so forth. In specific embodiments, level of TFAP2A protein and/or mRNA is increased or decreased in a cancer other than ovarian cancer when compared to a control. In specific embodiments, markers in addition to TFAP2A are employed with TFAP2A to detect the presence or increased risk of having a particular type of cancer. Exemplary other tumor markers include prostate-specific antigen (PSA) for prostate cancer, calcitonin for medullary thyroid cancer, alpha-fetoprotein (AFP) for liver cancer and human chorionic gonadotropin (HCG) for germ cell tumors, such as testicular cancer and ovarian cancer.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Molecular Biomarker Set for Detection of Ovarian Cancer

The inventors compared the expression levels of genes in cancerous tissues categorized as stage IA, IC, and IIIC. FIG. 1 demonstrates that the expression of TFAP2A gene is higher in early stages (stages IA and IC) as well as advanced stage (IIIC) of the ovarian cancer as compared to the normal tissue (FIG. 1).

Kothandaraman et al. (2010) described E2F5 as a biomarker of ovarian cancer and they showed that the use of E2F5 in combination with CA125 increased sensitivity of ovarian cancer detection to 97.9% (an increase from 87.5% if only CA125 is used) in the case when the status of any of E2F5 or CA125 is confirmed. If the status of both E2F5 and CA125 is confirmed, the specificity of ovarian cancer detection increases to 72.5% (an increase from 55% if only CA125 is used) in a subset of patients. This study is the evidence that the combination markers can be more useful in diagnosing ovarian cancer. To further enhance the accuracy of ovarian cancer detection at early stages, the inventions set forth that the combination of TFAP2A, E2F5, and CA125 are useful for increased accuracy in detection of ovarian cancer. Two of these biomarkers i.e. E2F5 and CA125 have already been published and the computational analysis has detected TFAP2A as a biomarker of ovarian cancer.

The inventors describe here the identification of a new biomarker using computational methods that is useful for diagnosis of ovarian cancer. The results are based on a set A of 323 experimentally validated OC implicated genes compiled from literature. For this gene set, the inventors determined putative transcription factors (TFs) that control gene activation. The inventors ranked these TFs based on the number of genes they control in set A. In this way, the inventors selected top-ranked TFs as potential biomarkers for set A. Comparing the expression of top-ranked TFs in OC and normal cases based on published data (Lu et al., 2004, Hendrix et al., 2006, Adib et al., 2004), we identified TF named TFAP2A as a new biomarker for detection of ovarian cancer. The newly identified biomarker TFAP2A was compared with known marker CA125 in terms of expression in cancer patients in relevant published datasets.

Example 2

Exemplary Clinical Application of the Invention

In certain embodiments of the invention, an individual that is suspected of having ovarian cancer (for example, because of one or more test results and/or symptoms of ovarian cancer; an individual that is at risk for developing ovarian cancer (for example, because of a family history); an individual presently or previously on therapy for ovarian cancer; or an individual practicing routine health checks for ovarian cancer is subjected to methods of the invention for determining expression levels of TFAP2A, E2F5, and/or CA125.

The individual provides a sample to be tested. The sample may be processed by the same person or organization that obtains the sample, or the sample may be forwarded to another party for assaying or may be stored appropriately. The sample may be a biological fluid sample such as a blood sample, although in some cases the sample is an ovarian biopsy. The sample may be further processed, for example, blood may be fractionated, or ovarian tissue may have nucleic acid extracted. The respective mRNA or protein may be obtained from the sample by routine methods in the art, and is level is obtained and compared to a control, which may also be referred to as a standard. The control may comprise levels of TFAP2A, E2F5, and CA125 that are obtained from one or more normal individuals (persons without the respective cancer), and these levels may be obtained from the respective fluid or tissue in the normal individual(s). In the case of ovarian biopsy, for example, the level may be obtained from ovarian tissue in a region of the ovary being tested that detectably lacks cancerous cells and/or may be from the second ovary of the individual than the one being tested. In other ovarian biopsy cases, the level is obtained from one or more normal individuals.

Example 3

Combinations of Biomarkers for Detection of Ovarian Cancer

The present example provides exemplary methods demonstrating detection of at least one ovarian cancer markers.
Samples The RNA samples for 100 individuals were obtained from a commercial supplier and the distribution of samples is as follows:

TABLE 1

Distribution of tissue samples used for gene expression study

| Sample detail | Sample Numbers |
|---|---|
| Ovarian Cancer (OC) | 60 |
| Breast cancer | 10 |
| Cervix cancer | 10 |
| Uterus cancer | 10 |
| Non-cancerous ovary | 10 |

The RNA was extracted from the respective tissues by standard means in the art.

Exemplary Experimental Procedures

The 100 RNA samples underwent quality control (QC) using a bioanalyzer prior to cDNA synthesis with the ABI high capacity cDNA synthesis kit. The cDNA was then analyzed against five commercially available TaqMan® gene expression assays (Table 2) with the ABI TaqMan0 gene expression protocol using the 7900HT RT-PCR instrument.

TABLE 2

TaqMan ® Assays used in gene expression study

| | Inventory Code | Gene Name | Gene Classification |
|---|---|---|---|
| 1 | Hs01029413_m1 | TFAP2A | Transcription Factor AP-2 α |
| 2 | Hs00231092_m1 | E2F5 | E2F Transcription Factor 5, p130 binding |
| 3 | Hs03928990_g1 | RN18S1 | RNA, 18S ribosomal 1 (exemplary housekeeping gene) |
| 4 | Hs03929097_g1 | GAPDH | Glyceraldehyde-3-phosphate dehydrogenase (exemplary housekeeping gene) |
| 5 | Hs01065189_m1 | MUC16 (CA125) | Mucin 16, cell surface associated | cDNA Synthesis and QC cDNA synthesis was performed according to the manufacturer's instructions using the ABI High Capacity cDNA synthesis kits and QC was carried out using the Nanodrop instrument. Good quality cDNA was produced with an average cDNA yield of ~1490 ng/µl per sample. The 260/280 and 260/230 ratios were within the optimal range with average values of 1.8 and 2.0, respectively.

qRT-PCR QC and Analysis

A 1 µl aliquot from each of the 100 samples was pooled to create a standard sample. The standard sample was further subjected to QC with the nanodrop and diluted to make up a dilution series for standard curve analysis. A standard curve was generated for each gene and the TaqMan® assays were all found to be within 100±10% efficiency (Table 3), where a slope of −3.32 indicates an assay with 100% efficiency.

TABLE 3

Standard Curve efficiencies for the five genes under investigation

| Detector Name | Slope | $R^2$ |
|---|---|---|
| Hs01029413_m1_TFAPZA | −3.6017125 | 0.998070 |
| Hs00231092_m1_E2F5 | −3.5165527 | 0.9947431 |
| Hs03928990_g1_RN1851 | −3.56650 | 0.9986217 |
| Hs03929097_g1_GAPDH | −3.3637228 | 0.9978328 |
| Hs01065189_m1 MUC16 (CA125) | −3.5434833 | 0.99704236 |

For the experimental procedure, each sample was assayed in triplicate to limit technical variation. The assay comprised of cDNA samples mixed together with a cocktail containing the primer and probe pairs of the specific gene to be investigated. Samples were loaded onto a 384-well opti-clear PCR plate and the assay was performed under the ABI prescribed conditions on the 7900HT RT-PCR. Primary data analysis was executed with the use of the ABI SDS v2.3 software package.

Results

Average Ct values for each gene were provided for further analysis. Ct refers to cycle threshold and is defined as the number of cycles required for a fluorescent signal to cross a threshold. The threshold is the point where signal exceeds background level. The amount of amplified nucleic acid in the sample is inversely proportional to Ct (i.e. the lower the Ct level the greater the amount of target nucleic acid in the sample).

The inventors used ΔΔCt method to calculate the expression value for each gene. The method is summarized as follows:

Step 1:

$$\Delta Ct_{(Target\ gene)} = Ct_{(Target\ gene)} - Ct_{(housekeeping\ gene)}$$

Step 2:

$$\Delta\Delta Ct_{(OC)} = \Delta Ct_{(Target\ gene\ in\ OC)} - \Delta Ct_{(Target\ gene\ in\ non\text{-}OC\ (average))}$$

$$\Delta\Delta Ct_{(non\text{-}OC)} = \Delta Ct_{(Target\ gene\ in\ non\text{-}OC)} - \Delta Ct_{(Target\ gene\ in\ non\text{-}OC\ (average))}$$

Determining an accurate combination of biomarkers:

The expression data of target genes (TFAP2A, E2F5 and CA125) normalized against RN18S1 reference gene (control) (according to Steps 1 and 2 above) was used for predicting the accuracy of the diagnosis of OC using biomarkers in different combinations. Table 4 represents the results of this analysis. The terms "se", "sp" and "acc" denote sensitivity, specificity and accuracy, respectively. These parameters are calculated as follows:

$$se = tp/(tp+fn),$$

$$sp = tn/(tn+fp),$$

$$acc = (tp+tn)/(tp+fn+tn+fp),$$

where tp, tn, fp, fn stand for true positive, true negative, false positive and false negative outcome of diagnoses.

tp means that the OC case is diagnosed as being OC;

tn means that the non-OC case is diagnosed as being non-OC;

fp means that the non-OC case is diagnosed falsely as being OC;

fn means that the OC case is falsely diagnosed as being non-OC.

The columns in Table 4 represent the following:

'max se−(1−sp)' is a measure that shows how well OC cases are diagnosed relative to non-OC cases. (1−sp) shows the proportion of the non-OC cases diagnosed wrongly as being OC. Thus the difference between se and (1−sp) is a good indicator of the quality of diagnosis. The higher the value of 'se−(1−sp)', the more useful are the biomarkers.

Threshold for TFAP2A: the threshold th. In specific embodiments, $\Delta\Delta Ct_{(TFAP2A)}$>th in different combinations of biomarkers is useful for diagnosis of OC;

Threshold for E2F5: the threshold th. In specific embodiments, $\Delta\Delta Ct_{(E2F5)}$>th in different combinations of biomarkers is useful for diagnosis of OC;

Threshold for CA125: the threshold th. In specific embodiments, $\Delta\Delta Ct_{(CA125)}$>th in different combinations of biomarkers is useful for diagnosis of OC;

For different combinations of biomarkers (see Table 4), the threshold values were obtained by searching for the combination of thresholds that will maximize 'se−(1−sp)' subject to condition that this threshold has value between −10 and 10. The inventors used Direct Search optimization method from the Global Optimization Toolbox of Matlab package release 2011b (commercially available from Mathworks, Natick, Mass., USA).

N/A: means that particular biomarker is not used in the test.

cases, respectively, since the specificity of individual biomarker is very low. For example, CA125, which is a routinely used biomarker, could only classify 32% of cases as non-OC cases, whereas combination of the three exemplary biomarkers could identify 75% of non-OC cases. Therefore, the proposed combination of biomarkers (TFAP2A, CA125 and E2F5) has increased the overall accuracy to detect OC cases as well as non-OC cases as compared to other combinations of biomarkers/individual biomarkers. However, in alternative embodiments, TFAP2A alone is accurate to identify the presence of OC or risk of developing OC, or other cancers.

Example 4

Analysis Summary of Expression Behavior of Biomarkers in Breast, Cervix and Uterus Cancers This example describes the expression behavior of three biomarkers (TFAP2A, E2F5 and CA125) in samples obtained from breast, cervix and uterine cancers. The sample size for each cancer type and normal is 10. The expression level for each biomarker was assayed and quantitated essentially as described in Example 3. The following graphs represent the expression values observed for normal and cancers calculated as follows:

Step 1:

$\Delta Ct_{(Target\ gene)} = Ct_{(Target\ gene)} - Ct_{(housekeeping\ gene)}$

Step 2:

$\Delta\Delta Ct_{(cancer)} = \Delta Ct_{(Target\ gene\ in\ cancer)} - \Delta Ct_{(Target\ gene\ in\ normal\ (average))}$ $\Delta\Delta Ct_{(normal)} = \Delta Ct_{(Target\ gene\ in\ normal)} - \Delta Ct_{(Target\ gene\ in\ normal\ (average))}$

TABLE 4

The diagnostic value of different combinations of biomarkers was calculated based on threshold of ΔΔCt of each target biomarker.

| '&' means logical 'AND' '\|' means logical 'OR' | max se−(1−sp) | Sensitivity | Specificity | Accuracy | threshold for $\Delta\Delta Ct_{(TFAP2A)}$ | threshold for $\Delta\Delta Ct_{(E2F5)}$ | threshold for $\Delta\Delta Ct_{(CA125)}$ |
|---|---|---|---|---|---|---|---|
| TFAP2A & E2F5 & CA125 | 0.433333 | 0.683333 | 0.75 | 0.71 | −1.59 | −1.16 | −2.86 |
| TFAP2A \| E2F5 & CA125 | 0.383333 | 0.883333 | 0.5 | 0.73 | 7.13 | −0.85 | −2.66 |
| TFAP2A & E2F5 \| CA125 | 0.375 | 0.65 | 0.725 | 0.68 | −0.46 | −0.58 | 3.51 |
| TFAP2A & (E2F5 \| CA125) | 0.341667 | 0.716667 | 0.625 | 0.68 | −1.58 | 9.027 | −2.87 |
| TFAP2A \| E2F5 \| CA125 | 0.3 | 0.8 | 0.5 | 0.68 | −0.38 | 0.61 | 3.6 |
| E2F5 & CA125 | 0.383333 | 0.883333 | 0.5 | 0.73 | N/A | −0.85 | −2.76 |
| TFAP2A & CA125 | 0.341667 | 0.716667 | 0.625 | 0.68 | −1.62 | N/A | −2.87 |
| TFAP2A & E2F5 | 0.308333 | 0.633333 | 0.675 | 0.65 | −1.933 | −0.526 | N/A |
| E2F5 \| CA125 | 0.291667 | 0.866667 | 0.425 | 0.69 | N/A | −0.526 | 1.95 |
| TFAP2A \| E2F5 | 0.266667 | 0.816667 | 0.45 | 0.67 | 8.62 | −0.524 | N/A |
| TFAP2A \| CA125 | 0.258333 | 0.783333 | 0.475 | 0.66 | −0.75 | N/A | 3.53 |
| E2F5 | 0.266667 | 0.816667 | 0.45 | 0.67 | N/A | −0.526 | N/A |
| CA125 | 0.241667 | 0.916667 | 0.325 | 0.68 | N A | N/A | −2.474 |
| TFAP2A | 0.183333 | 0.733333 | 0.45 | 0.62 | −1.59 | N/A | N/A |

Table 4 shows that combination of TFAP2A & E2F5 & CA125 has max value of se−(1−sp)=0.433 (first data row in Table 4) for the samples analyzed, which is highest than any other combination of biomarkers. This shows that the combination of these three biomarkers provides most confidence in diagnosing correctly 68% of OC cases and identifies correctly 75% of non-ovarian cases. Individually, each biomarker (last three rows of Table 4) E2F5, CA125 and TFAP2A can only identify 45%, 32% and 45% of non-OC The relative expression of each biomarker shown in the figures is calculated as $2^{(-\Delta\Delta ct)}$ (Arocho et al., 2006)

Exemplary Results

The results of the analysis are represented in the form of bar graphs for each cancer type and normal samples.

Figure 2:
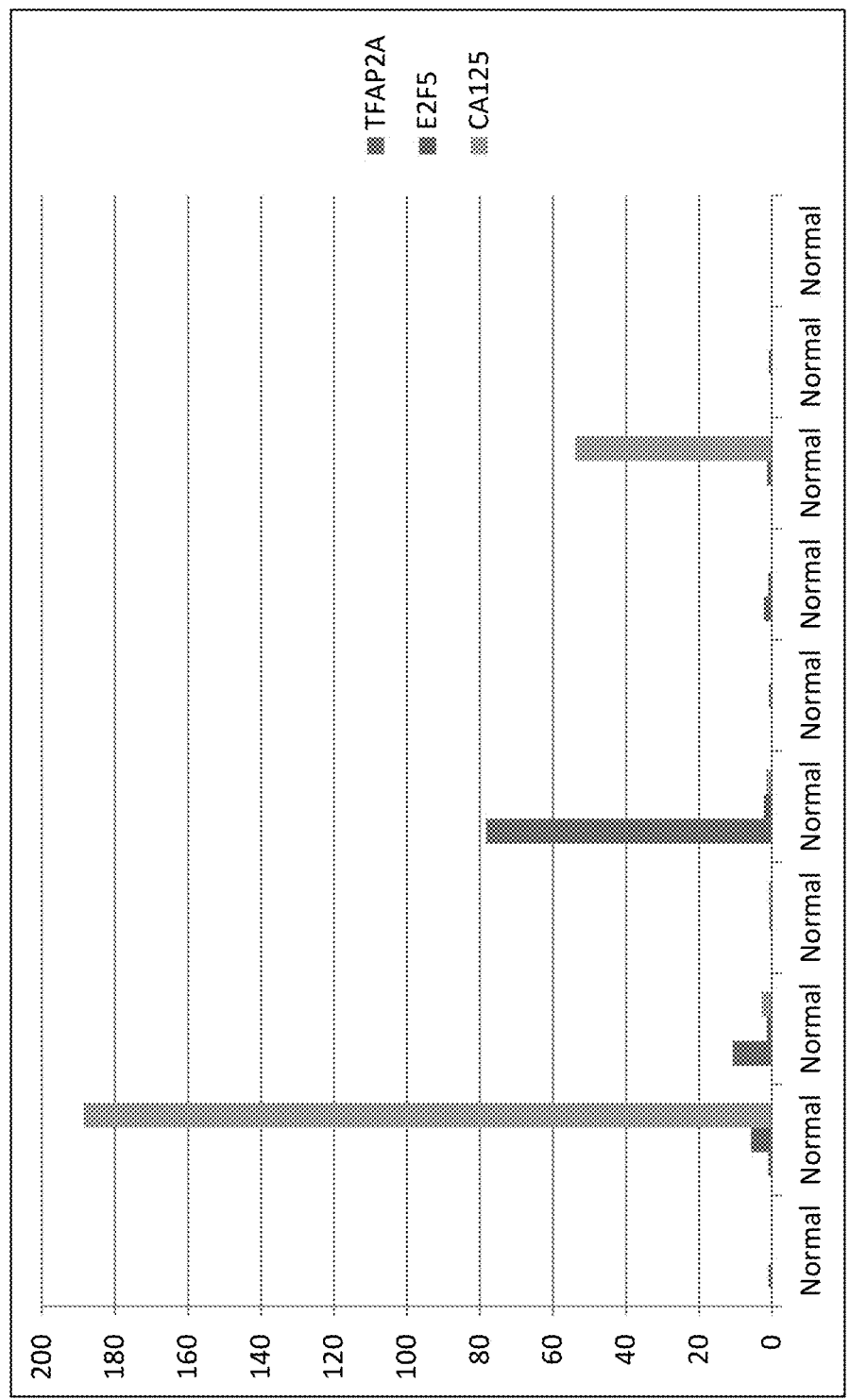
FIG. 2 shows a bar graph representing the expression pattern of three biomarkers (TFAP2A, CA125 and E2F5) in normal samples.

FIG. 2 shows a bar graph representing the expression pattern of three biomarkers in normal samples. The Y-axis represents the expression levels of biomarkers in each normal sample. The X-axis represents individual samples.

The expression of TFAP2A was very low or undetectable in 8/10 samples, the expression of E2F5 was low in most of the normal samples, whereas the expression of CA125 was low or was not detected in 8/10 samples.

Figure 3:
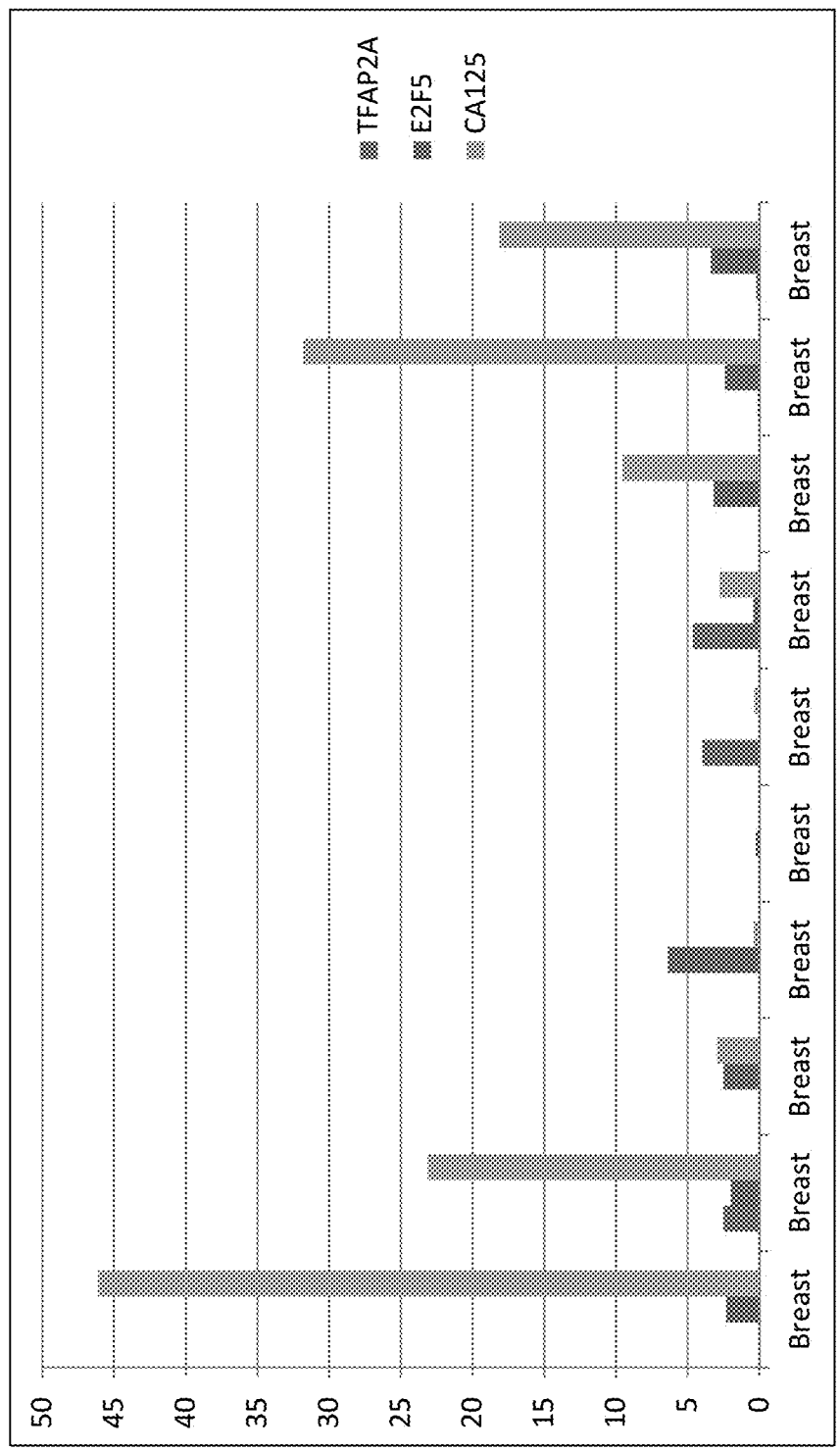
FIG. 3 shows the expression pattern of three biomarkers (TFAP2A, CA125 and E2F5) in breast cancer samples.

FIG. 3 shows the expression pattern of the three biomarkers in breast cancer samples. The Y-axis represents the expression levels of biomarkers in each breast cancer sample. The X-axis represents individual samples. In breast cancer samples, the expression level of CA125 was higher than the control in 7/10 samples. Zero on the Y-axis is the lowest boundary on expression, i.e. it means no expression.

Figure 4:
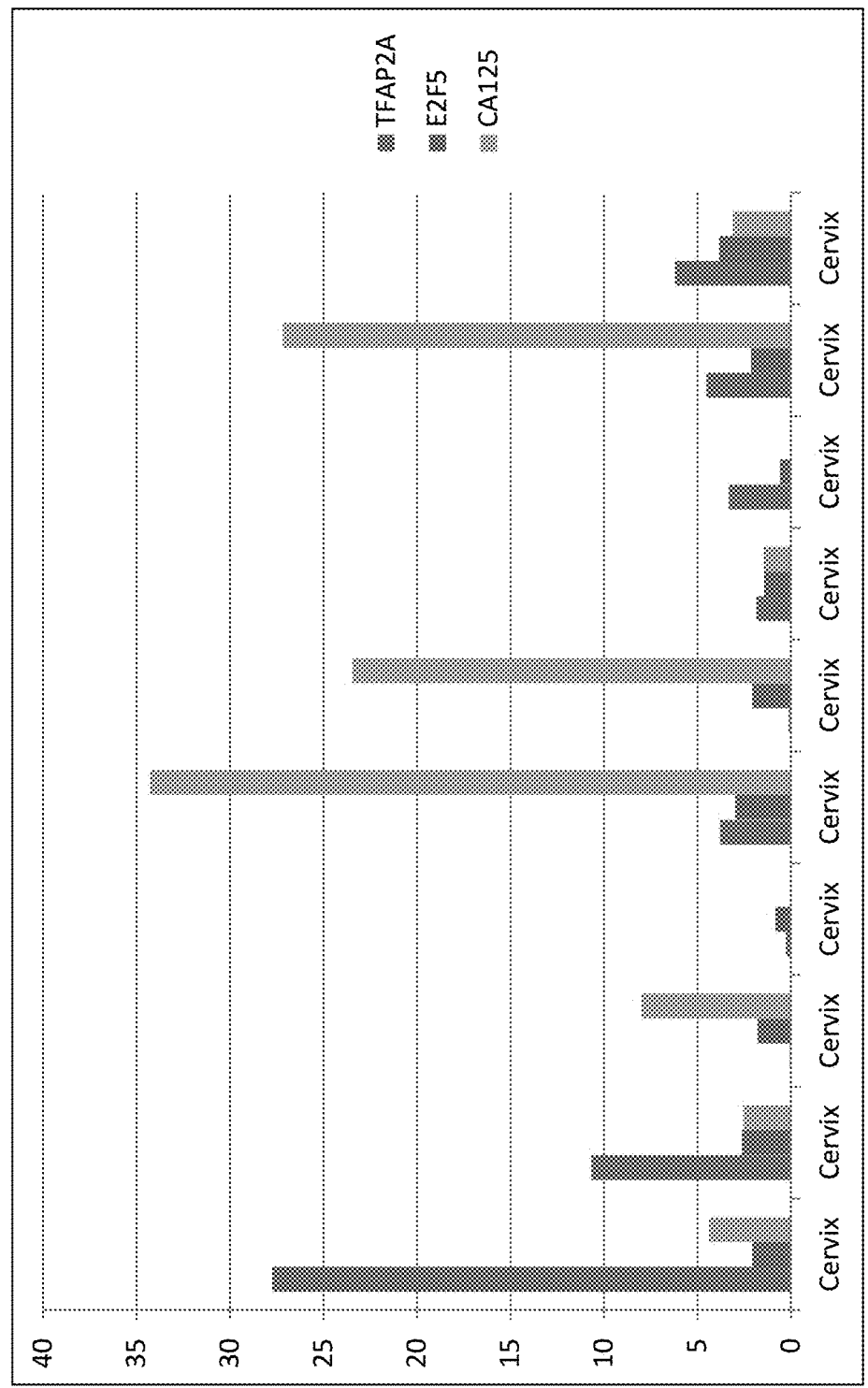
FIG. 4 shows the expression pattern of three biomarkers (TFAP2A, CA125 and E2F5) in cervix cancer samples.

FIG. 4 shows the expression pattern of the three biomarkers in cervix cancer samples. The Y-axis represents the expression levels of biomarkers in each cervix cancer sample. The X-axis represents individual samples. Six out of 10 cervix cancer samples had higher expression levels than the control for all three biomarkers.

Figure 5:
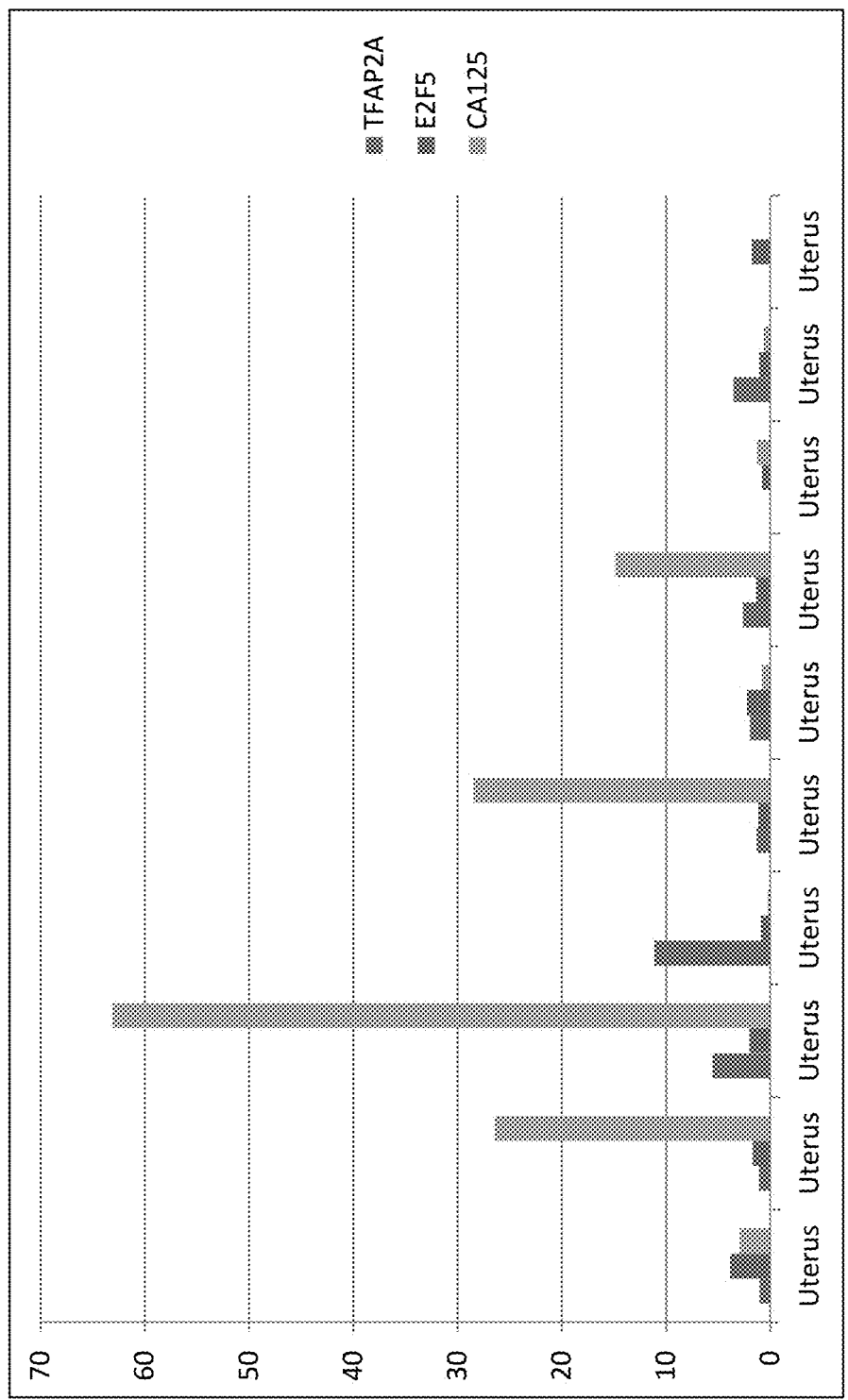
FIG. 5 demonstrates the expression pattern of three biomarkers (TFAP2A, CA125 and E2F5) in uterus cancer samples.

FIG. 5 demonstrates the expression pattern of the three biomarkers in uterus cancer samples. The Y-axis represents the expression levels of biomarkers in each uterus cancer sample. The X-axis represents individual samples.

REFERENCES

The following references, to the extent that they provide exemplary procedural or other details supplementary to those set forth herein, are specifically incorporated herein by reference.

PATENTS AND PATENT APPLICATIONS

European Application No. 320 308
European Application No. 329 822
GB Application No. 2 202 328
PCT Application No. PCT/US87/00880
PCT Application No. PCT/US89/01025
PCT Application No. PCT/US03/00531
PCT Application WO 88/10315
PCT Application WO 89/06700
PCT Application WO 90/07641
U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241
U.S. Pat. No. 4,683,195
U.S. Pat. No. 4,683,202
U.S. Pat. No. 4,800,159
U.S. Pat. No. 4,883,750
U.S. Pat. No. 4,946,773
U.S. Pat. No. 5,279,721
U.S. Pat. No. 5,840,873
U.S. Pat. No. 5,843,663
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,548
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 4,683,202
U.S. Pat. No. 4,800,159
U.S. Pat. No. 5,849,486
U.S. Pat. No. 5,851,772
U.S. Pat. No. 5,900,481
U.S. Pat. No. 5,919,626
U.S. Pat. No. 7,605,003
U.S. Pat. No. 7,741,019
U.S. Pat. No. 7,745,149

PUBLICATIONS

Adib T R, Henderson S, Perrett C, Hewitt D, Bourmpoulia D, Ledermann J, Boshoff C: Predicting biomarkers for ovarian cancer using gene-expression microarrays. Br J Cancer 2004, 90:686-692.

Arocho Alaina, Ladanyi Marc, Pan Qiulu. Validation of the 2-[DELTA][DELTA]Ct Calculation as an Alternate Method of Data Analysis for Quantitative PCR of BCR-ABL P210 Transcripts. Diagnostic Molecular Pathology: March 2006—Volume 15—Issue 1—pp 56-61

Bär M, Bär D, Lehmann B: Selection and validation of candidate housekeeping genes for studies of human keratinocytes—review and recommendations. J Invest Dermatol. 2009, 129(3):535-7. Review.

Frohman, In: PCR PROTOCOLS: A GUIDE TO METHODS AND APPLICATIONS, Academic Press, N.Y., 1990.

Hendrix N D, Wu R, Kuick R, Schwartz D R, Fearon E R, Cho K R: Fibroblast growth factor 9 has oncogenic activity and is a downstream target of Wnt signaling in ovarian endometrioid adenocarcinomas. Cancer Res 2006, 66:1354-1362.

Innis et al., "DNA sequencing with *Thermus aquaticus* DNA polymerase and direct sequencing of polymerase chain reaction-amplified DNA," Proc Natl Acad Sci USA. 85(24): 9436-9440, 1988.

Kothandaraman N, Bajic V B, Brendan P N, Huak C Y, Keow P B, Razvi K, Salto-Tellez M, Choolani M. E2F5 status significantly improves malignancy diagnosis of epithelial ovarian cancer. BMC Cancer. 2010 Feb. 24; 10:64.

Kwoh et al., "Transcription-based amplification system and detection of amplified human immunodeficiency virus type 1 with a bead-based sandwich hybridization format, Proc Natl Acad Sci USA. 86(4):1173-1177, 1989.

Lu K H, Patterson A P, Wang L, Marquez R T, Atkinson E N, Bagerly K A, Ramoth L R, Rosen D G, Liu J, Hellstrom I, et al.: Selection of potential markers for epithelial ovarian cancer with gene expression arrays and recursive descent partition analysis. Clin Cancer Res 2004, 10:3291-3300.

Ohara et al., "One-sided polymerase chain reaction: the amplification of cDNA," Proc Natl Acad Sci USA. 86(15): 5673-5677, 1989.

Sasaroli D, Coukos G, Scholler N: Beyond CA125: the coming of age of ovarian cancer biomarkers. Are we there yet? Biomark Med 2009, 3:275-288.

Tunbridge E M, Eastwood S L, Harrison P J: Changed relative to what? Housekeeping genes and normalization strategies in human brain gene expression studies. Biol Psychiatry. 2011 Jan. 15; 69(2):173-9. Review Walker et al., "Strand displacement amplification—an isothermal, in vitro DNA amplification technique," Nucleic Acids Res. 20(7):1691-1696, 1992

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of identifying an individual to be treated for ovarian cancer, consisting of: a) detecting expression levels of TFAP2A, E2F5, and CA125 from a sample obtained from the individual; b) selecting the individual for treatment when expression levels of TFAP2A, E2F5, and CA125 are higher relative to the expression levels of TFAP2A, E2F5, and CA125 from a control; and c) administering to the individual a treatment for ovarian cancer, wherein the treatment for ovarian cancer is selected from the group consisting of surgery, radiation, and chemotherapy.

2. The method of claim 1, wherein the expression levels are determined by protein level or mRNA level of TFAP2A, CA125 and E2F5.

3. The method of claim 2, wherein the protein level of TFAP2A, CA125 and E2F5 is determined with an antibody.

4. The method of claim 2, wherein the mRNA levels of TFAP2A, CA125 and E2F5 from the individual are determined.

5. The method of claim 2, wherein the mRNA level is determined from ovarian tissue or blood from the individual.

6. The method of claim 1, wherein the control is tissue or blood from one or more normal individuals or is from tissue or blood from the individual.

7. The method of claim 1, wherein the method detects the stage of ovarian cancer in the individual.

8. The method of claim 7, wherein the stage is stage IA, IC, IIIC, or a combination thereof.

9. A method of identifying an individual to be treated for ovarian cancer, consisting of: a) detecting expression levels of TFAP2A, E2F5, and CA125 from a sample obtained from the individual; b) selecting the individual for treatment when expression levels of TFAP2A, E2F5, and CA125 are higher relative to the expression levels of TFAP2A, E2F5, and CA125 from a control; c) performing an additional ovarian cancer detection method; and d) administering to the individual a treatment for ovarian cancer, wherein the treatment for ovarian cancer is selected from the group consisting of surgery, radiation, and chemotherapy, and wherein the additional ovarian cancer detection method is selected from the group consisting of palpitation, ultrasound, magnetic resonance imaging, X-ray, CT scan, blood testing, and biopsy.

10. The method of claim 1, wherein the sample is ovarian tissue, blood, serum, or plasma.

11. The method of claim 1, wherein the chemotherapy includes administering a chemotherapeutic agent selected from the group consisting of drugs that contain platinum and taxane compounds.

12. The method of claim 11, wherein the chemotherapeutic agent is selected from the group consisting of cisplatin, carboplatin, and paclitaxel.

13. The method of claim 1, wherein chemotherapy comprises administering an effective amount of melphalan, doxorubicin, altretamine, 5-fluorouracil, topotecan, ifosamide, and etoposide.

* * * * *